US008715953B2

(12) United States Patent  (10) Patent No.: US 8,715,953 B2
Kaundinya et al.  (45) Date of Patent: *May 6, 2014

(54) ANALYSIS OF SULFATED POLYSACCHARIDES

(71) Applicants: Ganesh Kaundinya, Bedford, MA (US); Zachary Shriver, Cambridge, MA (US); Mallikarjun Sundaram, Flemington, NJ (US); Yi-wei Qi, Manlius, NY (US); Ram Sasisekharan, Cambridge, MA (US)

(72) Inventors: Ganesh Kaundinya, Bedford, MA (US); Zachary Shriver, Cambridge, MA (US); Mallikarjun Sundaram, Flemington, NJ (US); Yi-wei Qi, Manlius, NY (US); Ram Sasisekharan, Cambridge, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,257

(22) Filed: Nov. 1, 2013

(65) Prior Publication Data
US 2014/0057358 A1 Feb. 27, 2014

Related U.S. Application Data

(63) Continuation of application No. 13/602,979, filed on Sep. 4, 2012, now abandoned, which is a continuation of application No. 13/086,054, filed on Apr. 13, 2011, now abandoned, which is a continuation of application No. 12/203,629, filed on Sep. 3, 2008, now Pat. No. 7,947,507, which is a continuation of application No. 10/386,402, filed on Mar. 11, 2003, now Pat. No. 7,575,886.

(60) Provisional application No. 60/363,240, filed on Mar. 11, 2002, provisional application No. 60/383,903, filed on May 28, 2002, provisional application No. 60/393,973, filed on Jul. 5, 2002.

(51) Int. Cl.
C12Q 1/34 (2006.01)
A61K 31/727 (2006.01)
C08B 37/10 (2006.01)

(52) U.S. Cl.
USPC ................................. 435/18; 514/56; 536/21

(58) Field of Classification Search
None
See application file for complete search history.

(56) References Cited

U.S. PATENT DOCUMENTS

| | | |
|---|---|---|
| 3,832,253 A | 8/1974 | DiPalma |
| 3,854,480 A | 12/1974 | Zaffaroni |
| 4,452,775 A | 6/1984 | Kent |
| 4,652,555 A | 3/1987 | Goulay et al. |
| 4,667,014 A | 5/1987 | Nestor, Jr. et al. |
| 4,686,288 A | 8/1987 | Lormeau et al. |
| 4,687,765 A | 8/1987 | Vairel et al. |
| 4,692,435 A | 9/1987 | Lormeau et al. |
| 4,748,034 A | 5/1988 | de Rham |
| 4,791,195 A | 12/1988 | Bianchini et al. |
| 4,826,827 A | 5/1989 | Lormeau et al. |
| 4,847,338 A | 7/1989 | Linhardt et al. |
| 4,916,219 A | 4/1990 | Linhardt et al. |
| 4,933,326 A | 6/1990 | Bianchini et al. |
| 4,977,250 A | 12/1990 | Diaz et al. |
| 4,981,955 A | 1/1991 | Lopez |
| 4,990,502 A | 2/1991 | Lormeau et al. |
| 5,010,063 A | 4/1991 | Piani et al. |
| 5,013,724 A | 5/1991 | Petitou et al. |
| 5,013,725 A | 5/1991 | Isomura et al. |
| 5,019,649 A | 5/1991 | Lormeau et al. |
| 5,032,679 A | 7/1991 | Brandley et al. |
| 5,039,529 A | 8/1991 | Bergendal et al. |
| 5,084,564 A | 1/1992 | Vila et al. |
| 5,104,860 A | 4/1992 | Piani et al. |
| 5,106,734 A | 4/1992 | Nielsen |
| 5,110,918 A | 5/1992 | Casu et al. |
| 5,164,378 A | 11/1992 | Conti et al. |
| 5,239,660 A | 8/1993 | Ooi |
| 5,264,425 A | 11/1993 | Dal Pozzo et al. |
| 5,296,471 A | 3/1994 | Holme et al. |
| 5,340,932 A | 8/1994 | Fussi et al. |
| 5,380,716 A | 1/1995 | Conrad et al. |
| 5,389,618 A | 2/1995 | Debrie |
| 5,403,827 A | 4/1995 | De-Ambrosi |
| 5,410,039 A | 4/1995 | Ungarelli et al. |
| 5,430,132 A | 7/1995 | Silvano et al. |
| 5,430,133 A | 7/1995 | Piani et al. |

(Continued)

FOREIGN PATENT DOCUMENTS

EP 121067 B1 10/1984
EP 244235 B1 11/1987

(Continued)

OTHER PUBLICATIONS

Wang et al. "Cloning genes encoding MHC Claa II-restricted antigens: mutated CDC27 as a tumor antigen", Science, 1999, vol. 284, pp. 1351-1354.

(Continued)

Primary Examiner — Susan Hanley
Assistant Examiner — Paul Martin
(74) Attorney, Agent, or Firm — Lando & Anastasi LLP

(57) ABSTRACT

The invention relates to methods and products associated with analyzing and monitoring heterogeneous populations of sulfated polysaccharides. In particular therapeutic heparin products including low molecular weight heparin products and methods of analyzing and monitoring these products are described.

5 Claims, 11 Drawing Sheets

(56) References Cited

U.S. PATENT DOCUMENTS

| | | | |
|---|---|---|---|
| 5,599,801 A | 2/1997 | Branellec et al. | |
| 5,668,118 A | 9/1997 | Kennedy | |
| 5,696,100 A | 12/1997 | Holme et al. | |
| 5,707,973 A | 1/1998 | Baron et al. | |
| 5,707,974 A | 1/1998 | Kennedy | |
| 5,721,973 A | 2/1998 | Mizukawa | |
| 5,763,421 A | 6/1998 | Caretto et al. | |
| 5,767,269 A | 6/1998 | Hirsh et al. | |
| 5,783,570 A | 7/1998 | Yokota et al. | |
| 5,808,021 A | 9/1998 | Holme et al. | |
| 5,849,721 A | 12/1998 | Uzan | |
| 5,912,237 A | 6/1999 | Kennedy | |
| 5,922,358 A | 7/1999 | Doutremepuich et al. | |
| 5,935,850 A | 8/1999 | Clark et al. | |
| 5,958,899 A | 9/1999 | Zoppetti et al. | |
| 6,045,805 A | 4/2000 | Moreau | |
| 6,075,013 A | 6/2000 | Weitz et al. | |
| 6,077,683 A | 6/2000 | Kennedy | |
| 6,143,730 A | 11/2000 | Parish et al. | |
| 6,197,943 B1 | 3/2001 | Casu et al. | |
| 6,217,863 B1 | 4/2001 | Godavarti et al. | |
| 6,228,998 B1 | 5/2001 | Miura et al. | |
| 6,232,093 B1 | 5/2001 | Van Houdenhoven et al. | |
| 6,255,296 B1 | 7/2001 | Daniels | |
| 6,258,798 B1 | 7/2001 | Wallentin | |
| 6,346,517 B1 | 2/2002 | Wong et al. | |
| 6,384,021 B1 | 5/2002 | Mardiguian | |
| 6,492,503 B1 | 12/2002 | Kariya et al. | |
| 6,617,316 B1 | 9/2003 | Mourier et al. | |
| 6,812,221 B2 | 11/2004 | McKeehan et al. | |
| RE38,743 E | 6/2005 | Debrie | |
| 7,008,933 B2 | 3/2006 | Welzel | |
| 7,083,937 B2 | 8/2006 | Sasisekharan et al. | |
| 7,390,633 B2 | 6/2008 | Liu et al. | |
| 7,575,886 B2 | 8/2009 | Venkataraman et al. | |
| 7,585,642 B2 | 9/2009 | Sasisekharan et al. | |
| 7,687,579 B2 | 3/2010 | Takahashi et al. | |
| 7,790,466 B1 | 9/2010 | Shriver et al. | |
| 7,811,827 B2 | 10/2010 | Raguram | |
| 7,816,144 B1 | 10/2010 | Shriver et al. | |
| 7,968,082 B1 | 6/2011 | Shriver et al. | |
| 8,003,402 B2 | 8/2011 | Yamamoto et al. | |
| 8,076,149 B1 | 12/2011 | Shriver et al. | |
| 8,101,733 B1 | 1/2012 | Shriver et al. | |
| 2002/0169143 A1 | 11/2002 | Sasisekharan et al. | |
| 2003/0203385 A1 | 10/2003 | Venkataraman et al. | |
| 2004/0198697 A1 | 10/2004 | Cohen et al. | |
| 2004/0265943 A1 | 12/2004 | Viskov et al. | |
| 2005/0119477 A1 | 6/2005 | Mourier et al. | |
| 2005/0186679 A1 | 8/2005 | Viskov et al. | |
| 2005/0215519 A1 | 9/2005 | Viskov et al. | |
| 2005/0288252 A1 | 12/2005 | Nurcombe et al. | |
| 2006/0024664 A1 | 2/2006 | Sasisekharan et al. | |
| 2006/0182734 A1 | 8/2006 | Liu et al. | |
| 2007/0065921 A1 | 3/2007 | Sasisekharan et al. | |
| 2007/0098708 A1 | 5/2007 | Myette | |
| 2007/0134226 A1 | 6/2007 | Myette | |
| 2007/0161073 A1 | 7/2007 | Sasisekharan et al. | |
| 2007/0287683 A1 | 12/2007 | Shriver et al. | |
| 2008/0009069 A1 | 1/2008 | Mourier et al. | |
| 2008/0318328 A1 | 12/2008 | Viskov et al. | |
| 2010/0279269 A1 | 11/2010 | Parsons et al. | |
| 2011/0207919 A1 | 8/2011 | Beccati et al. | |

FOREIGN PATENT DOCUMENTS

| | | | |
|---|---|---|---|
| EP | 244236 A2 | 11/1987 | |
| EP | 245813 B1 | 11/1987 | |
| EP | 268885 B1 | 6/1988 | |
| EP | 293539 A2 | 12/1988 | |
| EP | 302034 B1 | 2/1989 | |
| EP | 347588 B1 | 12/1989 | |
| EP | 423151 B1 | 9/1993 | |
| EP | 380943 B1 | 9/1994 | |
| EP | 432537 B1 | 1/1995 | |
| EP | 483733 B1 | 8/1996 | |
| EP | 623629 B1 | 8/1996 | |
| EP | 625166 B1 | 9/1997 | |
| EP | 557887 B1 | 12/1997 | |
| EP | 708785 B1 | 3/1999 | |
| EP | 693499 B1 | 12/1999 | |
| EP | 789777 B1 | 8/2000 | |
| EP | 970130 B1 | 7/2002 | |
| EP | 735050 B1 | 9/2002 | |
| EP | 1580197 A1 | 9/2005 | |
| EP | 1582531 A1 | 10/2005 | |
| EP | 1586588 A1 | 10/2005 | |
| JP | 11230935 A | 8/1999 | |
| WO | 8809347 A1 | 12/1988 | |
| WO | 9003791 A1 | 4/1990 | |
| WO | 9914326 A1 | 3/1999 | |
| WO | 0065521 A2 | 11/2000 | |
| WO | 0129055 A2 | 4/2001 | |
| WO | 0223190 A2 | 3/2002 | |
| WO | 0232406 A2 | 4/2002 | |
| WO | 03078960 A2 | 9/2003 | |
| WO | 2004027087 A2 | 4/2004 | |
| WO | 2005009040 A2 | 1/2005 | |
| WO | 2005080438 A1 | 9/2005 | |
| WO | 2005090411 A1 | 9/2005 | |

OTHER PUBLICATIONS

Wang et al., "A breast and melanoma-shared tumor antigen: T cell response to antigenic peptides translated from different open reading frames", J. Immunol., 1998, vol. 161, pp. 3596-3606.

Wang et al., "Identification of TRP-2 as a human tumor antigen recognized by cytotoxic T lymphocytes", J. Exp. Med., 1996, vol. 184, pp. 2207-2216.

Wang et al., "Utilization of an alternative open reading frame of a normal gene in generating a novel human cancer antigen", J. Exp. Med., 1996, vol. 183, pp. 1131-1140.

Watt et al., "Comparison of ovine, bovine and porcine mucosal heparins and low molecular weight heparins by disaccharide analyses and 13C NMR", Carbohydrate Polymers, 1997, vol. 33, pp. 5-11.

Wölfel et al., "A p16INK4a-insensitive CDK4 mutant targeted by cytolytic T lymphocytes in a human melanoma", Science, 1995, vol. 269, pp. 1281-1284.

Wölfel et al., "Two tyrosinase nonapeptides recognized on HLA-A2 melanomas by autologous cytolytic T lymphocytes", Eur. J. Immunol., 1994, vol. 24, pp. 759-764.

Yates et al., "1H and 13C NMR spectral assignments of the major sequences of twelve systematically modified heparin derivatives", Carbohydrate Research, 1996, vol. 294, pp. 15-27.

Yoshida et al., "Analyisis of unsaturated disaccharides from glycosaminoglycuronan by high-performance liquid chromatography", Analytical Biochem., 1989, vol. 117, pp. 327-332.

Zorn et al., "A MAGE-6-encoded peptide is recognized by expanded lymphocytes infiltrating a spontaneously regressing human primary melanoma lesion", Eur. J. Immunol., 1999, vol. 29, pp. 602-607.

"2.6.26. Test for anti-D antibodies in intravenous immunglobulin", Pharmeuropa, Jan. 2004, vol. 16, No. 1, pp. 121-122.

Aarnoudse et al., "Interleukin-2-induced, melanoma-specific T cells recognize CAMEL, an unexpected translation product of LAGE-1" Int. J. Cancer, 1999, vol. 82, pp. 442-448.

Alban et al., "Development of SPC-ELISA: a new assay principle for the study of sulfated polysaccharide-protein interactions", Journal of Biomolecular Screening, 2001, vol. 6, No. 6, pp. 393-400.

Amended Complaint—*Momenta Pharmaceuticals, Inc. and Sandoz Inc.*, Plaintiffs, v. *Amphastar Pharmaceuticals, Inc., International Medication Systems, Ltd., Watson Pharmaceuticals, Inc., and Watson Pharma, Inc.*, Defendants. 2011 WL 9556659.

Ampofo et al., "Disaccharide compositional analysis of heparin and heparan sulfate using capillary zone electrophoresis", Analytical Biochemistry, 1991, vol. 199, pp. 249-255.

Ansel et al., "Pharmaceutical dosage forms and drug delivery systems", 1999, pp. 23-27 and 54-59, published by Lippincott Williams & Wilkins.

(56) References Cited

OTHER PUBLICATIONS

Anumula et al., "High resolution and high sensitivity methods for oligosaccharide mapping and characterization by normal phase high performance liquid chromatography following derivatization with highly fluorescent anthranilic acid", Glycobiology, 1998, vol. 8, No. 7, pp. 685-694.
Araki et al., "Application of 2-aminopyridine fluorescence labeling in the analysis of in vivo and in vitro metabolism of dextran sulfate sodium by size-exclusion high-performance liquid chromatorgraphy", J. Chromatography B Biomed. Sci., 2001, vol. 753, No. 2, pp. 209-215.
Bartolucci et al., "Inhibition of human leukocyte elastase by chemically and naturally oversulfated galactosaminoglycans", Carbohydrate Research, 1995, vol. 276, No. 2, pp. 401-408.
Bennett et al., "High resolution analysis of functional determinants on human tissue-type plasminogen activator", J. of Biological Chemistry, 1991, vol. 266, No. 8, pp. 5191-5201.
Bianchini et al., "Few bicyclic acetals at reducing end of low-molecular-weight heparins: might they restrict specification of pharmacopoeia?" Pharmeuropa Scientific Notes, 2005, vol. 1, pp. 1-3.
Bianchini et al., "Variability of heparins and heterogeneity of low molecular weight heparins" Seminars in Thrombosis and Hemostasis, 2007, vol. 33, pp. 496-502.
Bigge et al., "Nonselective and efficient fluorescent labeling of glycans using 2-amino benzamide and anthranilic acid", Anal. Biochem., 1995, vol. 230, No. 2, pp. 229-238.
Binari et al., "Genetic evidence that heparin-like glycosaminoglycans are involved in wingless signaling", Development, 1997, vol. 124, pp. 2623-2632.
Bosch et al., "Recognition of BCR-ABL positive leukemic blasts by human CD4+ T cells elicited by primary in vitro immunization with a BCR-ABL breakpoint peptide", Blood, 1996, vol. 88, pp. 3522-3527.
Bottio et al., "Life threatening anaphylactic shock caused by porcine heparin intravenous infusion during mitral valve repair," The Journal of Thoracic and Cardiovascular Surgery, 2003, vol. 126, pp. 1194-1195.
Boël et al. "BAGE: a new gene encoding an antigen recognized on human melanomas by cytolytic T lymphocytes", Immunity, 1995, vol. 2, pp. 167-175.
Brichard et al., "A tyrosinase nonapeptide presented by HLA-B44 is recognized on a human melanoma by autologous cytolytic T lymphocytes", Eur. J. Immunol., 1996, vol. 26, pp. 224-230.
Brief for Appellants—*Momenta Pharmaceuticals, Inc.*, Plaintiff-Appellee, *Sandoz, Inc*, Plaintiff-Appellee, v. *Amphastar Pharmaceuticals, Inc., International Medication Systems, Ltd., and Watson Pharmaceuticals, Inc.*, Defendants-Appellants. 2011 WL 7111556.
Brief in Opposition—*Momenta Pharmaceuticals, Inc.* v. *Amphastar Pharmaceuticals, Inc.* 2013 WL 2316705.
Brief of Plaintiffs—Appellees Momenta Pharmaceuticals, Inc. and Sandoz, Inc—*Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals, Inc. and Watson Pharma, Inc.*, Defendants-Appellants. 2011 WL 7039087.
Brossart et al., "Her-2/neu-derived peptides are tumor-associated antigens expressed by human renal cell and colon carcinoma lines and are recognized by in vitro induced specific cytotoxic T lymphocytes", Cancer Res., 1998, vol. 58, pp. 732-736.
Brändle et al., "A mutated HLA-A2 molecule recognized by autologous cytotoxic T lymphocytes on a human renal cell carcinoma", J. Exp. Med., 1996, vol. 183, pp. 2501-2508.
Campbell, S. A., Filed by Amphastar pharmaceuticals in response to citizen petition docket No. 03P-0064/CP1 filed with the United States Food and Drug Administration. Response filed on May 13, 2004, Entered into FDA docket system on Jun. 8, 2004.

Carlson et al., "The Determination of recombinant human tissue-type plasminogen activator activity by turbidimetry using a microcentrifugal analyzer", Analytical Biochem., 1988, vol. 168, pp. 428-435.
Castelli et al., "Mass spectromic identification of a naturally processed melanoma peptide recognized by CD8+ cytotoxic T lymphocytes", J. Exp. Med., 1995, vol. 181, pp. 363-368.
Castelli et al., "Novel HLA-Cw8-restricted T cell epitopes derived from tyrosinase-related protein-2 and gp100 melanoma antigens", J. Immunol., 1999, vol. 162, pp. 1739-1748.
Cerny et al., "Preparation of 2-amino-1,6-anhydro-2,3-dideoxy-b-D-arabino-hexopyranose. 1H- and 13C-N.M.R. spectra of deoxy derivatives of 2-amino-1,6-deoxy-D-glucose and 2-amino-1,6-anhydro-2-deoxy-D-mannose", Carbohydrate Research, 1984, vol. 130, pp. 103-114.
Chaux et al., "Identification of five MAGE-A1 epitopes recognized by cytolytic T lymphocytes obtained by in vitro stimulation with dendritic cells transduced with MAGE-A1", J. Immunol., 1999, vol. 163, pp. 2928-2936.
Chaux et al., "Identification of MAGE-3 epitopes presented by HLA-DR molecules to CD4(+) T lymphocytes", J. Exp. Med., 1999, vol. 189, pp. 767-778.
Chiari et al., "Two antigens recognized by autologous cytolytic T lymphocytes on a melanoma result form a single point mutation in an essential housekeeping gene", Cancer Res., 1999, vol. 59, pp. 5785-5792.
Citizens Petition filed with the United Staes Food and Drug Administration by Aventis Pharmaceuticals Inc. on Feb. 19, 2003.
Citizens Petition Supplemental filed with the United Staes Food and Drug Administration by Aventis Pharmaceuticals Inc. on Feb. 12, 2004.
Collard et al., "A novel approach to 14C lable N-linked oligosaccharides" Analyt. Biochem., 1997, vol. 247, No. 2, pp. 448-450.
Complaint—*Momenta Pharmaceuticals, Inc. and Sandoz Inc.*, Plaintiffs, v. *Amphastar Pharmaceuticals, Inc., International Medication Systems, Ltd. and Watson Pharmaceuticals, Inc.*, Defendants. 2011 WL 4592253.
Complaint—*Momenta Pharmaceuticals, Inc. and Sandoz Inc.*, Plaintiffs, v. *Teva Pharmaceuticals Industries Ltd and Teva Pharmaceuticals USA, Inc.*, Defendants. 2010 WL 4888034.
Correale et al., "In vitro generation of human cytotoxic T lymphocytes specific for peptides derived from prostate-specific antigen", J. Natl. Cancer Inst., 1997, vol. 89, pp. 293-300.
Corrected Brief for Appellants—*Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., and Watson Pharmaceuticals, Inc.*, Defendants-Appellants. 2011 WL 7111557.
Coulie et al., "A mutated intron sequence codes for an antigenic peptide recognized by cytolytic T lymphocytes on a human melanoma", Proc. Natl. Acad. Sci., 1995, vol. 92, pp. 7976-7980.
Coulie, "Antigens recognized on human tumors by cytolytic T lymphocytes: towards vaccination?", Stem Cells, 1995, vol. 13, pp. 393-403.
Cox et al., "Identification of a peptide recognized by five melanoma-specific human cytotoxic T cell lines", Science, 1994, vol. 264, pp. 716-719.
Da Col et at., "Characterization of the chemical structure of sulphated glycosaminoglycans after enzymatic digestion; Application for liquid chromatography-mass spectrometry with an atmospheric pressure interface", J. of Chromatography, 1993, vol. 647, pp. 289-300.
Dalmora et al., "Biological potency and physicochemical characterization of unfractionated heparins," Revista Brasileira de Hematologi e Hematerapia, 2009, vol. 31, No. 4, pp. 1-7.
Dawes et al., "The measurement of heparin and other therapeutic sulphated polysaccharides in plasma, serum and urine", Thrombosis and Haemostasis, 1985, vol. 54, No. 3, pp. 630-634.
De Backer et al., "Characterization of the GAGE genes that are expressed in various human cancers and in normal testis", Cancer Res., 1999, vol. 59, pp. 3157-3165.
Defendant Amphastar's Opening Claim Construction Brief—*Momenta Pharmaceuticals, Inc. and Sandoz, Inc.*, Plaintiffs, v.

(56) References Cited

OTHER PUBLICATIONS

*Amphastar Pharmaceuticals, Inc., International Medication Systems, Ltd. and Watson Pharamceuticals, Inc.*, Defendants. 2012 WL 6150799.
Defendant Teva's Reply Claim Construction Brief—*Momenta Pharmaceuticals, Inc. and Sandoz, Inc.*, Plaintiffs, v. *Teva Pharmaceuticals USA, Inc.*, Defendant. 2012 WL 2455760.
Defendant's Preliminary Claim Construction Brief *Momenta Pharmaceuticals, Inc. and Sandoz, Inc.*, Plaintiffs, v. *Teva Pharmaceuticals USA, Inc.* Defendant. 2012 WL 2455754.
Defendants' Amended Answer to Plaintiffs' Amended Complaint—*Momenta Pharmaceuticals, Inc., et al.*, Plaintiffs, v. *Amphastar Pharmaceuticals, Inc., et al.*, Defendants. 2012 WL 6150795.
Defendants' Answer to Plaintiffs' Amended Complaint—*Momenta Pharmaceuticals, Inc., et al.*, Plaintiffs, v. *Amphastar Pharmaceuticals, Inc., et al.*, Defendants. 2012 WL 6150796.
Keiser et al., "Preimplantation screening for transgenesis using an embryonic specific promoter and green fluorescent protein", Cloning, 2001, vol. 3, No. 1, pp. 21-30.
Kinoshita et al., "Microanalysis of glycosaminoglycan-derived oligosaccharides labeled with a fluorophore 2-aminobenzamide by high-performance liquid chromatography: application to disaccharide composition analysis and exosequencing of oligosaccharides", Analytical Biochem., 1999, vol. 269, pp. 367-378.
Kishimoto et al., "Contaminated heparin associated with adverse clinical events and activation of the contact system", The New England Journal of Medicine, Apr. 23, 2008, vol. 358, No. 23, pp. 2457-2467.
Kishimoto et al., "MII8—A rationally engineered low-molecular-weight heparin designed specifically for the treatment of acute coronary syndromes", Thrombosis and Haemostasis, 1999, vol. 102. No. 5. pp. 900-906.
Kittlesen et al., "Human melanoma patients recognize an HLA-A1-restricted CTL epitope from tyrosinase containing two cysteine residues: implications for tumor vaccine development", J. Immunol., 1998, vol. 160, pp. 2099-2106.
Kobayashi et al., "CD4+ T cells from peripheral blood of a melanoma patient recognize peptides derived from nonmutated tyrosinase", Cancer Research, 1998, vol. 58, pp. 296-301.
Kuhle et al., "Pharmacokinetic study of tinzaparin in pediatric patients", Blood, 2002, vol. 100, No. 11, Abstract No. 3975.
Lamari et al., "Analysis of glycosaminoglycan-derived disaccharides in biologic samples by capillary electrophoresis and protocol for sequencing glycosaminoglycans", Biomedical Chromatography, 2002, vol. 16, pp. 95-102.
Langer "New methods of drug delivery", Science, 1990, vol. 249, pp. 1527-1533.
Larnkjaer et al., "Binding of Low Molecular Weight Heparin (Tinzaparin sodium) to Bovine Endothelial Cells in vitro" Thrombosis Res., vol. 75, No. 2, pp. 185-194 (1994).
Lee et al., "Separation of reduced disaccharides derived from glycosaminoglycans by high-performance liquid chromatography", J. of Chromatography, 1981, vol. 212, pp. 65-73.
Li et al., "Linkage analysis of chromophore-labeled disaccharides and linear oligosaccharides by negative ion fast atom bombardment ionization and collisonal-induced dissociation with B/E scanning", Analyt. Biochem., 1993, vol. 211, No. 2, pp. 250-257.
Lin et al., "Heparan sulfate proteoglycans are essential for FGF receptor signaling during *Drosophila* embryonic development", Development, 1999, vol. 126, pp. 3715-3723.
Lindahl et al., "Common binding sites for b-amyloid fibrils and fibroblast growth factor-2 in heparan sulfate from human cerebral cortex", J. Biol. Chem., 1999, vol. 274, pp. 30631-30635.
Lindhart et al., "Mapping and quantification of the major oligosaccharide components of heparin", Biochem. Journal, 1988, vol. 254, pp. 781-787.
Lindhart et al., "New methodologies in heparin structure analysis and the genereation of LMW heparins", Heparin and Related Polysaccharides, 1992, pp. 37-47, ed. D.A. Lane et al., Plenum Press, New York.
Lindhart et al., "Oligosaccharide mapping of low molecular weight heparins: structure and activity differences", J. of Medicinal Chem., 1990, vol. 33, No. 6, pp. 1639-1645.
Liotta et al., "Cancer metastasis and angiogenesis: an imbalance of positive and negative regulation", Cell, 1991, vol. 64, pp. 327-336.
Liu et al., "A heparin-binding synthetic peptide of heparin/heparan sulfate-interacting protein modulates blood coagulation activities", PNAS, 1997, vol. 94, pp. 1739-1744.
Liu et al., "Strategy for the sequence analysis of heparin", Glycobiology, 1995, vol. 5, pp. 765-774.
Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage", J. Exp. Med., 1998, vol. 188, pp. 1005-1016.
Malsch et al., "High-resolution capillary electrophoresis and polyacrylamide gel electrophoresis of heparins," Journal of Chromatography A, 1995, vol. 716, pp. 258-268.
Mandruzzato et al., "A CASP-8 mutation recognized by cytolytic T lymphocytes on a human head and neck carcinoma", J. Exp. Med., 1997, vol. 186, pp. 785-793.
Manici et al., "Melanoma cells present a MAGE-3 epitope to CD4(+) cytotoxic T cells in association with histocompatibility leukocyte antigen DR11", J. Exp. Med., 1999, vol. 189, pp. 871-876.
Mascellani et al., "Characterization of di- and monosulfated, unsaturated heparin disaccharides with terminal N-sulfated 1,6-anhydro-b-D-glucosamine or N-sulfated 1,6-anydro-b-D-mannosamine residues", Carbohydrate Research, 2007, vol. 342, pp. 835-842.
Mauray et al., "Mechanism of factor IXa inhibition by antithrombin in the presence of unfractionated and low molecular weight heparins and fucoidan", Biochim. Biophys. Acta, vol. 1387, No. 1-2, pp. 184-194, (1998).
McLaurin et al., "Interactions of Alzheimer amyloid-b peptides with glycosaminoglycans effects on fibril nucleation and growth", Eur. J. Biochem., 1999, vol. 266, pp. 1101-1110.
Merchant et al., "Structure of heparin-derived tetrasaccharides", Biochem. Journal, 1985, vol. 229, pp. 369-377.
Merry et al., "Highly sensitive sequencing of the sulfated domains of heparan sulfate", J. Biol. Chem., 1999, vol. 274, pp. 18455-18462.
Militsopoulou et al., "Determination of twelve heparin- and heparan sulfate-derived disaccharides as 2-aminoacridone derivatives by capillary zone electrophoresis using ultrviolet and laser-induced flourescence detection", Electrophoresis, 2002, vol. 23, pp. 1104-1109.
Morel et al., "A tyrosinase peptide presented by HLA-B35 is recognized on a human melanoma by autologous cytotoxic T lymphocytes", Int. J. Cancer, 1999, vol. 83, pp. 755-759.
Morell et al., "Analysis of starch structure using fluorophore-assisted carbohydrate electrophoresis", Electrophoresis, 1998, vol. 19, No. 15, pp. 2603-2611.
Oiso et al., "A newly identified MAGE-3-derived epitope recognized by HLA-A24-restricted cytotoxic T lymphocytes", Int. J. Cancer, 1999, vol. 81, pp. 387-394.
Parish et al., "A basement-membrane permeability assay which correlates with the metastatic potential of tumour cells", Int. J. Cancer, 1992, vol. 52, pp. 378-383.
Park et al., "Purification and characterization of heparin sulphate proteoglycan from bovine brain", Biochem. Journal, 1999, vol. 344, pp. 723-730.
Parkhurst et al., "Identification of a shared HLA-A*0201-restricted T-cell epitope from the melanoma antigen tyrosinase-related protein 2 (TRP2)", Cancer Research, 1998, vol. 58, pp. 4895-4901.
Perlin et al., "Spectroscopic methods", The Polysaccharides, 1982, vol. 1, pp. 133-193, Edited by G.O., Academic Press.
Pervin et al., "Separation of glycosaminoglycan-derived oligosaccharides by capillary electrophoresis using reverse polarity", Analytical Biochem., 1994, vol. 221, pp. 182-188.
Petitou et al., "Synthetic oligosaccharides having various functional domains: potent and potentially safe heparin mimetics", Bioorg. Med. Chem. Lett., 1999, vol. 9, No. 8, pp. 1161-1166.

(56) References Cited

OTHER PUBLICATIONS

Piani et al., "Alkali-induced optical rotation changes in heparins and heparan sulfates, and their relation to iduronic acid-containing sequences", Journal of Carbohydrate Chemistry, 1993, vol. 12, No. 4&5, pp. 507-521.
Pieper et al., "Biochemical identification of a mutated human melanoma antigen recognized by CD4(+) T cells", J. Exp. Med., 1999, vol. 189, pp. 757-765.
Plaintiffs' Answer to Defendants' Counterclaims—*Momenta Pharmaceuticals, Inc. and Sandoz, Inc.*, Plaintiffs, v. *Amphastar Pharmaceuticals, Inc., International Medication Systems, Ltd., Watson Pharmaceuticals, Inc., and Watson Pharma, Inc.*, Defendants. 2012 WL 4060946.
Plaintiffs' Claim Construction Memorandum U.S. Patent No. 7,575,886 *Momenta Pharmaceuticals, Inc. and Sandoz Inc.*, Plaintiffs, v. *Teva Pharmaceuticals USA, Inc.*, Defendant. *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012WL 2455758.
Plaintiffs' Claim Construction Memorandum U.S. Patent No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150688.
Plaintiffs' Claim Contruction Memorandum U.S. Patent No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150798.
Plaintiffs' Claim Construction Memorandum U.S. Patent No. 7,790,466 *Momenta Pharmaceuticals, Inc. and Sandoz Inc.*, Plaintiffs, v. *Teva Pharmaceuticals USA, Inc.*, Defendant. *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 2455750.
Plaintiffs' Claim Construction Memorandum U.S. Patent No. 7,790,466 *Momenta Pharmaceuticals, Inc. and Sandoz Inc.*, Plaintiffs, v. *Teva Pharmaceuticals USA, Inc*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150684.
Plaintiffs' Reply to the Defendants' Claim Construction Memoranda Regarding U.S. Patent No. 7,790,466 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150797.
Pojasek, et al., "Histidine 295 and histidine 510 are crucial for the enzymatic degradation of heparan sulfate by heparinase III", Biochemistry, 2000, vol. 39, pp. 4012-4019.
Desai et al., "Oligosaccharide composition of heparin and low-molecular-weight heparin by capillary electrophoresis", Analytical Biochem., 1993, vol. 213, pp. 120-127.
Desai et al., "Molecular weight of low molecular weight heparins by 13C nuclear magnetic resonance spectroscopy", Carbohydrate Research, 1994, vol. 255, pp. 193-212.
Docket 1:10cv12079—*Momenta Pharmaceuticals, Inc. et al v. Teva Pharmaceuticals Industries Ltd. et al.*
Docket 1:11cv11681—*Momenta Pharmaceuticals, Inc. et al v. Amphastar Pharmaceuticals, Inc. et al.*

Drummond et al., "Electrophoretic sequencing of heparin/heparan sulfate oligosaccharides using a highly sensitive fluorescent end label", Proteomics, 2001, vol. 1, No. 2, pp. 304-310.
Duffour et al., "A MAGE-A4 peptide presented by HLA-A2 is recognized by cytolytic T lymphocytes", Eur. J. Immunol., 1999, vol. 29, pp. 3329-3337.
Ernst et al., "Direct evidence for a predominantly exolytic processive mechanism for depolymerization of heparin-like glycosaminoglycans by heparinase I", PNAS USA, 1998, vol. 95, pp. 4182-4187.
Ernst et al., "Expression in *Escherichia coli*, purification and characterization of heparinase I from Flavobacterium heparinum", Biochem. J., 1996, vol. 315, pp. 589-597.
European Search Report from European Application Serial No. 10190250.0 dated Dec. 27, 2010.
Fareed et al., "Generic low-molecular-weight heparins: some practical considerations" Seminars in Thrombosis and Hemostasis, 2004, vol. 30, No. 6, pp. 703-713.
Fareed et al., "Biochemical and pharmacologic heterogeneity in low molecular weight heparins. Impact on the therapeutic profile", Current Pharmaceutical Design, 2004, vol. 10, pp. 983-999.
Harenberg et al., "Overview on guidelines and recommendations for generic low-molecular-weight heparins", Thrombosis Research, vol. 127, S100-S104 (2011).
International Search Report and Written Opinion from International Application Serial No. PCT/US11/21582 mailed Mar. 21, 2011.
International Search Report and Written Opinion from International Application Serial No. PCT/US2009/055792 mailed Feb. 12, 2009.
Lou et al., "Structural Specificity in a FGF7-Affinity Purified Heparin Octasaccharide Required for Formation of a Complex with FGF7 and FGFR2IIIb" Journal of Cellular Biochemistry, vol. 97, pp. 1241-1258 (2006).
Rice et al., "Gradient page and strong anion exchange Sax Hplc as analytical tools for sequencing the heparin polymer", American Chemical Society, 1987, vol. 193, pp. 1, Abstracts of paper from the National Meeting.
Rota et al., "Free radical generation during chemical depolymerization of heparin", Analytical Biochemistry, vol. 344, pp. 193-203 (2005).
Supplemental Partial European Search Report from European Application No. EP 037446289 dated Jul. 14, 2008.
Razi et al., "Structural and functional properties of heparin analogues obtained by chemical sulphation of *Escherichia coli* K5 capsular polysaccharide", Biochem. J., vol. 309, No. 2, pp. 465-475, (1995).
Reply Brief for Appellants, *Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals, Inc., and Watson Pharma, Inc.*, Defendants-Appellants. 2011 WL 7039088.
Reply Brief for Petitioners—*Momenta Pharmaceuticals, Inc. v. Amphastar Pharmaceuticals, Inc.* 2013 WL 2428972.
Rhomberg et al., "Mass spectrometric and capillary electrophoretic investigation of the enzymatic degradation of heparin-like glycosaminoglycans", PNAS, 1998, vol. 95, pp. 4167-4181.
Rhomburg et al., "Mass spectrometric evidence for the enzymatic mechanism of the depolymerization of heparin-like glycosaminoglycans by heparinase II", PNAS USA, 1998, vol. 95, pp. 12232-12237.
Rice et al., "High-performance liquid chromatographic separation of heparin-derived oligosaccharides", Analytical Biochem., 1985, vol. 150, No. 2, pp. 325-331.
Robbins et al., "A mutated b-catenin gene encodes a melanoma-specific antigen recognized by tumor infiltrating lymphocytes", J. Exp. Med., 1996, vol. 183, pp. 1185-1192.
Robbins et al., "The intronic region of an incompletely spliced gp100 gene transcript encodes an epitope recognized by melanoma-reactive tumor-infiltrating lymphocytes", J. Immunol., 1997, vol. 159, pp. 303-308.
Ronsin et al., "A non-AUG-defined alternative open reading frame of the intestinal carboxyl esterase mRNA generates an epitope recognized by renal cell carcinoma-reactive tumor-infiltrating lymphocytes in situ", J. Immunol., 1999, vol. 163, pp. 483-490.

(56) References Cited

OTHER PUBLICATIONS

Ruiz-Calero et al., "Pressure-assisted capillary electrophoresis-electrospray ion trap mass spectrometry for the analysis of heparin depolymerised disaccharides", J. of Chromatogrphy A, 2001, vol. 914, pp. 277-291.

Ruiz-Calero et al., "Use of reversed polarity and pressure gradient in the analysis of disaccharide composition of heparin by capillary electrophoresis", J. of Chromatography A, 1998, vol. 828, pp. 497-508.

Röpke et al., "Spontaneous human squamous cell carcinomas are killed by a human cytotoxic T lymphocyte clone recognizing a wild-type p53-derived peptide", Proc. Natl. Acad. Sci. USA, 1996, vol. 93, pp. 14704-14707.

Saad et al., "Compositional analysis and quantification of heparin and heparan sulfate by electrospray ionization ion trap mass spectrometry", Anal. Chem., 2003, vol. 75, pp. 2985-2995.

Sasisekharan et al. "Heparinase inhibits neovascularization", Proc. Natl. Acad. Sci. USA, 1994, vol. 91, pp. 1524-1528.

Scapol et al., "Capillary electrophoresis of heparin and dermatan sulfate unsaturated disaccharides with triethylamine and acetonitrile as electrolyte additives", J. of Chromatography A, 1996, vol. 735, pp. 367-374.

Schanda, "Very fast two-dimensional NMR spectroscopy for real-time investigation of dynamic events in proteins on the time scale of seconds", Journal of the American Chemical Society, 2005, vol. 127, pp. 8014-8015.

Schneider et al., "Overlapping peptides of melanocyte differentiation antigen Melan-A/MART-1 recognized by autologous cytolytic T lymphocytes in association with HLA-B45.1 and HLA-A2.1", Int. J. Cancer, 1998, vol. 75, pp. 451-458.

Shriver et al., "Cleavage of the antithrombin III binding site in heparin by heparinases and its implication in the generation of low molecular weight heparin", PNAS, 2000, vol. 97, No. 19, pp. 10365-10370.

Shriver et al., "Sequencing of 3-0 sulfate containing heparin decasaccharides with a partial antithrombin III binding site", PNAS, 2000, vol. 97, No. 19, pp. 10359-10364.

Skipper et al., "An HLA-A2-restricted tyrosinase antigen on melanoma cells results from posttranslational modification and suggests a novel pathway for processing of membrane proteins", J. Exp. Med., 1996, vol. 183, pp. 527-534.

Skipper et al., "Shared epitopes for HLA-A3-restricted melanoma-reactive human CTL include a naturally processed epitope from Pmel-17/gp100", J. Immunol., 1996, vol. 157, pp. 5027-5033.

Sudor et al., "End-label free-solution electrophoresis of the low molecular weight heparins", Anal. Chem., 1997, vol. 69, No. 16, pp. 3199-3204.

Sundaram et al., "Rational design of low-molecular weight heparins with improved in vivo activity," PNAS, Jan. 21, 2003, vol. 100, No. 2, pp. 651-656.

Tahara et al., "Identification of a MAGE-2-encoded human leukocyte antigen-A24-binding synthetic peptide that induces specific antitumor cytotoxic T lymphocytes", Clin. Cancer Res., 1999, vol. 5, pp. 2236-2241.

Tanaka et al., "Induction of antitumor cytotoxic T lymphocytes with a MAGE-3-encoded synthetic peptide presented by human leukocytes antigen-A24", Cancer Res., 1997, vol. 57, pp. 4465-4468.

Tanzarella et al., "Identification of a promiscuous T-cell epitope encoded by multiple members of the MAGE family", Cancer Res., 1999, vol. 59, pp. 2668-2674.

Thanawiroon et al., "Liquid chromatography/mass spectrometry sequencing approach for highly sulfated heparin-derived oligosaccharides", J. of Biological Chem., 2004, vol. 279, No. 4, pp. 2608-2615.

Thanawiroon et al., "Separation of a complex mixture of heparin-derived oligosaccharides using reversed-phase high-performance liquid chromatography", J. of Chromatography A, 2003, vol. 1014, pp. 215-223.

Toida et al., "Structural differences and the presence of unsubstituted amino groups in heparan sulphates from different tissues and species", Biochem. Journal, 1997, vol. 322, pp. 499-506.

Topalian et al., "Melanoma-specific CD4+ T cells recognize nonmutated HLA-DR-restricted tyrosinase epitopes", J. Exp. Med., 1996, vol. 183, pp. 1965-1971.

Toyoda et al., "Rapid and sensitive analysis of disaccharide composition in heparin and heparan sulfate by reversed-phase ion-pair chromatography on a 2 mm porous silica gel column", J. of Chromatography A, 1999, vol. 830, pp. 197-201.

Traversari et al., "A nonapeptide encoded by human gene MAGE-1 is recognized on HLA-A1 by cytolytic T lymphocytes directed against tumor antigen MZ2-E", J. Exp. Med., 1992, vol. 176, pp. 1453-1457.

Trehy et al., "Analysis of heparin sodium by SAX/HPLC for contaminants and impurities", Journal of Pharmaceutical and Biomedical Analysis, 2009, vol. 49, No. 3, pp. 671-673.

Tsai et al., "Identification of subdominant CTL epitopes of the GP100 melanoma-associated tumor antigen by primary in vitro immunization with peptide-pulsed dendritic cells", J. Immunol., 1997, vol. 158, pp. 1796-1802.

Tsang et al., "Generation of human cytotoxic T cells specific for human carcinoembryonic antigen epitopes from patients immunized with recombinant vaccinia-CEA vaccine", J. Natl. Cancer Inst., 1995, vol. 87, pp. 982-990.

Tsuda et al., "The cell-surface proteoglycan Daily regulates Wingless signalling in *Drosophila*", Nature, 1999, vol. 400, pp. 276-280.

Turnbull et al., "A strategy for rapid sequencing of heparan sulfate and heparin saccharides", Proc. Natl. Acad. Sci. USA, 1999, vol. 96, pp. 2698-2703.

Turnbull et al., "Analytical and preparative strong anion-exchange HPLC of heparan sulfate and heparin saccharides" Methods in Molecular Biology, vol. 171, pp. 141-147 (2001).

Van Den Eynde et al., "A new family of genes coding for an antigen recognized by autologous cytolytic T lymphocytes on a human melanoma", J. Exp. Med., 1995, vol. 182, pp. 689-698.

Van Der Bruggen et al., "A peptide encoded by human gene MAGE-3 and presented by HLA-A2 induces cytolytic T lymphocytes that recognize tumor cells expressing MAGE-3", Eur. J. Immunol., 1994, vol. 24, pp. 3038-3043.

Van Der Bruggen et al., "Autologous cytolytic T lymphocytes recognize a MAGE-1 nonapeptide on melanomas expressing HLA-Cw*1601", Eur. J. Immunol., vol. 24, pp. 2134-2140, (1994).

Van Putten et al., Determination of low molecular weight heparin in clinical laboratory, Haemostasis, 1984, vol. 14, pp. 205-210.

Venkataraman et al., "Sequencing complex polysaccharides", Science, 1999, vol. 286, pp. 537-542.

Volpi et al., "Characterization of heparins with different relative molecular masses (from 11 600 to 1600) by various analytical techniques", J. of Chromatography, 1993, vol. 622, pp. 13-20.

Volpi et al., "Hyaluronic acid and chondroitin sulfate unsaturated disaccharides analysis by high-performance liquid chromatography and fluorimetric detection with dansylhydrazine", Analytical Biochem., 2002, vol. 277, pp. 19-24.

Vonderheide et al., "The telomerase catalytic subunit is a widely expressed tumor-associated antigen recognized by cytotoxic T lymphocytes", Immunity, 1999, vol. 10, pp. 673-679.

Vynios et al., "Advances in analysis of glycosaminoglycans: its applications for the assessment of physiological and pathological states of connective tissues", J. of Chromatography B, 2002, vol. 781, pp. 21-38.

Fisk et al., "Identification of immunodominant peptide of HER-2/neu protooncogene recognized by ovarian tumor-specific cytotoxic T lymphocyte lines", J. Exp. Med., 1995, vol. 181, pp. 2109-2117.

Franz et al., "MALDI-FTMS characterization of oligosaccharides labeled with 9-aminofluorene", J. Am. Soc. Mass Spectrom., 2001, vol. 12, No. 12, pp. 1254-1261.

Fujie et al., "A MAGE-1-encoded HLA-A24-binding synthetic peptide induces specific anti-tumor cytotoxic T lymphocytes", Int. J. Cancer, 1999, vol. 80, pp. 169-172.

Gaudin et al., "A hsp70-2 mutation recognized by CTL on a human renal cell carcinoma", J. Immunol., 1999, vol. 162, pp. 1730-1738.

(56) References Cited

OTHER PUBLICATIONS

Gaugler et al., "Human gene MAGE-3 codes for an antigen recognized on a melanoma by autologous cytolytic T lymphocytes", J. Exp. Med., 1994, vol. 179, pp. 921-930.

Gjertsen et al., "Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation", Int. J. Cancer, 1997, vol. 72, pp. 784-790.

Guerrini et al., "Combined quantitative 1H and 13C nuclear magnetic resonance spectroscopy for characterization of heparin preparations", Seminars in Thrombosis and Hemostasis, 2001, vol. 27, No. 5, pp. 473-482.

Guerrini et al., "Complex glycosaminoglycans: profiling substitution patterns by two-dimensional nuclear magnetic resonance spectroscopy", Analytical Biochemistry, 2005, vol. 337, pp. 35-47.

Guerrini et al., "Low molecular weight heparins: structural differentiation by bidimensional nuclear magnetic resonance spectroscopy", Seminars in Thrombosis and Hemostasis, 2007, vol. 33, No. 5, pp. 478-487.

Guerrini et al., "Oversulfated chondroitin sulfate is a contaminant in heparin associated with adverse clinical events", Nature Biotechnology, Jun. 2008, vol. 26, No. 6, pp. 669-675, Nature Publishing Group US.

Guilloux et al., "A peptide recognized by human cytolytic T lymphocytes on HLA-A2 melanomas is encoded by an intron sequence of the N-acetylglucosaminyltransferase V gene", J. Exp. Med., 1996, vol. 183, pp. 1173-1183.

Guizzardi et al., "Pharmacokinetics and organ distribution in rats of a low molecular weight heparin", Arzneimittel-Forschung, 1987, vol. 37, No. 11, pp. 1281-1283.

Guo et al., "The disaccharide composition of heparins and heparan sulfates", Analytical Biochem., 1989, vol. 176, pp. 96-104.

Guéguen et al., "An antigen recognized by autologous CTLs on a human bladder carcinoma", J. Immunol., 1998, vol. 160, pp. 6188-6194.

Hennekens et al., "Current issues concerning thrombolytic therapy of acute myocardial infarction", J. Am. Coll. Cardiol., 1995, vol. 25, No. 7, pp. 18S-22S.

Herman et al., "A peptide encoded by the human MAGE3 gene and presented by HLA-B44 induces cytolytic T lymphocytes that recognize tumor cells expressing MAGE3", Immunogenetics, 1996, vol. 43, pp. 377-383.

Hirano, "NMR study of 4-deoxy-a-L-threo-4-enohexopyranosyluronic acid (1® 3)2-acetamido-2-deoxy-D-hexoses produced in the enzymic digestion of hyaluronate, chondroitin and chondroitin sulfates", Organic Magnetic Resonance, vol. 2, pp. 577-580, (1970).

Hogan et al., "The peptide recognized by HLA-A68.2-restricted, squamous cell carcinoma of the lung-specific cytotoxic T lymphocytes is derived from a mutated elongation factor 2 gene", Cancer Res., 1998, vol. 58, pp. 5144-5150.

Holmes et al., "Lessons we have learned from the GUSTO trial", J. Am. Coll. Cardiol., 1995, vol. 25, No. 7, pp. 10S-17S.

Holzgrabe et al., "Quantitative NMR spectroscopy—Applications in drug analysis", Journal of Pharmaceutical and Biomedical Analysis, vol. 38, pp. 806-812, (2005).

Hricovini et al., "Conformational analysis of heparin epoxide in aqueous solution. An NMR relaxation study", Carbohydrate Research, 1995, vol. 277, pp. 11-23.

Huang et al., "Cytolytic T lymphocytes recognize an antigen encoded by MAGE-A10 on a human melanoma", J. Immunol., 1999, vol. 162, pp. 6849-6854.

Ikeda et al., "Characterization of an antigen that is recognized on a melanoma showing partial HLA loss by CTL expressing an NK inhibitory receptor", Immunity, 1997, vol. 6, pp. 199-208.

Imai et al., "Directional degradation of b-chitin by chitinase A1 revealed by a novel reducing end labelling technique", FEBS Lett, 2002, vol. 510, No. 3, pp. 201-205.

Imanari et al., "High-performance liquid chromatographic analysis of glycosaminglycan-derived oligosaccharides", J. of Chomatography A, 1996, vol. 720, pp. 275-293.

International Search Report from International Application Serial No. PCT/US03/07208 dated Nov. 16, 2004.

Jeske et al., "Pharmacologic profile of certoparin", Exp. Opin. Invest. Drugs, 1999, vol. 8, No. 3, pp. 315-327.

Jäger et al., "Simultaneous humoral and cellular immune response against cancer-testis antigen NY-ESO-1: definition of human histocompatibility leukocyte antigen (HLA)-A2-binding peptide epitopes", J. Exp. Med., 1998, vol. 187, pp. 265-270.

Kang et al., "Identification of a tyrosinase epitope recognized by HLA-A24-restricted, tumor-infiltrating lymphocytes", J. Immunol., 1995, vol. 155, pp. 1343-1348.

Karamanos et al., "Ion-pair high-performance liquid chromatography for determining disaccharide composition in heparin and heparan sulphate", J. of Chromatography, 1997, vol. 765, pp. 169-179.

Kariya et al., "Disaccharide analysis of heparin and heparan sulfate using deaminative cleavage with nitrous acid and subsequent labeling with paranitrophenyl hydrazine", J. Biochem., 1998, vol. 123, No. 2, pp. 240-246, Tokyo.

Kawakami et al., "Identification of a human melanoma antigen recognized by tumor-infiltrating lymphocytes associated with in vivo tumor rejection", Proc. Natl. Acad. Sci. USA, 1994, vol. 91, pp. 6458-6462.

Kawakami et al., "Identification of new melanoma epitopes on melanosomal proteins recognized by tumor infiltrating T lymphocytes restricted by HLA-A1, -A2, and -A3 alleles", J. Immunol., 1998, vol. 161, pp. 6985-6992.

Kawakami et al., "Identification of the immunodominant peptides of the MART-1 human melanoma antigen recognized by the majority of HLA-A2-restricted tumor infiltrating lymphocytes", J. Exp. Med., 1994, vol. 180, pp. 347-352.

Kawakami et al., "Recognition of multiple epitopes in the human melanoma antigen gp100 by tumor-infiltrating T lymphocytes associated with in vivo tumor regression", J. Immunol., 1995, vol. 154, pp. 3961-3968.

Kawashima et al., "The multi-epitope approach for immunotherapy for cancer: identification of several CTL epitopes from various tumor-associated antigens expressed on solid epithelial tumors", Hum. Immunol., 1998, vol. 59, pp. 1-14.

ANALYSIS OF SULFATED POLYSACCHARIDES

CLAIM OF PRIORITY

This application is a continuation of U.S. Ser. No. 13/602,979, filed Sep. 4, 2012, now abandoned, which is a continuation of U.S. Ser. No. 13/086,054, filed Apr. 13, 2011, now abandoned, which is a continuation of U.S. Ser. No. 12/203,629, filed Sep. 3, 2008, now U.S. Pat. No. 7,947,507, which is a continuation of U.S. Ser. No. 10/386,402, filed Mar. 11, 2003, now U.S. Pat. No. 7,575,886, which claims priority under USC §119(e) to U.S. Provisional Patent Application Ser. No. 60/393,973, filed on Jul. 5, 2002, U.S. Provisional Patent Application Ser. No. 60/383,903, filed on May 28, 2002, and U.S. Provisional Patent Application Ser. No. 60/363,240, filed on Mar. 11, 2002, the entire contents of which are hereby incorporated by reference.

FIELD OF THE INVENTION

The invention relates to methods and products associated with analyzing and monitoring heterogeneous populations of sulfated polysaccharides. In particular, therapeutic heparin products including low molecular weight heparin products and methods of analyzing and monitoring these products are described.

BACKGROUND OF THE INVENTION

Coagulation is a physiological pathway involved in maintaining normal blood hemostasis in mammals. Under conditions in which a vascular injury occurs, the coagulation pathway is stimulated to form a blood clot to prevent the loss of blood. Immediately after the vascular injury occurs, blood platelets begin to aggregate at the site of injury forming a physical plug to stop the leakage. In addition, the injured vessel undergoes vasoconstriction to reduce the blood flow to the area and fibrin begins to aggregate forming an insoluble network or clot, which covers the ruptured area.

When an imbalance in the coagulation pathway shifts towards excessive coagulation, the result is the development of thrombotic tendencies, which are often manifested as heart attacks, strokes, deep vein thrombosis, myocardial infarcts, unstable angina and acute coronary syndromes. Furthermore, an embolism can break off from a thrombus and result in a pulmonary embolism or cerebral vascular embolism including stroke or transient ischemia attack. Current therapies for treating disorders associated with imbalances in the coagulation pathway involve many risks and must be carefully controlled.

Heparin and low molecular weight heparins (LMWHs), complex, sulfated polysaccharides isolated from endogenous sources, are potent modulators of hemostasis. Heparin, a highly sulfated heparin-like glycosaminoglycan (HLGAG) produced by mast cells, is a widely used clinical anticoagulant, and is one of the first biopolymeric drugs and one of the few carbohydrate drugs. Heparin and molecules derived from it are potent anticoagulants that are used in a variety of clinical situations, especially for thromboembolic disorders including the prophylaxis and treatment of deep venous thrombosis and pulmonary embolism, arterial thromboses, and acute coronary syndromes like myocardial infarction and unstable angina. Heparin and LMWHs interact with multiple components of the coagulation cascade to inhibit the clotting process. Heparin primarily elicits its effect through two mechanisms, both of which involve binding of antithrombin III (AT-III) to a specific pentasaccharide sequence, $H_{NAc/S,6S}GH_{NS,3S,6S}I_{2S}H_{NS,6S}$ contained within the polymer. First, AT-III binding to the pentasaccharide induces a conformational change in the protein that mediates its inhibition of factor Xa. Second, thrombin (factor IIa) also binds to heparin at a site proximate to the pentasaccharide/AT-III binding site. Formation of a ternary complex between AT-III, thrombin and heparin results in inactivation of thrombin. Unlike its anti-Xa activity that requires only the AT-III pentasaccharide-binding site, heparin's anti-IIa activity is size-dependent, requiring 1-13 saccharide units in addition to the pentasaccharide unit responsible for anti-Xa activity for the efficient formation of an AT-III, thrombin, and heparin ternary complex. Heparin also mediates the release of tissue factor pathway inhibitor (TFPI) from endothelial cells. TFPI, a heparin cofactor, is a serine protease that directly binds to and inhibits factor X. TFPI is a potent anti-thrombotic, particularly when co-administered with heparin.

In addition to heparin's anticoagulant properties, its complexity and wide distribution in mammals have lead to the suggestion that it may also be involved in a wide range of additional biological activities. Heparin-like glycosaminoglycans, present both at the cell surface and in the extracellular matrix, are a group of complex polysaccharides that are variable in length, consisting of a disaccharide repeat unit composed of glucosamine and an uronic acid (either iduronic or glucuronic acid). The high degree of complexity for HLGAGs arises not only from their polydispersity and the possibility of two different uronic acid components, but also from differential modification at four positions of the disaccharide unit. Three positions, viz., C2 of the uronic acid and the C3, C6 positions of the glucosamine can be O-sulfated. In addition, C2 of the glucosamine can be N-acetylated or N-sulfated. Together, these modifications could theoretically lead to 32 possible disaccharide units, making HLGAGs potentially more information dense than either DNA (4 bases) or proteins (20 amino acids). This enormity of possible structural variants allows HLGAGs to be involved in a large number of diverse biological processes, including angiogenesis (Sasisckharan, R., Moses, M. A., Nugent, M. A., Cooney, C. L. & Langer, R. (1994) Proc Natl Acad Sci USA 91, 1524-8, embryogenesis (Binari, R. C., Staveley, B. E., Johnson, W. A., Godavarti, R., Sasisekharan, R. & Manoukian, A. S. (1997) Development 124, 2623-32; Tsuda, M., Kamimura, K., Nakato, H., Archer, M., Staatz, W., Fox, B., Humphrey, M., Olson, S., Futch, T., Kaluza, V., Siegfried. B., Stam, L. & Selleck, S. B. (1999) Nature 400, 276-80; and Lin, X., Buff, E. M., Perrimon, N. & Michelson, A. M. (1999) Development 126, 3715-23) and the formation of β-fibrils in Alzheimer's disease (McLaurin, J., Franklin, T., Zhang, X., Deng, J. & Fraser, P. E. (1999) Eur J Biochem 266, 1101-10. And Lindahl, B., Westling, C., Gimenez-Gallego, G., Lindahl, U. & Salmivirta, M. (1999) J Biol Chem 274, 30631-5).

Although heparin is highly efficacious in a variety of clinical situations and has the potential to be used in many others, the side effects associated with heparin therapy are many and varied. Anti-coagulation has been the primary clinical application for unfractionated heparin (UFH) for over 65 years. Due to its erratic pharmacokinetics following s.c. administration, UFH has been administered by intravenous injection instead. Additionally, the application of UFH as an anticoagulant has been hampered by the many side effects associated with non-specific plasma protein binding with UFH.

Side effects such as heparin-induced thrombocytopenia (HIT) are primarily associated with the long chain of UFH, which provides binding domains for various proteins. HIT is an immune-mediated thrombocytopenia which is the result of antibodies, usually IgG, directed against heparin-platelet factor 4 (PF4) complexes. Injected heparin binds with normally occurring low levels of PF4 in plasma to form a macromolecular complex that binds to the surface of platelets. In some patients, antibodies are produced against the heparin/PF4 complex. When present, these antibodies bind to the heparin/PF4 complex on the surface of platelets and crosslink Fc receptors on the platelet surface thereby causing platelet activation. Platelet activation releases procoagulants including additional PF4. Release of the latter in the presence of heparin further increases platelet activation. The activated platelets either join in forming a clot or are removed by the spleen. Platelet activation ceases when heparin is removed, however, the antibody usually remains detectable for four to six weeks.

Clinically, patients with HIT typically present with a decrease in platelet count, generally five to eleven days after initiated of heparin therapy. Platelet counts drop by up to 50%, to levels usually between 20 and 150 (×103/mm3). This thrombocytopenia is associated with thrombosis rather than purpura or bleeding; deep vein thromboses and pulmonary emboli are the most common complication. Arterial thrombosis occurs less often and usually involves large limb vessels, cerebral arteries, and visceral arteries. It has been estimated that 20% of patients receiving heparin therapy develop heparin induced platelet antibodies, 3% have a drop in platelet count, and 1% or less experience thrombotic complications. Other reported manifestations of heparin-induced thrombocytopenia include localized skin lesions with subcutaneous heparin administration, acute systemic reactions resembling febrile transfusion reactions, and transient global amnesia.

Other side effects include intracranial hemorrhage, bleeding, internal/external hemorrhage, hepatic enzyme (AST and ALT) level elevation, and derma lesion at the site of injection. This has led to the explosion in the generation and utilisation of low molecular weight heparin (LMWH) as an efficacious alternative to UFH. Although attention has been focused on LMWH as heparin substitutes due to their more predictable pharmacological action, reduced side effects, sustained antithrombotic activity, and better bioavailability, there is at present no means of correlating their activity with a particular structure or structural motif due to the structural heterogeneity of heparin and LMWH, as it has been technically unfeasible to determine their structures, and there has been no reliable and readily available means for monitoring LMWH levels in a subject. And since all of the commercially available LMWH preparations are not fully neutralized by protamine, an unexpected reaction could have extremely adverse effects; the anti-Xa activity of enoxaparin and other LMWH are neutralizable only to an extent of about 40% with ≤2 mg Protamine/100 IU anti-Xa LMWH. The anti-IIa activity is neutralizable only to an extent of about 60% with ≤2 mg Protamine/100 IU anti-Xa LMWH. (On the other hand, the anti-Xa and anti-IIa activity of UFH is neutralizable almost completely (>90%) with ≤2 mg Protamine sulfate/100 IU anti-Xa UFH.)

Pharmaceutical preparations of these polysaccharides, typically isolated from porcine intestinal mucosa, are heterogeneous in length and composition. As such, only a portion of a typical preparation possesses anticoagulant activity. At best, the majority of the polysaccharide chains in a pharmaceutical preparation of heparin or LMWH are inactive, at worst, these chains interact nonspecifically with plasma proteins to elicit the side effects associated with heparin therapy. Therefore, it is important to develop novel LMWHs that retain the anticoagulant activity and other desired activities of UFH but have reduced side effects. LMWHs, essentially due to their reduced chains sizes and dispersity, display markedly less non-specific plasma protein binding. However, all LMWHs that are currently clinically available also possess reduced anti-IIa activity as compared to UFH. Because of this decreased activity, a larger dose of LMWH is required (compared to UFH) in order to achieve a similar anti-coagulant activity, and the standard tests for UFH activity, activated partial thromboplastin time (aPTT) or thrombin clotting times (TCT), are not useful as they rely primarily on anti-IIa activity for a readout. The most widely used test for monitoring LMWH levels is an anti-Xa activity test, which depends on the subject having sufficient levels of antithrombin III (ATIII), which is not always the case. This test is quite costly (well over $100.00) and is not routine or readily available, as samples generally must be sent to an outside lab for analysis. Consequently, the use of LMWHs so far has been largely limited to the prevention of thrombosis and not to their treatment, and the population of patients to whom it can be administered has been limited, excluding, among others, pediatric patients, patients with abnormal renal function as measured by RFI, urea, creatinine, phosphorus, glomerular filtration rate (GFR), or BUN (Blood Urea Nitrogen level) in blood and urine and the interventional cardiology patient population. Improved monitoring methods are necessary to provide the advantages of LMWHs to a wider population of patients without increasing the risk of undesired effects. In addition, improved monitoring could allow for courses of therapy tailored to the patients condition throughout the course of their illness, for instance drug preparations given to the patient before a clot has been formed could differ from drug preparations given to the patient shortly after a clot has formed or a longer period of time after a clot has formed.

Although to a lesser degree than UFH, LMWHs are polydisperse and microhetero-geneous, with undefined structure, and thus possess inherent variability. Current methods of LMWH preparation lack standardization and result in preparations that may vary substantially from batch to batch in composition and in efficacy.

In an attempt to characterize the molecular, structural, and activity variations of heparin, several techniques have been investigated for the analysis of heparin preparations. Gradient polyacrylamide gel electrophoresis (PAGE) and strong ion exchange HPLC (SAX) have been used for the qualitative and quantitative analysis of heparin preparations. Although the gradient PAGE method can be useful in determining molecular weight, it suffers from a lack of resolution, particularly the lack of resolution of different oligosaccharides having identical size. SAX-HPLC, which relies on detection by ultraviolet absorbance, is often insufficiently sensitive for detecting small amounts of structurally important heparin-derived oligosaccharides. As current technologies for analyzing heparins and other glycosaminoglycans are insufficient, it has been heretofore impossible to create LMWH preparations with any degree of batch-batch consistency, or to predict the potency of a given batch.

SUMMARY OF THE INVENTION

The invention is based in part on the discovery of methods for analyzing heterogeneous populations of sulfated polysaccharides, e.g., heparin, e.g. UFH, LMWH, and synthetic heparins, and methods of producing sulfated polysaccharides having desired properties, e.g., desired activities and/or reduced undesired properties, e.g., undesired side effects. Thus, the invention relates to methods and products associated with analyzing and monitoring heterogeneous populations of sulfated polysaccharides, e.g., to novel methods of analyzing and thus defining the structural signature and activity of heterogeneous populations of sulfated polysaccharides.

Therapeutic heparin products including low molecular weight heparin products and methods of producing, analyzing and monitoring these products are described.

In one aspect, the invention provides a method of analyzing a sample, e.g., a composition which includes a polysaccharide. In one embodiment, the composition further comprises one or more tags, antibodies, lectins, or proteins.

A "polysaccharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). Polysaccharides include but are not limited to heparin-like glycosaminoglycans, chondroitin sulfate, hyaluronic acid and derivatives or analogs thereof, chitin in derivatives and analogs thereof, e.g., 6-0-sulfated carboxymethyl chitin, immunogenic polysaccharides isolated from phellinus linteus, PI-88 (a mixture of highly sulfated oligosaccharide derived from the sulfation of phosphomannum which is purified from the high molecular weight core produced by fermentation of the yeast pichia holstii) and its derivatives and analogs, polysaccharide antigens for vaccines, and calcium spirulan (Ca-SP, isolated from blue-green algae, spirulina platensis) and derivatives and analogs thereof.

A polysaccharide according to the invention can be a mixed population of polysaccharides, e.g., a heparin, synthetic heparin, or LMWH preparation. As used herein, a "mixed population of polysaccharides" is a polydisperse mixture of polysaccharides. The term "polydisperse" or "polydispersity" refers to the weight average molecular weight of a composition (Mw) divided by the number average molecular weight (Mn). The polydispersity of unfractionated heparin and various LMWHs are known, as are methods for determining polydispersity. Compositions with polydispersity near 1 are more homogeneous, containing fewer different polysaccharides. As an example, a preparation of unfractionated heparin, which contains a wide variety of polysaccharides of differing lengths and compositions, has a polydispersity of about 1.5 to 2.0.

In some embodiments, the sample is derived from a human or veterinary subject, an experimental animal, a cell, or any commercially available preparation of polysaccharides, e.g., UFH or LMWH, including but not limited to enoxaparin (Lovenox™); dalteparin (Fragmin™); certoparin (Sandabarin™); ardeparin (Normiflo™); nadroparin (Fraxiparin™); parnaparin (Fluxum™); reviparin (Clivarin™); tinzaparin (Innohep™ or Logiparin™), or fondaparinux (Arixtra™). In some embodiments, the human or veterinary subject is having, at risk for having, or recovering from a surgical intervention, for example, angioplasty, stent placement, cardiopulmonary bypass procedure, tissue or organ transplant, coronary revascularization surgery, orthopedic surgery, treatment for a fracture such as a hip fracture, hip replacement, knee replacement, PCI, and prosthesis replacement surgery. In some embodiments, the human or veterinary subject is a patient with abnormal renal function as measured by RFI, urea, creatinine, phosphorus, GFR or BUN levels in blood or GFR or urine. In some embodiments, the human or veterinary subject has or is at risk for having complications associated with receiving heparin or LMWH, e.g., HIT, the human or veterinary subject is overweight or obese, for example a subject who is 20, 30, 40, 50 or more pounds overweight. In some embodiments, the human or veterinary subject is extremely thin or frail, for example a subject who is 20, 30, 40, 50 or more pounds underweight, or who is suffering from an immune deficiency, e.g., HIV/AIDS. In some embodiments, the human or veterinary subject is a pediatric patient. In some embodiments, the human or veterinary subject is pregnant. In some embodiments, the human or veterinary subject is a patient having a spinal or epidural hematoma. In some embodiments, the human or veterinary subject is a patient with a prosthetic heart valve. In some embodiments, the human or veterinary subject has an ATIII deficiency or abnormality. In some embodiments, the human or veterinary subject has a factor Xa deficiency or abnormality.

In some embodiments, the method further comprises monitoring for presence, tissue distribution, spatial distribution, temporal distribution or retention time, in a cell or a subject, e.g., an experimental animal. In some embodiments, the method includes determining the structural signature of one or more batches of a product. In some embodiments, the method further includes selecting a batch as a result of the determination. In some embodiments, the method further includes comparing the results of the determination to preselected values, e.g., a reference standard.

In a preferred embodiment, the composition is digested, e.g., chemically and/or enzymatically digested, e.g., incompletely or completely digested. The enzymatic digestion is carried out with a heparin degrading enzyme, e.g., heparinase I, heparinase II, heparinase III, heparinase IV, heparanase or functionally active variants and fragments thereof. The chemical digestion is carried out with a chemical agent, e.g., oxidative depolymerization, e.g., with $H_2O_2$ or $Cu^+$ and $H_2O_2$, deaminative cleavage, e.g., with isoamyl nitrite or nitrous acid, β-eliminative cleavage, e.g., with benzyl ester, and/or by alkaline treatment.

In some embodiments, the sample includes a population of polysaccharides wherein less than or equal to 20% are <2000 Da species, greater than or equal to 68% are 2000-8000 Da species, and less than or equal to 18% are >8000 Da species, or the same as is found in commercially available enoxaparin preparations, preferably with an average molecular weight of about 4500 Da. In some embodiments, the sample has approximately 100 IU/mg anti-Xa activity. In some embodiments, the sample has a pH of 5.5-7.5. In some embodiments, one or more components of the sample is tagged or labeled.

Although the compositions are described in terms of mole %, it is well understood in the art that the compositions may also be described in terms of AUC (area under the curve) or AUC % within the scope of the invention. In some embodiments the composition chemically and/or enzymatically digested, incompletely or completely. The enzymatic digestion is carried out with a heparin degrading enzyme, e.g., heparinase I, heparinase II, heparinase III, heparinase IV, heparanase or functionally active variants and fragments thereof. The chemical digestion is carried out with a chemical agent, e.g., oxidative depolymerization, e.g., with $H_2O_2$ or $Cu^+$ and $H_2O_2$, deaminative cleavage, e.g., with isoamyl nitrite, or nitrous acid, R-eliminative cleavage, e.g., with benzyl ester, and/or by alkaline treatment. In one embodiment, the composition is a HLGAG, and analyzing the composition includes determining the presence of one or more components by optionally fractionating the HLGAG, chemically or enzymatically digesting the HLGAG, and determining the molecular weight of the digested HLGAG.

The method includes analyzing a sample comprising a polysaccharide by providing a structural signature for the polysaccharide. A structural signature, as used herein, refers to information regarding, e.g., the identity and number the mono- and di-saccharide building blocks of a polysaccharide, information regarding the physiochemical properties such as the overall charge (also referred to as the "net charge" or "total charge"), charge density, molecular size, charge to mass ratio and the presence of iduronic and/or glucuronic acid content as well as the relationships between the mono- and di-saccharide building blocks, and active sites associated with these building blocks, inter alia. The structural signature can be provided by determining one or more primary outputs chosen from the following:

the presence or the amount of one or more component saccharides or disaccharides; as used herein "component saccharides" refers to the saccharides that make up the polysaccharide. Component saccharides can include monosaccharides, disaccharides, trisaccharides, etc., and can also include sugars normally found in nature as well as non-natural and modified sugars as defined below, inter alia;

the presence or the amount of one or more block components, wherein a "block component" is made up of more than one saccharide or polysaccharide;

the presence or amount of one or more saccharide-representatives, wherein a "saccharide-representative" is a saccharide modified to enhance detectability, including saccharides modified by methods such as chemical modification, enzymatic or chemical digestion, inter alia;

the presence or amount of an indicator of three dimensional structure or a parameter related to three dimensional structure, e.g., activity, e.g., a structural motif or binding site, e.g., the presence or amount of a structure produced by cross-linking a polysaccharide, e.g., the cross-linking of specific saccharides which are not adjacent in the linear sequence; or the presence or amount of one or more modified saccharides, wherein a modified saccharide is one present in a starting material used to make a preparation but which is altered in the production of the preparation, e.g., a saccharide modified by cleavage.

In a preferred embodiment, one can further analyze the polysaccharide by the use of a secondary output, which includes one or more of: total charge; charge/mass ratio, density of charge; sequence; positioning of one or more active site; and polydispersity. "Total charge" of a polysaccharide such as heparin can be calculated by dividing the mass by the average molecular weight of a disaccharide (500) and multiplying that number by the average charge per disaccharide (2.3); or by calculating the charge based on one or more primary outputs, e.g., the identity and number of mono- and di-saccharide building blocks present. "Charge/mass ratio" can be calculated by dividing the total charge by the mass of the polysaccharide. "Density of charge" can be calculated by dividing the total charge by the average length of the polysaccharide. "Sequence" refers to the linear arrangement of covalently linked component saccharides, and can be determined by methods known in the art, e.g., the methods disclosed herein and in WO 00/65521, WO 02/23190, Venkataraman (1999); Shriver at al. (2000a); Shriver et al. (2000b); and Keiser et al. (2001); the entire teachings of which are incorporated herein by reference. "Positioning of the active site" refers to a correlation between a certain component polysaccharide and a given activity. In a preferred embodiment, the structural signature is determined by one or more methods chosen from the group consisting of MALDI-MS, ESI-MS, CE, HPLC, FPLC, fluorometry, ELISA, chromogenic assays, colorimetric assays, NMR and other spectroscopic techniques.

Some of the methods and compositions described herein are described with the use of one of the primary outputs, e.g., the amount of one or more component saccharides or disaccharides. However, it is to be understood that any of the above mentioned outputs can be used with, or in place of the output actually recited in the methods and compositions described herein.

In another aspect, the invention features a method of analyzing a polysaccharide drug, e.g., a heparin, synthetic heparin, or LMWH. The method includes:

providing or determining a first structural signature, e.g., any structural signature described herein for a batch of drug having a first level of preselected patient reaction, e.g., a preselected level of negative or positive reaction to the drug;

providing or determining a second structural signature, e.g., any structural signature described herein, for a second batch of drug having a second level of preselected patient reaction, e.g., a preselected level of negative or positive reaction to the drug;

comparing the first and second structural determination to associate a property of the drug, e.g., a chemical or structural property, with a preselected level of patient reaction. For example, one can determine the structure of a batch of drug having a relatively high level of unwanted effects, determine the structure of a batch of drug having a relatively low level of unwanted effects, and then compare the structural determinations of the two batches to correlate a property of the drug with the unwanted effects. In some embodiments, the method further includes selecting or discarding a batch of drug having a property correlated with the high or the low level of patient reaction.

As used herein, "batch" refers to a quantity of anything produced at one operation, e.g., a quantity of a compound produced all at one operation. A "batch of drug" is a quantity of a drug that was produced at one operation, e.g., in a single process.

The invention relates in part to novel methods of analyzing and thus defining the structural signature and activity of heterogeneous populations of sulfated polysaccharides. The invention provides methods to correlate structure with function (referred to as Compositional Analysis Method (CAM)) to identify key structural motifs, easily measured, that can be used to predict the activity of and monitor the levels of a heparin. The methods of the invention can be utilized to create glycoprofiles to standardize polysaccharide preparations such as heparin, synthetic heparin, and low molecular weight heparins with increased activity and bioavailability in vivo while maintaining a desired degree of consistency from batch to batch. The invention provides new, reliable and consistent preparations of polysaccharides, particularly of LMWHs, that have enhanced properties as compared to the current generation of commercially available LMWHs, as well as methods for preparing such preparations.

In one aspect, the invention is a method of analyzing the structural signature of a sample, e.g., a composition as described herein, including detecting the presence of a number of components, e.g., $I/GH_{NAc,6S}I/GH_{NS,3S,6S}$, $I/GH_{NS,6S}GH_{NS,3S,6S}$, $I/GH_{NAc,6S}GH_{NS,3S}$, $I/GH_{NS,6S}I/GH_{NS,3S}$, $I/GH_{NS,6S}I/GH_{NS,3S,6S}$, $I/GH_{NAc,6S}GH_{NS,3S}$, $I/GH_{NS,6S}I/GH_{NS,3S}$ or combinations thereof, as well as non-natural, e.g., modified, sugars. These signatures can be detected as is (e.g., by measuring their molecular weight, and sequencing, or by NMR, etc.) or can be detected indirectly by detecting their derivatives, e.g., $\Delta UH_{NAc,6S}GH_{NS,3S,6S}$, $\Delta UH_{NS,6S}GH_{NS,3S,6S}$, $\Delta UH_{NAc,6S}GH_{NS,3S}$, $\Delta UH_{NS,6S}GH_{NS,3S}$, $\Delta UH_{NS,6S}GH_{NS,3S,6S}$, $\Delta UH_{NAc,6S}GH_{NS,3S}$, $\Delta UH_{NS,6S}GH_{NS,3S}$ or combinations thereof, as well as non-natural, e.g., modified, sugars. As used herein, "non-natural sugars" refers to sugars having a structure that does not normally exist in heparin in nature. As used herein, "modified sugars" refers to sugars derived from natural sugars, which have a structure that does not normally exist in a polysaccharide in nature, which can occur in a LMWH as a result of the methods used to make the LMWH, such as the purification procedure. The results of this method are a set of values representing the glycoprofile of the composition.

As used herein, "p1" or "peak 1" refers to $\Delta U_{2S}H_{NS,6S}$; "p2" or "peak 2" refers to $\Delta U_{2S}H_{NS}$; "p3" or "peak 3" refers to $\Delta UH_{NS,6S}$; "p4" or "peak 4" refers to $\Delta U_{2S}H_{NAC,6S}$; "p5" or "peak 5" refers to $\Delta UH_{NS}$; "p6" or "peak 6" refers to $\Delta U_{2S}H_{NAC}$; "p7" or "peak 7" refers to $\Delta UH_{NAC,6S}$; "p8" or "peak 8" refers to $\Delta U\ H_{NAc,6S}GH_{NS,3S,6S}$; $\Delta U\ H_{NS,6S}GH_{NS,3S,6S}$; $\Delta U\ H_{NAc,6S}GH_{NS,3S}$; or $\Delta U\ H_{NS,6S}GH_{NS,3S}$, collectively. "p9" or "peak 9" and "p10" or "peak 10" refer to the non-natural sugars associated with peaks 9 and 10, respectively. The nomenclature "$\Delta U$" refers to an unsaturated uronic acid (iduronic acid (I) or glucuronic acid (G) that has a double bond introduced at the 4-5 position as a result of the lyase action of heparinases. Upon the introduction of the double bond the distinction between the stereo isomers I and U disappears, and hence the notation $\Delta U$: $\Delta$ to denote double bond, and U to denote that they can be derived from either I or G. Thus, as used herein, "$\Delta U$" represents both I and G, such that $\Delta U_{2S}H_{NS,6S}$ encompasses both $I_{2S}H_{NS,6S}$ and $G_{2S}H_{NS,6S}$; $\Delta U_{2S}H_{NS}$ encompasses both $I_{2S}H_{NS}$ and $G_{2S}H_{NS}$, and so forth. While the compositions of the invention are described as mole % of different building blocks, it is well known in the art that they can also be described as AUC %, as weight %, or by other known terminology within the scope of the invention.

A further embodiment of the invention relates to the use of a method described herein for analyzing a sample, e.g., a composition including a mixed population of polysaccharides, such as glycosaminoglycans (GAGs), HLGAGs, UFH, FH, or LMWHs. This method includes, inter alia, providing the composition; and determining if one or more, e.g., two, three, four, five six, or seven, of the following are present in a preselected range: $I/G_{2S}H_{NS,6S}$ (e.g., 15-85 mole %); $I/G_{2S}H_{NS}$ (e.g., 0.1-20 mole %); I/G $H_{NS,6S}$ (e.g., 0.1-20 mole %); $I/G_{2S}H_{NAc,6S}$ (e.g., 0.1-10 mole %); I/G $H_{NS}$ (e.g., 0.1-10 mole %); $I/G_{2S}H_{Nac}$ (e.g., 0.1-5 mole %); I/G $H_{NAc,6S}$ (e.g., 0.1-15 mole %); and/or I/G $H_{NAc,6S}GH_{NS,3S,6S}$; I/G $H_{NS,6S}GH_{NS,3S,6S}$; I/G $H_{NAc,6S}GH_{NS,3S}$; or I/G $H_{NS,6S}GH_{NS,3S}$ or a mixture thereof (e.g., 0.1-20 mole %); by measuring their representative building blocks, e.g., $\Delta U_{2S}H_{NS,6S}$; $\Delta U_{2S}H_{NS}$; $\Delta U\ H_{NS,6S}$; $\Delta U_{2S}H_{NAc,6S}$; $\Delta U\ H_{NS}$; $I/G_{2S}H_{NAc}$; $\Delta U\ H_{NAc,6S}$; $\Delta U\ H_{NAc,6S}GH_{NS,3S,6S}$; $\Delta U\ H_{NS,6S}GH_{NS,3S,6S}$; $\Delta U\ H_{NAc,6S}GH_{NS,3S}$; or $\Delta U\ H_{NS,6S}GH_{NS,3S}$; thereby analyzing the composition. In some embodiments, the method includes determining if all of the foregoing are present id a preselected range. As used herein, "in a preselected range" also includes and is satisfied by all lesser included ranges.

In some embodiments, the method includes determining if $\Delta U_{2S}H_{NS,6S}$ is present in the range of 45-80 mole %, 50-75 mole %, 55-70 mole %, or 60-65 mole %.

In some embodiments, the method includes determining if $\Delta U_{2S}H_{NS}$ is present in the range of 2-15 mole %, 5-10 mole %, or 6-9 mole %.

In some embodiments, the method includes determining if $\Delta UH_{NS,6S}$ is present in the range of 5-18 mole %, 7-15 mole %, or 10-12 mole %.

In some embodiments, the method includes determining if $\Delta UH_{2S}H_{NAc,6S}$ is present in the range of 0.5-7.5 mole %, 1-5 mole % or 1.5-3 mole %.

In some embodiments, the method includes determining if $\Delta UH_{NS}$ is present in the range of 1-7 mole %, 2-5 mole % or 3-4 mole %.

In some embodiments, the method includes determining if $\Delta U_{2S}H_{NAc}$ is present in the range of 0.1-5 mole %, 0.5-3 mole % or 1-2.5 mole %.

In some embodiments, the method includes determining if $\Delta UH_{Nac,6S}$ is present in the range of 0.1-12 mole %, 0.5-10 mole % or 1-6 mole %.

In some embodiments, the method includes determining if $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a mixture thereof is present in the range of 1-15 mole %; 2-10 mole %; 3-8 mole %; or 5-7 mole %.

In another embodiment, this method includes determining whether non-natural sugars are present in sample, e.g., a composition as described herein, in a preselected range, generally 0.1-5 mole %; 0.1-2.5 mole %; 0.1-1 mole %. In some embodiments, the method includes determining whether the non-natural sugar of peak 9 is present in the range of 0.1-5 mole %, 0.1-2.5 mole %, or 0.1-1 mole %. In some embodiments, the method includes determining whether the non-natural sugar of peak 10 is present in the range of 0.1-5 mole %, 0.1-2.5 mole %, or 0.1-1 mole %. In some embodiments, the method includes determining whether peak 11 is present in the range of 0.1-10 mole %, 1-5 mole %, or 2-4 mole %.

Thus, in another aspect, the invention includes a method of analyzing a sample by providing the sample and determining if a non-natural sugar, e.g., a modified sugar, is present in the sample. The non-natural sugar can be peak 9, peak 10, and/or peak 11.

In some embodiments, the method further includes detecting one or more biological activities of the sample, such as an effect on cellular activities such as undesired cell growth or proliferation; cellular migration, adhesion, or activation; neovasularization; angiogenesis; coagulation; HIT propensity; and inflammatory processes. In some embodiments the biological activity is anti-Xa activity; anti-IIa activity; FGF binding; protamine neutralization; and/or PF4 binding.

In some embodiments, the method can also include correlating one or more biological activities to the structural signature of the sample. In some embodiments, the method can also include creating a reference standard having information correlating the biological activity to the structural signature. This reference standard can be used, e.g., to predict the level of activity of a sample, e.g., a LMWH preparation. Thus, in another aspect, the invention provides a method for predicting the level of activity of a LMWH preparation by determining the structural signature of the LMWH preparation and comparing the determined structural signature to the reference standard described herein. The activity can be an effect on cellular activities such as cell growth or proliferation; cellular migration, adhesion, or activation; neovascularization; angiogenesis; coagulation; and inflammatory processes. In some embodiments, the activity is anti-Xa activity, anti-IIa activity, FGF binding, protamine neutralization, and/or PF4 binding.

In another aspect, the invention also provides a method of analyzing a sample of a heparin having a selected biological activity by determining if a component known to be correlated with the selected activity is present in the sample. The method can further include determining the level of the component, e.g., the mole % or AUC % of the component. The activity can be an effect on cellular activities such as cell growth or proliferation; cellular migration, adhesion, or activation; neovascularization; angiogenesis; coagulation; and inflammatory processes, anti-Xa activity, anti-IIa activity, PGF binding, protamine neutralization, and/or PF4 binding.

In some embodiments, the presence of $U_{2S}H_{NS}$, $U_{2S}H_{Nac,6S}$, $U_{2S}H_{Na}$, and/or $U_{2S}H_{NS,6S}$, e.g., in a range of 0.1-100 mole %, is indicative of PF4 binding activity. In some embodiments, the presence of $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a mixture thereof; e.g., in the range of 0.1-100 mole %, is indicative of anti-Xa activity.

In a preferred embodiment, the method further includes analyzing a plurality of compositions to determine the structural signature of each composition; detecting the biological activity of each composition; comparing the structural signature of the compositions to the detected biological activities; and correlating the biological activity with a structural signature or component thereof: e.g., a primary or secondary output of said structural signature. As used herein, "plurality" means two or more. The biological activity can be, e.g., effects on cellular activities such as undesired cell growth or proliferation; cell death (necrotic or apoptotic); cellular migration, adhesion, or activation; neovascularization; angiogenesis; coagulation; and inflammatory processes. In a preferred embodiment, the biological activity can include one or more of anti-Xa activity, anti-IIa activity, FGF binding, protamine neutralization, TFPI release, and/or PF4 binding.

In some embodiments, the biological activity-structural correlation information can be used to design a heparin, synthetic heparin, or LMWH preparation for a specific indication, e.g., renal impairment, autoimmunity, disease associated with coagulation, such as thrombosis, cardiovascular disease, vascular conditions or atrial fibrillation; migraine, atherosclerosis; an inflammatory disorder, such as autoimmune disease or atopic disorders; an allergy; a respiratory disorder, such as asthma, emphysema, adult respiratory distress syndrome (ARDS), cystic fibrosis, or lung reperfusion injury; a cancer or metastatic disorder; an angiogenic disorder, such as neovascular disorders of the eye, osteoporosis, psoriasis, and arthritis, Alzheimer's, or is undergoing or having undergone surgical procedure, organ transplant, orthopedic surgery, treatment for a fracture such as a hip fracture, hip replacement, knee replacement, percutaneous coronary intervention (PCI), stent placement, angioplasty, coronary artery bypass graft surgery (CABG). The specific indication can include cellular activities such as cell growth or proliferation; neovascularization; angiogenesis; cellular migration, adhesion, or activation; and inflammatory processes.

In another aspect the invention relates to a method of making one or more batches of a polysaccharide preparation, wherein one or more of the glycoprofile values of the batches varies less than a preselected range. In another aspect, the invention relates to a composition comprising multiple batches of a polysaccharide preparation, wherein one or more of the glycoprofile values for each batch varies less than a preselected range from a pre-selected desired glycoprofile. In some embodiments, the method includes determining the structural signature of one or more batches of a product, and selecting a batch as a result of the determination. In some embodiments, the method can also include comparing the results of the determination to preselected values, e.g., a reference standard. In other embodiments, the method can further include adjusting the dose of the batch to be administered, e.g., based on the result of the determination of the structural signature. Thus, in another aspect the invention relates to a method of determining a reference standard for a composition, e.g., a drug, by analyzing a sample, e.g., a sample including a composition including a mixed population of polysaccharides, such as glycosaminoglycans (GAGs), HLGAGs, UFH, FH, or LMWHs, including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™), and determining if one or more of the following are present in a preselected range: $\Delta U_{2S}H_{NS,6S}$; $\Delta U_{2S}H_{NS}$; $\Delta UH_{NS,6S}$; $\Delta U_{2S}H_{NAc,6S}$; $\Delta UH_{NS}$; $\Delta U_{2S}H_{NAc}$; $\Delta UH_{NAc,6S}$; $\Delta UH_{NAc,6S}GH_{NS,3S,6S}$; $\Delta UH_{NS,6S}GH_{NS,3S,6S}$; $\Delta UH_{NAc,6S}GH_{NS,3S}$; or $\Delta UH_{NS,6S}GH_{NS,3S}$; and/or I/G $H_{NAc,6S}GH_{NS,3S,6S}$; I/G $H_{NS,6S}GH_{NS,3S,6S}$; I/G $H_{NAc,6S}GH_{NS,3S}$; or I/G $H_{NS,6S}GH_{NS,3S}$ or a mixture thereof; thereby determining a reference standard for the composition. In some embodiments, the method includes determining if all of the foregoing are present in a preselected range, e.g., peak 1, $\Delta U_{2S}H_{NS,6S}$ (e.g., 15-85 mole %); peak 2, $\Delta U_{2S}H_{NS}$ (e.g., 0.1-20 mole %); peak 4, $\Delta U_{2S}H_{NAC,6S}$ (0.1-10 mole %); peak 6, $\Delta U_{2S}H_{NAC}$ (0.1-5 mole %); and/or peak 8, I/G $H_{NAc,6S}GH_{NS,3S,6S}$; I/G $H_{NS,6S}GH_{NS,3S,6S}$; I/G $H_{NAC,6S}GH_{NS,3S}$ or I/G $H_{NS,6S}GH_{NS,3S}$ or a mixture thereof (e.g., 0.1-20 mole %). In one embodiment, the dose or amount to be administered to a patient is adjusted depending on the level of peak 8 present; e.g., to maintain the levels of anti-Xa/IIa activity, e.g., to maintain a dose of 100 IU of anti-Xa activity.

In one embodiment, the invention relates to a method of determining a reference standard for a drug by analyzing the composition and determining the bioequivalence and/or bioavailability of one or more of the components in the mixture. As used herein, "bioequivalence" means "the absence of a significant difference in the rate and extent to which an active ingredient or active moiety in pharmaceutical equivalents or pharmaceutical alternatives becomes available at the site of drug action when administered at the same molar dose under similar conditions."

As used herein, "bioavailability" is "the rate and extent to which the active ingredient or active moiety is absorbed from a drug product and becomes available at the site of action." For compounds that are not intended to be absorbed into the bloodstream, bioavailability may be assessed by a measurement intended to reflect the rate and/or extent to which the active ingredient or active moiety becomes available at the site of action. From a pharmacokinetic perspective, bioavailability data for a given formulation provide an estimate of the relative fraction of the orally administered dose that is absorbed into the systemic circulation when compared to the bioavailability data for a solution, suspension, subcutaneous or intravenous dosage form. Bioavailability studies may provide other pharmacokinetic information related to distribution, elimination, the effects of nutrients on absorption of the drug, dose proportionality, and/or linearity in pharmacokinetics of the active moieties and, where appropriate, inactive moieties. Bioavailability data may also provide information indirectly about the properties of a drug substance prior to entry into the systemic circulation, such as permeability and the influence of presystemic enzymes and/or transporters (e.g., p-glycoprotein). Bioavailability for orally administered drug products may be documented by developing a systemic exposure profile obtained from measuring the concentration of active ingredients and/or active moieties and, when appropriate, its active metabolites over time in samples collected from the systemic circulation.

Several in vivo and In vitro methods can be used to measure product quality bioavailability and establish bioequivalence. These include pharmacokinetic, pharmacodynamic, clinical, and in vitro studies.

As used herein, "pharmacokinetic" refers to the kinetics of release of the drug substance from the drug product into the systemic circulation, as well as clearance, volume of distribution, and absorption, as determined by physiological variables (e.g. gastric emptying, motility, pH). Pharmacokinetics may be evaluated in an accessible biological matrix such as blood, plasma, and/or serum. Pharmacokinetic measurements may also include AUC, does-dependency of activity, peak levels in plasma, time to peak, disposition half-life, and terminal half-life.

As used herein, "pharmacodynamic" refers to defining factors that cause variability in clinical drug response using general assessments, including bone densitometry and caliper total body fat; pulmonary assessments, including pulmonary function testing, expired nitric oxide, pulmonary imaging; Cardiovascular assessments, including cardiac monitoring, ambulatory blood pressure; Holter monitoring, telemetry, ECG, vital signs, cardiac imaging; Nervous system assessments, including electroencephalography, mental function testing, psychomotor function testing, pharmacokinetic EEG; ENT assessments, including audiometric testing, acoustic rhinometry, intraocular pressure, digital retinography; and gastrointestinal assessments, including gastric pH monitoring, endoscopy, imaging, and/or gastric motility.

Thus in one aspect, the invention relates to a method for determining bioequivalence. The method includes some or all of the following: providing or determining the structural signature of a first composition; providing or determining the bioavailability of the first composition; providing or determining the structural signature of a second composition; providing or determining the bioavailability of the second composition; and comparing the structural compositions and bioavailability of the first and second compositions. In some embodiments, bioavailability is determined determining the absorbance characteristics of the composition in one or more subjects, e.g., human or veterinary subjects or experimental animals; and determining the clearance characteristics of the composition in one or more subjects, e.g., human or veterinary subjects or experimental animals.

The invention also includes methods for monitoring subjects receiving polysaccharides. Until now, subjects receiving heparins and HLGAG preparations have been monitored by testing their activated partial thromboplastin time (aPTT) or thrombin clotting times (TCT). However, this test depends in large part on the activity and availability of other substances endogenous to the subject such as fibrinogen and factor VIII, and thus may not give an accurate indication of actual levels. Furthermore, this test is also dependent on the presence of significant anti-IIa activity, which is substantially absent in the LMWHs currently known in the art. Patients receiving heparin but demonstrating an inadequate aPTT response can be evaluated using an anti-Xa assay. A quantitative anti-Xa assay is necessary for monitoring heparin in patients with a prolonged aPTT that may be related to lupus anticoagulants or deficiencies of factor XII and the contact factors (prekallikrein and high molecular weight kininogen); current anti-Xa assays are expensive, take a long time, and are not readily available, so a need exists for a new method of following anti-Xa levels.

Thus the invention also relates to methods of monitoring a subject receiving a polysaccharide, comprising monitoring the level of one or more of the components of the polysaccharide being administered. In one embodiment, the invention relates to monitoring the levels of a single component. In a further embodiment, the invention relates to monitoring the level of a component associated with a biological activity of the polysaccharide. In another embodiment, the invention relates to monitoring a subject receiving a polysaccharide comprising monitoring the levels of components of the polysaccharide correlating to anti-IIa activity or to anti-Xa activity. In other aspect, the methods can include monitoring a subject receiving a polysaccharide, e.g., a LMWH, by monitoring the levels, e.g., serum levels, of one or more components of the polysaccharide correlating to an activity, e.g., PF4 binding. The methods of the invention include monitoring hexasaccharide and octasaccharide fractions of heparins in plasma without prior heparinase digestion; smaller fragments may be monitored following treatment of the sample with an agent as described herein, such as a heparinase or a chemical digestive agent.

Thus in another aspect the invention provides a method of analyzing a sample or a subject, e.g., a sample from a subject, for a heparin having anti-Xa activity. In some embodiments, the sample comprises a bodily fluid, e.g., blood or a blood-derived fluid, or urine. In some embodiments, the heparin comprises UFH or a LMWH, e.g., a LMWH having anti-Xa activity, M118, M1115, M411, M108, M405, M312, enoxaparin; dalteparin; certoparin; ardeparin; nadroparin; parnaparin; reviparin; tinzaparin, or fondaparinux. The method can include some or all of the following: providing a sample, e.g., from a subject, e.g., a human or veterinary subject or an experimental animal; determining if one or more components chosen from the group consisting of $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a fragment or fragments thereof is present in the sample; and optionally, measuring the level of the component or components. In some embodiments, the steps are repeated, e.g., at pre-selected intervals of time, e.g., every two to twenty-four hours, every four to twelve hours, every six to ten hours, continuous monitoring. In some embodiments, the method can also include establishing a baseline, e.g., a baseline for the component or components prior to the subject receiving the heparin. In some embodiments, the method also includes determining if —$U_{2S}H_{NS,6S}$; —$U_{2S}H_{NS}$; —$UH_{NS,6S}$; —$U_{2S}H_{NAC,6S}$; —$UH_{NS}$; —$U_{2S}H_{NAC}$; or —$UH_{NAC,6S}$ is present in the sample. In some embodiments, the method further comprises determining if the components of one or more of peak 9, peak 10, or peak 11 is present in the sample. In some embodiments, the method also includes monitoring for presence, tissue distribution, spatial distribution, temporal distribution or retention time, in a cell or a subject, e.g., an experimental animal. In some embodiments, the method also includes determining the structural signature of one or more batches of a product. In some embodiments, the method also includes selecting a batch as a result of the determination. In some embodiments, the method also includes comparing the results of the determination to preselected values, e.g., a reference standard.

In some embodiments, the determination step includes purifying the sample; optionally fractionating the sample; contacting the sample with at least one agent and determining the structural signature of the digested sample. The agent can be an enzyme, e.g., a heparin degrading enzyme, e.g., heparinase I, heparinase II, heparinase III, heparinase IV, heparanase and functionally active variants and fragments thereof, or a chemical agent, e.g., $H_2O_2$, $Cu^+$ and $H_2O_2$, isoamyl nitrite, nitrous acid, benzyl ester or alkaline treatment.

In some embodiments, the determination step includes: optionally purifying the sample, contacting the sample with a reagent specific for one or more of the components, e.g., a peptide, protein, lectin, or antibody; and detecting the binding of the antibody to the component. In some embodiments, the determination includes determining if one or more components chosen from the group consisting of $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a fragment or fragments thereof is present in the range of 0.1-20 mole %.

In some embodiments, the human or veterinary subject is having, at risk for having, or recovering from a surgical intervention, for example, angioplasty, stent placement, cardiopulmonary bypass procedure, tissue or organ transplant, coronary revascularization surgery, orthopedic surgery, treatment for a fracture such as a hip fracture, hip replacement, knee replacement, PCI, and prosthesis replacement surgery. In some embodiments, the human or veterinary subject is a patient with abnormal renal function as measured by RFI, urea, creatinine, phosphorus, GFR or BUN levels in blood or GFR or urine. In some embodiments, the human or veterinary subject has or is at risk for having complications associated with receiving heparin or LMWH, e.g., HIT, the human or veterinary subject is overweight or obese, for example a subject who is 20, 30, 40, 50 or more pounds overweight. In some embodiments, the human or veterinary subject is extremely thin or frail, for example a subject who is 20, 30, 40, 50 or more pounds underweight, or who is suffering from an immune deficiency, e.g., HIV/AIDS. In some embodiments, the human or veterinary subject is a pediatric patient. In some embodiments, the human or veterinary subject is pregnant. In some embodiments, the human or veterinary subject is a patient having a spinal or epidural hematoma. In some embodiments, the human or veterinary subject is a patient with a prosthetic heart valve. In some embodiments, the human or veterinary subject has an ATIII deficiency or abnormality. In some embodiments, the human or veterinary subject has a factor Xa deficiency or abnormality.

In some embodiments, the method further comprises monitoring for presence, tissue distribution, spatial distribution, temporal distribution or retention time, in a cell or a subject, e.g., an experimental animal. In some embodiments, the method includes determining the structural signature of one or more batches of a product. In some embodiments, the method further includes selecting a batch as a result of the determination. In some embodiments, the method further includes comparing the results of the determination to preselected values, e.g., a reference standard.

In some embodiments, the sample includes a population of polysaccharides wherein less than or equal to 20% are <2000 Da species, greater than or equal to 68% are 2000-8000 Da species, and less than or equal to 18% are >8000 Da species, or the same as is found in commercially available enoxaparin preparations, preferably with an average molecular weight of about 4500 Da. In some embodiments, the sample has approximately 100 IU/mg anti-Xa activity. In some embodiments, the sample has a pH of 5.5-7.5. In some embodiments, one or more components of the sample is tagged or labeled.

In another aspect, the invention provides a method of analyzing a sample or a subject, e.g., monitoring a subject receiving a heparin having anti-IIa activity. In some embodiments, the sample comprises a bodily fluid, e.g., blood or a blood-derived fluid, or urine. In some embodiments, the heparin comprises UFH or a LMWH, e.g., a LMWH having anti-Xa activity, M118, M115, M411, M108, M405, M312, enoxaparin; dalteparin; certoparin; ardeparin; nadroparin; parnaparin; reviparin; tinzaparin, or fondaparinux. The method includes some or all, typically all, of the following: providing a sample, e.g. from a subject, e.g., a human or veterinary subject, or an experimental animal; and determining if one or more structural signature outputs known to be associated with anti-IIa activity is present in the sample; and optionally, determining the level of the component or components. In some embodiments, one or more of the steps are repeated at preselected intervals of time, e.g., every two to twenty-four hours, every four to twelve hours, every six to ten hours, or continuously.

In some embodiments, the structural signature output associated with anti-IIa activity is a polysaccharide comprising at least one of $\Delta UH_{NAc,6S}GH_{NS,3S,6S}$, $\Delta UH_{NS,6S}GH_{NS,3S,6S}$, $\Delta UH_{NAc,6S}GH_{NS,3S}$, or $\Delta UH_{NS,6S}GH_{NS,3S}$ with one or more other disaccharide units. In some embodiments, the method further comprises establishing a baseline for the component or components prior to the subject receiving the heparin. In some embodiments, the method further comprises monitoring presence, tissue distribution, spatial distribution, temporal distribution or retention time, in a cell or a subject, e.g., an experimental animal. In some embodiments, the method includes determining the structural signature of one or more batches of a product. In some embodiments, the method further includes selecting a batch as a result of the determination. In some embodiments, the method further includes comparing the results of the determination to preselected values, e.g., a reference standard.

In some embodiments, the determination step includes purifying the sample; optionally fractionating the sample; contacting the sample with at least one agent; and determining the structural signature of the digested sample. The agent can be an enzyme, e.g., a heparin degrading enzyme, e.g., heparinase I, heparinase II, heparinase III, heparinase IV, heparanase and functionally active variants and fragments thereof, or a chemical agent, e.g., $H_2O_2$, $Cu^+$ and $H_2O_2$, isoamyl nitrite, nitrous acid, benzyl ester or alkaline treatment.

In some embodiments, the determination step includes: optionally purifying the sample, contacting the sample with a reagent specific for one or more of the components, e.g., a peptide, protein, lectin, or antibody; and detecting the binding of the antibody to the component. In some embodiments, the determination includes determining if one or more components chosen from the group consisting of $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a fragment or fragments thereof is present in the range of 0.1-20 mole %.

In some embodiments, the human or veterinary subject is having, at risk for having or recovering from a surgical intervention, for example, angioplasty, stent placement, cardiopulmonary bypass procedure, tissue or organ transplant, coronary revascularization surgery, orthopedic surgery, treatment for a fracture such as a hip fracture, hip replacement, knee replacement, PCI, and prosthesis replacement surgery. In some embodiments, the human or veterinary subject is a patient with abnormal renal function as measured by RFI, urea, creatinine, phosphorus, GFR or BUN levels in blood or GFR or urine. In some embodiments, the human or veterinary subject has or is at risk for having complications associated with receiving heparin or LMWH, e.g., HIT, the human or veterinary subject is overweight or obese, for example a subject who is 20, 30, 40, 50 or more pounds overweight. In some embodiments, the human or veterinary subject is extremely thin or frail, for example a subject who is 20, 30, 40, 50 or more pounds underweight, or who is suffering from an immune deficiency, e.g., HIV/AIDS. In some embodiments, the human or veterinary subject is a pediatric patient. In some embodiments, the human or veterinary subject is pregnant. In some embodiments, the human or veterinary subject is a patient having a spinal or epidural hematoma. In some embodiments, the human or veterinary subject is a patient with a prosthetic heart valve. In some embodiments, the human or veterinary subject has an ATIII deficiency or abnormality. In some embodiments, the human or veterinary subject has a factor Xa deficiency or abnormality.

In some embodiments, the method further comprises monitoring for presence, tissue distribution, spatial distribution, temporal distribution or retention time, in a cell or a subject, e.g., an experimental animal. In some embodiments, the method includes determining the structural signature of one or more batches of a product. In some embodiments, the method further includes selecting a batch as a result of the determination. In some embodiments, the method further includes comparing the results of the determination to preselected values, e.g., a reference standard.

In some embodiments, the sample includes a population of polysaccharides wherein less than or equal to 20% are <2000 Da species, greater than or equal to 68% are 2000-8000 Da species, and less than or equal to 18% are >8000 Da species, or the same as is found in commercially available enoxaparin preparations, preferably with an average molecular weight of about 4500 Da. In some embodiments, the sample has approximately 100 IU/mg anti-Xa activity. In some embodiments, the sample has a pH of 5.5-7.5. In some embodiments, one or more components of the sample is tagged or labeled.

In another aspect, the invention provides a method of analyzing a sample or a subject, e.g., monitoring a LMWH in sample or a subject. The method includes some or all, typically all, of the following: providing a sample, e.g., from a subject, e.g., a human or veterinary subject, or an experimental animal; and determining if one or more non-natural sugars, e.g., modified sugars, are present in the sample; and optionally, determining the level of the non-natural sugar. In some embodiments, the LMWH is enoxaparin. In some embodiments, the non-natural sugars are benzylated. In some embodiments, the non-natural sugars comprise one or more of peaks 9 and 10. In some embodiments, the sample comprises a bodily fluid, e.g., blood or a blood-derived bodily fluid, or urine. In some embodiments, one or more of the steps are repeated at pre-selected intervals of time, e.g., every two to twenty-four hours, every four to twelve hours, every six to ten hours, continuously.

In some embodiments, the determination step includes purifying the sample; optionally fractionating the sample; contacting the sample with at least one agent and determining the structural signature of the digested sample. The agent can be an enzyme, e.g., a heparin degrading enzyme, e.g., heparinase I, heparinase II, heparinase III, heparinase IV, heparanase and functionally active variants and fragments thereof, or a chemical agent, e.g., $H_2O_2$, $Cu^+$ and $H_2O_2$, isoamyl nitrite, nitrous acid, benzyl ester or alkaline treatment.

In some embodiments, the determination step includes: optionally purifying the sample, contacting the sample with a reagent specific for one or more of the components, e.g., a peptide, protein, lectin, or antibody; and detecting the binding of the antibody to the component. In some embodiments, the determination includes determining if one or more components chosen from the group consisting of $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$ or a fragment or fragments thereof is present in the range of 0.1-20 mole %.

In some embodiments, the human or veterinary subject is having, at risk for having, or recovering from a surgical intervention, for example, angioplasty, stent placement, cardiopulmonary bypass procedure, tissue or organ transplant, coronary revascularization surgery, orthopedic surgery, treatment for a fracture such as a hip fracture, hip replacement, knee replacement, PCI, and prosthesis replacement surgery. In some embodiments, the human or veterinary subject is a patient with abnormal renal function as measured by RFI, urea, creatinine, phosphorus, GFR or BUN levels in blood or GFR or urine. In some embodiments, the human or veterinary subject has or is at risk for having complications associated with receiving heparin or LMWH, e.g., HIT, the human or veterinary subject is overweight or obese, for example a subject who is 20, 30, 40, 50 or more pounds overweight. In some embodiments, the human or veterinary subject is extremely thin or frail, for example a subject who is 20, 30, 40, 50 or more pounds underweight, or who is suffering from an immune deficiency, e.g., HIV/AIDS. In some embodiments, the human or veterinary subject is a pediatric patient. In some embodiments, the human or veterinary subject is pregnant. In some embodiments, the human or veterinary subject is a patient having a spinal or epidural hematoma. In some embodiments, the human or veterinary subject is a patient with a prosthetic heart valve. In some embodiments, the human or veterinary subject has an ATIII deficiency or abnormality. In some embodiments, the human or veterinary subject has a factor Xa deficiency or abnormality.

In some embodiments, the method further comprises monitoring for presence, tissue distribution, spatial distribution, temporal distribution or retention time, in a cell or a subject, e.g., an experimental animal. In some embodiments, the method includes determining the structural signature of one or more batches of a product. In some embodiments, the method further includes selecting a batch as a result of the determination. In some embodiments, the method further includes comparing the results of the determination to preselected values, e.g., a reference standard.

In some embodiments, the sample includes a population of polysaccharides wherein less than or equal to 20% are <2000 Da species, greater than or equal to 68% are 2000-8000 Da species, and less than or equal to 18% are >8000 Da species, or the same as is found in commercially available enoxaparin preparations, preferably with an average molecular weight of about 4500 Da. In some embodiments, the sample has approximately 100 IU/mg anti-Xa activity. In some embodiments, the sample has a pH of 5.5-7.5. In some embodiments, one or more components of the sample is tagged or labeled.

In another aspect, the invention relates to a method of analyzing a polysaccharide drug, e.g., a heparin, synthetic heparin, or LMWH comprising the steps of:
 a. determining a first structural signature, e.g., any structural signature described herein for a first batch of drug having a first level of preselected patient reaction, e.g., a preselected level of negative or positive reaction to the drug;
 b. determining a second structural signature, e.g., any structural signature described herein, for a second batch of drug having a second level of preselected patient reaction, e.g., a preselected level of negative or positive reaction to the drug; and
 c. comparing the first and second structural signature determinations to determine the presence or absence of a correlation between a property of the drug. e.g., a chemical or structural property, with a preselected level of patient reaction.

As used herein, "preselected patient reaction" refers to any reaction of interest, whether it be a positive or negative reaction. For instance, a positive patient reaction might be anticoagulation, shrinkage of a tumor, surgical intervention without occurrence of complications such as thrombosis, e.g., deep vein thrombosis; non-occurrence of ischemic complications of unstable angina and/or non-Q-wave myocardial infarction; relief of deep vein thrombosis; and non-occurrence of thromboembolic complications due to severely restricted mobility during acute illness. A negative patient reaction might be epidural or spinal hematoma; hemorrhage; thrombocytopenia; elevations of serum aminotransferases; local irritation, pain, hematoma, ecchymosis, and erythema; anemia; ecchymosis; fever; nausea; edema; peripheral edema; dyspnea; confusion; diarrhea; pneumonia; atrial fibrillation; Heart failure; Lung edema; local reactions at the injection site (i.e., skin necrosis, nodules, inflammation, oozing); systemic allergic reactions (i.e., pruritus, urticaria, anaphylactoid reactions); vesiculobullous rash; purpura; thrombocytosis; thrombocytopenia with thrombosis; hyperlipidemia; hyperlipidemia with marked hypertriglyceridemia; ataxia, decreased motility; cyanosis; and coma.

In another aspect, the invention relates to selecting a safer, less variable LMWH to use for treating a patient, by determining the structure structural signature of a first batch of drug having a relatively high level of undesirable patient reactions, determining the structural signature of a second batch of drug having a relatively low level of undesirable patient reactions, and selecting a primary or secondary output correlated with the high or the low level of patient reactions. As used herein, "desirable patient reaction" refers to, inter alia, a preselected positive patient reaction as defined above. As used herein, "undesirable patient reaction" refers to an unwanted patient reaction, such as a negative patient reaction as defined above.

The invention also relates to the development of a "bed side" monitoring system based upon assaying a more purified form of an active component of LMWH using assay techniques known in the art including, but not limited to chromogenic reagents and ELISA techniques.

In another aspect, the invention relates to a method of treating patients that have been excluded from LMWH treatment such as obese patients, pediatric patients, patients with abnormal renal function as measured by RFI, urea, creatinine, phosphorus, GFR or BUN in blood and urine and the interventional cardiology patient population by monitoring a subject receiving a polysaccharide, comprising monitoring the level of one or more of the components of the polysaccharide being administered. In another aspect, the invention relates to a method of treating patients with complications of LMWH by monitoring a subject receiving a polysaccharide, comprising monitoring the level of one or more of the components of the polysaccharide being administered. In another aspect, the invention relates to the selection of a LMWH for treatment of a patient previously excluded from LMWH treatment because of an elevated risk of a negative patient reaction, by selecting a LMWH that has a low level or none of a primary or secondary output associated with a negative patient reaction. The invention further relates to LMWH compositions comprising one or more non-natural sugar components. In a preferred embodiment, the non-natural sugar component may be the sugars associated with peaks 9, 10 and 11. In a related aspect, the invention relates to methods of monitoring a subject receiving a LMWH having a non-natural sugar component, the method comprising monitoring the subject for levels of the non-natural sugar, preferably in the bodily fluid of the subject.

The invention also relates to a method of determining the safety of compositions including a mixed population of polysaccharides, such as glycosaminoglycans (GAGs), HLGAGs, UFH, FH, or LMWHs including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™) e, or Fondaparinux (Arixtra™) in the treatment of subtypes of renal disease.

The invention also relates to a method for further understanding the mechanism of action of a specific heparin. LMWH or synthetic heparin and differentiating it from other heparins, LMWHs or synthetic heparins by analyzing and defining the structural signature and activity of one or more of the heparins, LMWHs or synthetic heparins in a heterogeneous population of sulfated polysaccharides.

The invention also relates to a method for further understanding the mechanism of action of specific, individual components of specific heparins, LMWHs or synthetic heparins and thereby differentiating it from other heparins, LMWHs or synthetic heparins by analyzing and defining the structural signature and activity of specific components. The invention further relates to a method for specifically identifying components of heparins, LMWHs or synthetic heparins which bind to proteins or other molecules which are associated with disease states or negative patient reactions, using, inter alia, chip-based specific affinity assays such as those disclosed in Keiser, et al. *Nat Med* 7, 123-8 (2001). This chip-based approach to assess the binding of heparin fragments to various proteins may be readily used to assay an array of plasma and other proteins and assess binding properties.

The invention also relates to a method for broadening the therapeutic utility of heparins, LMWHs or synthetic heparins for use in areas other than as modulators of hemostasis, by understanding the mechanism of action of specific, individual components of specific heparins, LMWHs or synthetic heparins by analyzing and defining the structural signature and activity of specific components and the effect those components can have in the treatment of a specific disease.

The invention also relates to a method for broadening the therapeutic utility of heparins, LMWHs or synthetic heparins for use in areas other than as modulators of hemostasis, by designing compositions with enhanced activities for these diseases by analyzing and defining the structural signature and activity of specific components and the effect those components can have in the treatment of a specific disease. In one embodiment, the method can include selecting a heparin, LMWH or synthetic heparin, based, e.g., on the presence or absence of a structural signature associated with a specific activity, e.g., a preselected range of structural signatures associated with a specific activity. In one embodiment, the method can include designing a composition of a heparin, LMWH, or synthetic heparin for treatment of subjects determined to be at risk for thrombocytopenia, e.g., heparin-induced thrombocytopenia (HIT), for example, patients having an immunodeficiency, e.g., AIDS, HIV, hereditary immunodeficiency or immunodeficiency caused by an environmental or medicinal agents (e.g., a chemotherapeutic agent or radiation treatment.) The heparin, LMWH or synthetic heparin composition can be designed to treat such subjects, e.g., a composition that has decreased PF4 binding, e.g., has a decreased amount of one or more of the following, e.g., one or more of the following is decreased as compared to a preselected range: peak 1, $\Delta U_{2S}H_{NS,6S}$ (e.g., less than about 60 mole %, e.g., 15-30 mole %); peak 2, $\Delta U_{2S}H_{NS}$ (e.g., less than about 5 mole %, e.g., 1.8-3.5 mole %); peak 4, $\Delta U_{2S}H_{NAC,6S}$ (e.g., less than about 2 mole %, e.g., 0.1-1.0 mole %); and/or peak 6, $\Delta U_{2S}H_{NAC,6S}$ (e.g., less than about 2 mole %, e.g., 0.1-0.5 mole %). Preferably, the composition has decreased amounts of all of the following: peak 1: $\Delta U_{2S}H_{NS,6S}$; peak 2: $\Delta U_{2S}H_{NS}$; peak 4: $\Delta U_{2S}H_{NAC,6S}$; and/or peak 6: $\Delta U_{2S}H_{NAC}$.

The invention also relates to broadening the therapeutic utility of heparins, LMWHs or synthetic heparins for treating clot bound thrombin by designing novel LMWHs of smaller sizes, and/or of increased anti-IIa activity that are active and can reach and treat the thrombus.

The invention also relates to a method for designing heparins, LMWHs or synthetic heparins with ideal product profiles including, but not limited to such features as high activity, having both anti-Xa and anti-IIa activity, titratable, well characterized, neutralizable, lower side effects including reduced HIT, attractive pharmacokinetics, and/or reduced PF4 binding that allow for optional monitoring and can be practically manufactured by analyzing and defining the structural signature and activity of specific components of a composition that includes a mixed population of polysaccharides, such as glycosaminoglycans (GAGs), HLGAGs, UFH, FH, LMWHs, or synthetic heparins including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), or Fondaparinux (Arixtra™) and enriching for components with desired activities and de-enriching for components with undesirable activities. As used herein, "desired activities" refers to those activities that are beneficial for a given indication, e.g., a positive patient reaction as defined herein, inter alia. An "undesirable activity" may include those activities that are not beneficial for a given indication, e.g., a negative patient reaction, as defined herein, inter alia. A given activity may be a desired activity for one indication, and an undesired activity for another, such as anti-IIa activity, which while undesirable for certain indications, is desirable in others, notably acute or trauma situations, as discussed above.

The invention also relates to a method for designing novel heparins, LMWHs or synthetic heparins with different or ideal anti-IIa activities using rational design based upon knowing that anti-Xa activity requires at least a pentasaccharide with a critical 3-O sulfate group on an internal glucosamine, anti-IIa activity requires longer saccharides and the positional orientation between the pentasaccharide and the thrombin binding site is crucial. The method can also include designing novel heparins, LMWHs or synthetic heparins using rational design based upon knowing that decreased PF4 binding requires the reduced presence of peaks 1, 2, 4 and 6, e.g., the presence of these peaks is reduced as compared to UFH, e.g., the presence of these peaks at less than about 60 mole % of peak 1, e.g., 15-30 mole %; less than about 5 mole % of peak 2, e.g., 1.5-3.5 mole %; less than about 2 mole % of peak 4, e.g., 0.1-1.5 mole % and/or less than about 2 mole % of peak 6, e.g., 0.1-0.5 mole %.

The invention also relates to novel heparins made by the methods of the invention, e.g., novel heparins, LMWHs or synthetic heparins with desired product profiles including, but not limited to such features as high activity, both anti-Xa and anti-IIa activity, titratability, well characterized, neutralizable (e.g. by protamine), reduced side effects including reduced HIT, and/or attractive pharmacokinetics, that allow for optional monitoring, and novel heparins, LMWHs or synthetic heparins with different or enhanced anti-IIa activities. Thus in one aspect, the invention includes a LMWH preparation having an increased or decreased ratio of anti-IIa activity and anti-Xa activity, e.g., a LMWH preparation made by the methods described herein. In another aspect, the invention includes a panel of two or more LMWH preparations having different ratios of anti-IIa activity and anti-Xa activity, e.g., LMWH preparations made by the methods described herein.

In one aspect, the method includes a method of producing a LMWH preparation having or not having a pre-selected biological activity. The method can include some or all of the following: providing one or more aliquots of heparin; optionally fractionating the heparin; modifying the aliquots of heparin under conditions designed to produce the activity; and optionally purifying the digested aliquots. In some embodiments, the desired biological activity is an effect on cellular activities such as cell growth or proliferation; cellular migration, adhesion, or activation; neovascularization; angiogenesis; coagulation; and Inflammatory processes. In some embodiments, the desired biological activity is anti-IIa activity; anti-Xa activity; platelet factor 4 binding; FOP binding; or sensitivity to neutralization with protamine. In some embodiments, the desired biological activity is anti-IIa activity and anti-Xa activity. In some embodiments, the aliquots are modified by chemically or enzymatically digesting the FH or UFH, e.g., by enzymatic digestion carried out using one or more heparin degrading enzymes, e.g., heparinase I, heparinase II, heparinase III, heparinase IV, heparanase or functionally active variants and fragments thereof. In some embodiments, the chemical digestion is carried out by a chemical chosen from the group consisting of oxidative depolymerization with $H_2O_2$ or $Cu^+$ and $H_2O_2$, deaminative cleavage with isoamyl nitrite, or nitrous acid, β-eliminative cleavage with benzyl ester or by alkaline treatment. In some embodiments, the method also includes testing the LMWH preparation for the desired biological activity.

In another aspect, the invention also includes a LMWH preparation prepared by the methods described herein, e.g., a LMWH preparation having anti-IIa activity and anti-Xa activity.

In another aspect, the invention provides a LMWH composition having both anti-Xa and anti-IIa activity comprising less than or equal to 20%<2000 Da species, greater than or equal to 68% 2000-8000 Da species, and less than or equal to 18%>8000 Da species, preferably with an average molecular weight of about 4500 Da, wherein the anti-Xa activity is >50% neutralizable by protamine and the anti-IIa activity is >70% neutralizable by protamine. In some embodiments, the LMWH composition has approximately 100 IU/mg anti-Xa activity. In some embodiments, the LMWH composition has a pH of 5.5-7.5. In some embodiments, the LMWH composition comprises $\Delta U_{2S}H_{NS,6S}$ in the range of 15-85 mole %; $\Delta U_{2S}H_{NS}$ in the range of 0.1-20 mole %; $\Delta UH_{NS,6S}$ in the range of 0.1-20 mole %; $\Delta U_{2S}H_{NAc,6S}$ in the range of 0.1-10 mole %; $\Delta UH_{NS}$ in the range of 0.1-10 mole %; $\Delta U_{2S}H_{NAc}$ in the range of 0.1-5 mole %; $\Delta UH_{NAc,6S}$ in the range of 0.1-15 mole %; and $\Delta UH_{NAc,6S}GH_{NS,3S,6S}$ in the range of 0.1-20 mole %. In some embodiments, the LMWH composition is free of or substantially free of non-natural sugars. In some embodiments, the LMWH composition further comprises greater than 30 IU/mg anti-IIa activity.

In another aspect, the invention provides a LMWH that is substantially free of non-natural sugars, e.g., the sugars associated with peaks 9 and 10, and comprising less than or equal to 20%<2000 Da species, greater than or equal to 68% 2000-8000 Da species, and less than or equal to 18%>8000 Da species, preferably with an average molecular weight of about 4500 Da. In some embodiments, the LMWH composition has approximately 100 IU/mg anti-Xa activity. In some embodiments, the LMWH composition has a pH of 5.5-7.5. In some embodiments, the LMWH composition comprises $\Delta U_{2S}H_{NS,6S}$ in the range of 15-85 mole %; $\Delta U_{2S}H_{NS}$ in the range to of 0.1-20 mole %; $\Delta UH_{NS,6S}$ in the range of 0.1-20 mole %; $\Delta U_{2S}H_{NAc,6S}$ in the range of 0.1-10 mole %; $\Delta UH_{NS}$ in the range of 0.1-10 mole %; $\Delta U_{2S}H_{NAc}$ in the range of 0.1-5 mole %; $\Delta UH_{NAc,6S}$ in the range of 0.1-15 mole %; and $\Delta UH_{NAc,6S}GH_{NS,3S,6S}$ in the range of 0.1-20 mole %. In some embodiments, the LMWH composition further comprises greater than 30 IU/mg anti-IIa activity.

In another aspect, the invention provides a LMWH which, as compared with enoxaparin, is enriched, e.g., has 5%, 10%, or 20% more non-natural sugars, e.g., the sugars associated with peaks 9, 10, 11, or 12, than enoxaparin, and comprising less than or equal to 20%<2000 Da species, greater than or equal to 68% 2000-8000 Da species, and less than or equal to 18%>8000 Da species, preferably with an average molecular weight of about 4500 Da. In some embodiments, the LMWH composition has approximately 100 IU/mg anti-Xa activity. In some embodiments, the LMWH composition has a pH of 5.5-7.5. In some embodiments, the LMWH composition comprises $\Delta U_{2S}H_{NS,6S}$ in the range of 15-85 mole %; $\Delta U_{2S}H_{NS}$ in the range of 0.1-20 mole %; $\Delta UH_{NS,6S}$ in the range of 0.1-20 mole %; $\Delta U_{2S}H_{NAc,6S}$ in the range of 0.1-10 mole %; $\Delta UH_{NS}$ in the range of 0.1-10 mole %; $\Delta U_{2S}H_{NAc}$ in the range of 0.1-5 mole %; $\Delta UH_{NAc,6S}$ in the range of 0.1-15 mole %; and $\Delta UH_{NAc,6S}GH_{NS,3S,6S}$ in the range of 0.1-20 mole %. In some embodiments, the LMWH composition further comprises greater than 30 IU/mg anti-IIa activity.

In other aspects, the invention relates to a composition including a mixed population of polysaccharides, such as glycosaminoglycans (GAGs), HLGAGs, UFH, FH, LMWHs or synthetic heparins including but not limited to enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™) or Fondaparinux (Arixtra™) with less batch-batch variability.

In other aspects, the invention relates to a composition including a mixed population of polysaccharide, such as glycosaminoglycans (GAGs), HLGAGs, UFH, FH, or LMWHs where the anti-Xa activity can be fully neutralized by protamine, e.g., the anti-Xa activity can be neutralized by ≥50%.

In other aspects, the invention relates to a composition including a mixed population of polysaccharides, such as glycosaminoglycans (GAGs), HLGAGs, UFH, FH, or LMWHs where the anti-IIa activity can be fully neutralized, e.g., the anti-IIa activity can be neutralized by ≥70%.

In other aspects, the invention relates to a composition including a mixed population of polysaccharides, such as glycosaminoglycans (GAGs), HLGAGs, UFH, FH, or LMWHs where the composition has lower PF4 binding sequences.

In other aspects, the invention relates to a composition including a mixed population of polysaccharides, such as glycosaminoglycans (GAGs), HLGAGs, UFH, FH, or LMWHs where the process to make the composition has been optimized to ensure lower PF4 binding sequences. In some embodiments, the composition includes reduced amounts of peak 1, peak 2, peak 4, and/or peak 6 relative to UFH, e.g., peak 1, $\Delta U_{2S}H_{NS,6S}$ (e.g., less than about 50 mole %, e.g., 15-30 mole %); peak 2, $\Delta U_{2S}H_{NS}$ (e.g., less than about 5 mole %, e.g., 1.8-3.5 mole %); peak 4, $\Delta U_{2S}H_{NAC,6S}$ (e.g., less than about 2 mole %, e.g., 0.1-1.0 mole %); and/or peak 6, $\Delta U_{2S}H_{NAC}$ (e.g., less than about 2 mole %, e.g., 0.1-0.5 mole %).

In other aspects, the invention relates to compositions made by the methods of the invention including ultra-low molecular weight heparins (ULMWHs) comprising 15-20 monosaccharide units, optionally with binding affinity (Kd) for ATIII of 1-60 nM, anti-Xa activity of 5-30 nm (IC50) and/or anti-IIa activity of 0.5-100 or greater than 500 nM (IC50). These ULMWHs may also be susceptible to neutralization by protamine and/or substantially free of binding affinity for PF4.

In other aspects, the invention relates to compositions made by the methods of the invention including comprising LMWHs with mean molecular weight from 1500-3000 D, anti-Xa activity in the range of 94-150 IU/mg, preferably 125-150 IU/mg, more preferably 140-150 IU/mg; anti-IIa of ≤10 IU/mg, preferably ≤5 IU/mg; and an anti-Xa:anti-IIa activity ratio greater than 10:1, preferably greater than 25:1, optionally including at least one sulfated polysaccharide of heparin having 2-26 saccharide units.

In other aspects, the invention relates to a LMWH composition comprising a tag. In some embodiments, the tag emits detectable electromagnetic radiation. In some embodiments, the tag is a fluorescent label, a mass-label compatible with mass-spectrometric methods, O18, yttrium, 3H, affinity label, pH sensitive label, or radioactive label. In another aspect, the invention provides a method of evaluating a sample for the presence of a LMWH comprising a tag comprising the steps of providing a sample; optionally purifying the sample; and determining the presence of the tag in the sample. In some embodiments, the method also includes the step of determining the level of the tag. In some embodiments, the sample is from a subject, e.g., a human or veterinary subject or an experimental animal as described herein, receiving the LMWH comprising a tag. In some embodiments, the LMWH is M118, M115, M411, M108, M405, M312, enoxaparin; dalteparin; certoparin; ardeparin; nadroparin; parnaparin; reviparin; tinzaparin, or fondaparinux. In some embodiments, the sample is a bodily fluid, e.g., blood, blood plasma, and/or urine. In another aspect, the invention includes a kit for performing a method for evaluating a sample for the presence of a LMWH as described herein, including one or more of the following: a tag; a compound for attaching the tag to a polysaccharide, and a standard, e.g., a polysaccharide or a tagged polysaccharide.

The invention also relates to LMWH compositions comprising a marker or tag; in a preferred embodiment, the invention relates to LMWHs comprising a marker or tag that can be detected using an ELISA or chromogenic assay. In a preferred embodiment, the marker or tag may be an antibody, fluorescent label, a mass-label compatible with mass-spectrometric methods, an affinity label, a radioactive label, UV label, NMR label, ESR or EPR spin label, or other chromophore. In a further preferred embodiment, the marker or tag may be attached to a component of the LMWH having biological activity. In a related aspect, the invention relates to methods of monitoring a subject receiving a LMWH having a marker or tag, the method comprising monitoring the subject for the presence and/or levels of the marker or tag, preferably in the bodily fluid of the subject. The invention further relates to a kit for detecting such a marker or tag.

The compositions of the invention may be derived from a natural source or may be synthetic. In some embodiments, the natural source is porcine intestinal mucosa.

The compositions may be formulated for in vivo delivery in some embodiments. For instance, the preparation may be formulated for inhalation, oral, subcutaneous, intravenous, intraperitoneal, transdermal, buccal, sublingual, parenteral, intramuscular, intranasal, intratracheal, ocular, vaginal, rectal, transdermal, and/or sublingual delivery.

Optionally, the compositions may also include one or more additives. Additives include, but are not limited to, dermatan sulfate, heparan sulfate or chondroitin sulfate.

In some embodiments of the invention, the preparation includes a specific amount of heparin. For instance the preparation may include 80-100 mole % heparin, 60-80 mole % heparin, 40-60 mole % heparin, or 20-40 mole % heparin. The heparin may, for example, be LMWH, native heparin, heparin sulfate, biotechnology-derived heparin, chemically modified heparin, synthetic heparin or heparin analogues.

In other aspects, the invention relates to methods for treating or preventing disease using the compositions of the invention. For instance, the invention includes methods for treating or preventing a condition in a subject wherein the subject has or is at risk of a disorder selected from the group consisting of: disease associated with coagulation, such as thrombosis, cardiovascular disease, vascular conditions or atrial fibrillation;

migraine, atherosclerosis; an inflammatory disorder, such as autoimmune disease or atopic disorders; an allergy; a respiratory disorder, such as asthma, emphysema, adult respiratory distress syndrome (ARDS), cystic fibrosis, or lung reperfusion injury; a cancer or metastatic disorder, an angiogenic disorder, such as neovascular disorders of the eye, osteoporosis, psoriasis, and arthritis; Alzheimer's; bone fractures such as hip fractures; or is undergoing or having undergone surgical procedure, organ transplant, orthopedic surgery, hip replacement, knee replacement, percutaneous coronary intervention (PCI), stent placement, angioplasty, coronary artery bypass graft surgery (CABG). The compositions of the invention are administered to a subject having or at risk of developing one or more of the diseases in an effective amount for treating or preventing the disease.

In other aspects, the invention relates to a method for treating or preventing disease using different and specific novel LMWHs with specific product profiles at different phases in the course of treatment of a patient by dosing the patient with a LMWH having an enhanced activity for a specific disease state, e.g., a high level of anti-Xa or -IIa activity and than dosing with another LMWH composition having an enhanced activity for the changed disease state, e.g., having decreased PF4 binding.

In some aspects, the invention provides a method of treating a subject, e.g. a human or veterinary subject. The method includes some or all of the following: providing a panel of two or more LMWH preparations having different ratios of anti-IIa activity and anti-Xa activity; selecting a LMWH preparation having a desired ratio; and administering one or more doses of a therapeutically effective amount of the LMWH preparation to the subject.

In some embodiments, the method also includes monitoring the levels of LMWH in the subject, e.g., repeatedly monitoring the levels of LMWH in the subject over time. In some embodiments, the method includes adjusting the doses of the LMWH preparation. In some embodiments, the method includes monitoring the status of the subject in response to the administration of the LMWH preparation. In some embodiments, the method monitoring the status of the subject over a period of time. In some embodiments, the method also includes administering a different LMWH preparation based on changes in the status of the subject over time. In another aspect, the invention features a method of inhibiting coagulation in a patient by administering one or more doses of a therapeutic amount of a LMWH preparation described herein having high anti-Xa and anti-IIa activity, monitoring the status of the subject, then administering one or more doses of a therapeutic amount of a LMWH preparation as described herein having high anti-Xa activity alone. In some embodiments, the method includes providing or determining the structural signature of the LMWH preparation, and optionally correlating the status of the subject to the structural signature of the LMWH.

In another aspect, the invention provides a method of treating a subject who has previously been diagnosed with HIT, comprising administering to the subject a therapeutically effective dose of a composition described herein having decreased PF4 binding activity.

In another aspect, the invention provides a method for determining the safety or suitability of a heparin for use in a particular indication. The method includes some or all, typically all, of the following: providing the structural signature of the heparin; providing a reference structural signature; determining if the heparin is acceptable, e.g., by comparing the structural signature of the heparin with the reference structural signature; where a preselected index of similarity is met, the heparin is safe or suitable. In some embodiments, the reference structural signature is associated with one or more undesired effects. In some embodiments, the reference structural signature is associated with one or more desired effects. In a preferred embodiment, the safety or suitability of the heparin is determined based on the level of peak 1, 2, 4, and/or 6 present in the sample; e.g., batches with lower levels of one or more of peak 1, 2, 4, and/or 6 are safer than batches with higher levels.

In another aspect, the invention provides a method of making one or more batches of a LMWH preparation which has a batch-to-batch variation of a preselected range from a preselected value for one or more-component saccharide chosen from the group consisting of $\Delta U_{2S}H_{NS,6S}$; $\Delta U_{2S}H_{NS}$; $\Delta UH_{NS,6S}$; $\Delta U_{2S}H_{NAC,6S}$; $\Delta UH_{NS}$; $\Delta U_{2S}H_{NAC}$; $\Delta UH_{NAC,6S}$; and $\Delta UH_{NAc,6S}GH_{NS,3S,6S}$. The method includes some or all, typically all of the following: selecting a desired value; providing an aliquot of UFH; optionally fractionating the aliquot; determining the level of the component in the aliquot; and selecting a batch or batches with less than the preselected range of variation from the desired value. In some embodiments, the preselected variation is less than 2.5%, more preferably less than 2% or less than 1%. In some embodiments, the preselected variation for p1 is less than 3%, less than 2%, or less than 1%. In some embodiments, the preselected variation for p2 is less than 16%, less than 15%, less than 11%, less than 10%, less than 5%, less than 1%. In some embodiments, the preselected variation for p3 is less than 8%, less than 4%, less than 2%, less than 1%. In some embodiments, the preselected variation for p4 is less than 22%, less than 15%, less than 10%, less than 5%, less than 1%. In some embodiments, the preselected variation for p5 is leas than 3%, less than 2%, or less than 1%. In some embodiments, the preselected variation for p6 is less than 10%, less than 5%, less than 2%, less than 1%. In some embodiments, the preselected variation for p7 is less than 90%, less than 75%, less than 50%, less than 25%, less than 10%, less than 5%. In some embodiments, the preselected variation for p8 is less than 12%, less than 10%, less than 8%, less than 5%, less than 4%, less than 2%.

In another aspect, the invention provides a method of making one or more batches of a LMWH preparation which has a batch-to-batch variation of less than a preselected range from a preselected value, e.g., less than 2.5%, more preferably less than 2% or less than 1%, for one or more component saccharide chosen from the group consisting of p1-p8. The method includes some or all, typically all, of the following: selecting a value; providing an aliquot of UFH or LMWH; precipitating the aliquot; optionally subjecting the aliquot to an ion exchange process; and contacting the aliquot with an agent under conditions such that the desired value will result. In some embodiments, the agent is a heparin degrading enzyme chosen from the group consisting of heparinase I, heparinase II, heparinase III, and functionally active variants and fragments thereof. In some embodiments, the agent is a chemical, e.g., a chemical chosen from the group consisting of $H_2O$, $Cu^+$ and $H_2O_2$, isoamyl nitrite, nitrous acid, benzyl ester or alkaline treatment. In another aspect, the invention provides a composition comprising multiple batches of a LMWH preparation prepared by the method described herein. In another aspect, the invention provides a composition comprising a LMWH preparation prepared by a method described herein.

In another aspect, the invention provides a composition comprising multiple batches of a LMWH preparation, wherein, the for each of the batches, the mole % of one or more component chosen from the group consisting of p1-p8 varies less than a preselected variation, e.g., less than 2.5%, more preferably less than 2% or less than 1%.

In another aspect, the invention provides a composition comprising multiple batches of a LMWH preparation, wherein the glycoprofile of each of the batches for one or more component chosen from the group consisting of p9-p10 varies less than a preselected variation, e.g., less than 2.5%, more preferably less than 2% or less than 1%.

In another aspect, the invention also provides methods for adjusting the dose of a batch of a LMWH to be administered, e.g., depending on the glycoprofile of the LMWH. For example, the dose may be adjusted depending on the level of a peak, e.g., peaks 1, 2, 4, 6, and/or 8. In a preferred embodiment, the dose of the batch is adjusted based on the level of peak 8 present in the batch.

In another aspect, the invention provides a record, e.g., a computer readable record, having an element which identifies a polysaccharide, e.g., UFH or LMWH, an element which identifies one or more components of the polysaccharide, and an element which identifies a range of mole % of the components.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Figure 1A:
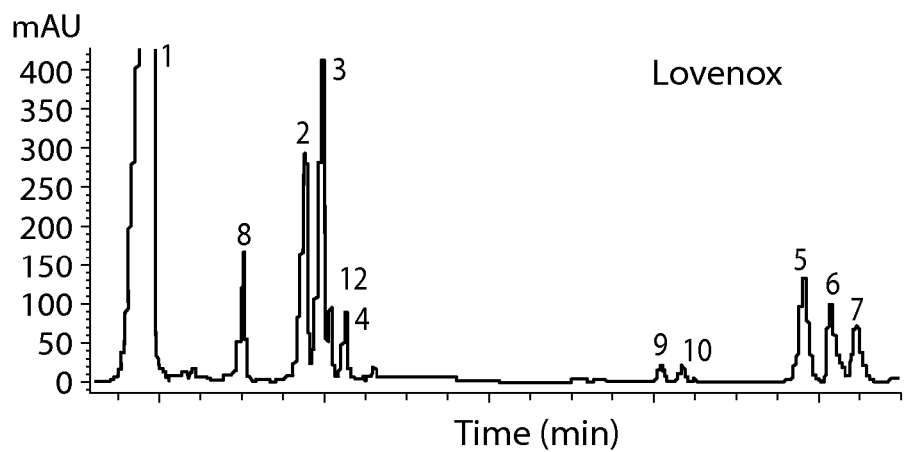
FIG. 1A. Capillary electrophoresis (CE) profile of enoxaparin (Lovenox™). The different building blocks are labeled as 1, 2, 3 etc., corresponding to the different peaks.

The invention involves significant advances in methods of analysis and monitoring of polysaccharides, particularly sulfated polysaccharides such as heparin and LMWHs, and improved compositions for therapeutic treatment. For instance, it has been discovered that the methods described herein can be used to analyze compositions of sulfated GAGs including HLGAGs such as UFH and LMWH, and to create a set of primary and secondary outputs referred to herein as a "structural signature" that indicates, inter alia, the composition and structure of a preparation and can be used to predict the activity of the composition. Further, this information can be used to standardize the production of LMWH compositions, thus resulting in LMWHs with less batch-batch variability and improved ratios of desirable and undesirable activities. For instance, polysaccharides having a high anti-Xa activity are particularly useful for treating coagulation disorders and cardiovascular disease, such as pulmonary embolism, acute myocardial infarction or unstable angina. In addition, polysaccharides having reduced PF4 binding are desirable.

It has also been discovered that polysaccharides having a low anti-Xa activity are particularly useful for treating atherosclerosis, respiratory disorder, a cancer or metastasis, inflammatory disorder, allergy, angiogenic disorder, and/or lung, kidney, heart, gut, brain, or skeletal muscle ischemial-reperfusion injuries. Respiratory disorders include but are not limited to asthma, emphysema, and adult respiratory distress syndrome (ARDS). Angiogenic disorders include but are not limited to neovascular disorders of the eye, osteoporosis, psoriasis, and arthritis. Thus, it is possible to tailor a compounds which would be particularly useful for treating a subject that is preparing to undergo, is undergoing or is recovering from a surgical procedure or is undergoing a tissue or organ transplant. Surgical procedures include but are not limited to cardiac-pulmonary by-pass surgery, coronary revascularization surgery, orthopedic surgery, prosthesis replacement surgery, treatment of fractures including hip fractures, PCI, hip replacement, knee replacement, and stent placement or angioplasty.

It has also been discovered that a polysaccharide having a high anti-IIa activity has beneficial therapeutic properties; for instance, when delivered via a pulmonary delivery system, the rapid onset of action of polysaccharides having high anti-IIa activity is useful in treating acute conditions. Thus the instant invention relates to compositions with high anti-IIa activity for use in treatment of acute cardiac syndrome and myocardial infarction.

It was previously believed in the prior art that a high anti-IIa activity was not desirable for therapeutic purposes. As a result, polysaccharide preparations may have been selected based on a low anti-IIa activity. The compositions of the invention include polysaccharide compositions designed to have either a high or low anti-IIa activity without regards to the sequence. The compositions of the invention include polysaccharide compositions designed to have a high anti-IIa activity and sequence specific low anti-IIa activity and methods of using these compositions. For instance, compositions having higher anti-IIa activity (e.g., M118 and M312) are more potent for indications such as arterial thrombosis (including ST elevation, MI and acute coronary syndrome (ACS)) than LMWHs which possess lower anti-IIa activity.

A "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide).

It had been found that some polysaccharides have therapeutic activity. In particular, heparin is a widely used clinical anticoagulant. Heparin primarily elicits its effect through two mechanisms, both of which involve binding of antithrombin III (AT-III) to a specific pentasaccharide sequence, $H_{NAc/S,6S}GH_{NS,3S,6S}I_{2S}H_{NS,6S}$ contained within the polymer. First, AT-III binding to the pentasaccharide induces a conformational change in the protein that mediates its inhibition of factor Xa. Second, thrombin (factor IIa) also binds to heparin at a site proximate to the pentasaccharide AT-III binding site. Formation of a ternary complex between AT-III, thrombin and heparin results in inactivation of thrombin. Unlike its anti-Xa activity that requires only the AT-III pentasaccharide-binding site, heparin's anti-IIa activity is size-dependant, requiring at least 18 saccharide units for the efficient formation of an AT-III, thrombin, and heparin ternary complex. Additionally, heparin also controls the release of TFPI through binding of heparin to the endothelium lining the circulation system. Favourable release of TFPI, a modulator of the extrinsic pathway of the coagulation cascade, also results in further anticoagulation. In addition to heparin's anticoagulant properties, its complexity and wide distribution in mammals have lead to the suggestion that it may also be involved in a wide range of additional biological activities.

Although heparin is highly efficacious in a variety of clinical situations and has the potential to be used in many others, the side effects associated with heparin therapy are many and varied. Side effects such as heparin-induced thrombocytopenia (HIT) are primarily associated with the long chain of unfractionated heparin (UFH), which provides binding domains for various proteins. This has led to the generation and utilisation of low molecular weight heparin (LMWH) as an efficacious alternative to UFH. As a result, numerous strategies have been designed to create novel LMWHs with reduced chain lengths and fewer side effects. Of particular interest is the design of LMWHs that constitute the most active biological fragments of heparin. Examples of biologically active portions of a polysaccharide include but are not limited to a tetrasaccharide of the AT-III biding domain of heparin, a tetrasaccharide of the FGF biding domain of heparin, $I/GH_{NAc,6S}GH_{NS,3S,6S}$, $I/GUH_{NS,6S}GH_{NS,3S,6S}$, $I/GUH_{NAc,6S}GH_{NS,3S}$, or $I/GUH_{NS/6S}GH_{NS,3S}$. In other aspects, it is of interest to design LMWHs that have reduced portions that have or are associated with an unwanted biological activity, e.g., PF4 binding, e.g., $\Delta U_{2S}H_{NS,6S}$ (peak 1); $\Delta U_{2S}H_{NS}$ (peak 2); $\Delta U_{2S}H_{NAc,6S}$ (peak 4); and/or $\Delta U_{2S}H_{NAc}$ (peak 6).

Sulfated polysaccharide preparations having structural and functional properties similar to LMWHs have been constructed and have been found to possess anti-Xa and anti-IIa activity as well as to promote the release of TFPI. Because of these attributes, the structure of these novel sulfated polysaccharide preparations could be assessed in conjunction with the beneficial activity. As shown below, the novel sulfated polysaccharide preparations of the invention demonstrate increased anti-Xa and anti-IIa activity or reduced IIa activity as well as TFPI release relative to UFH and other LMWHs. These novel LMWHs, likewise, contain a higher mole % of peak 8. It has also been found that the mole % of peak 8 is linearly correlated with anti-Xa and anti-IIa activity. It has also been shown that the novel polysaccharides have reduced PF4 binding activity. These novel LMWH have a lower mole % of $\Delta U_{2S}H_{NS,6S}$ (peak 1); $\Delta U_{2S}H_{NS}$ (peak 2); $\Delta U_{2S}H_{NAc,6S}$ (peak 4); and/or $\Delta U_{2S}H_{NAc}$ (peak 6).

Mole % of a polysaccharide (e.g., a tetrasaccharide, a trisaccharide, a disaccharide, etc.) in this invention refers to the percentage of the number of moles of the polysaccharide in the sample, where one mole is $6.02 \times 10^{23}$ molecules. In other words, mole % is also simply the number of molecules of the polysaccharide divided by the number of molecules present in the sample multiplied by 100.

It has also been discovered that the presence of the tetrasaccharide in the non-reducing end of the heparin sequence results in high anti-IIa activity. In the past, it was believed that this positioning of the tetrasaccharide would result in a composition having low anti-IIa activity. Compositions have been developed herein that have a predominant amount of the tetrasaccharide in the non-reducing end of the heparin sequence and have high anti-IIa activity.

Therefore, the invention relates to compositions of sulfated polysaccharides containing a useful amount of a beneficial feature such as a tetrasaccharide fragment represented by peak 8 and methods of treatment using compositions comprising peak 8.

Polysaccharide mixtures containing heterogeneous populations of heparin sequences can be fractionated into heparin of a specific size by varying the conditions described herein for temperature, solvent, and enzyme. The LMWH obtained by this procedure has high activity for anticoagulation, and low amount of the highly sulfated disaccharide represented by peak 1 (<70 mole %). In general, the higher molecular weight and/or higher charge fraction will precipitate at higher temperature, with a lower amount of polar solvent such as ethanol or acetone. Decreasing the temperature, and/or increasing the amount of polar solvent may result in the precipitation of the fraction with lower molecular weight, lower charge, and higher anticoagulation activity. Using the methods disclosed herein, the precipitation parameters may be altered without undue experimentation by one of ordinary skill in the art to obtain a preparation that conforms with the desired product.

Following the selective precipitation, the second fraction, the LMWH fraction, is processed to produce a sulfated polysaccharide preparation containing a specific amount of the tetrasaccharide represented by peak 8 as defined earlier. The processing step may involve an enzymatic or chemical digestion to yield the concentrated tetrasaccharides useful in the sulfated polysaccharide preparation. In one embodiment, the fraction is digested and the enzyme used in the digestion is Heparinase I or a functionally active variant or fragment thereof. In another embodiment the fraction is digested and the enzyme used in the digestion is Heparinase II or a functionally active variant or fragment thereof. In another embodiment, the fraction is digested and the enzyme used in the digestion is Heparinase III or a functionally active variant or fragment thereof. In another embodiment, the fraction is digested and the enzyme used in the digestion is Heparinase IV or a functionally active variant or fragment thereof. In another embodiment, the fraction is digested and the enzyme used in the digestion is mammalian Heparanase or a functionally active variant or fragment thereof. In yet another embodiment, the fraction is digested and the enzyme used in the digestion is a mixture of one or more of Heparinase I, II, III, IV and Heparanase or a functionally active variant or fragment thereof. The term "heparinase" is used generically to encompass functionally active variants and fragments thereof in addition to the native heparinases, and includes bacterial and recombinant heparinases I, II, III, IV and heparanase, among others. Several patents and patent applications describe useful modifications and variants and fragments of heparinase, including U.S. Pat. No. 6,217,863 B1 and pending application Ser. Nos. 09/384,959 and 09/802,285. Heparinase (as defined above) causes depolymerization of heparin. Depending upon the concentration of heparinase used, and the period for which it is used (partial vs exhaustive digestion), heparin of specific molecular weight, and/or charge is obtained. As an example, which is not intended to be limiting, a partial digestion of heparin with 1 molar equivalent of heparinase would result in a fraction of higher molecular weight, and/or higher charge than would a reaction with a longer digestion time. Also, increasing the molar equivalence of heparinase will result in a fraction with lower molecular weight and/or lower charge than if a lower molar equivalence of heparinase is used. In some embodiments, heparinase concentrations and length of digestions can be used in combination with salt, temperature, and solvent composition, as described herein, to obtain heparin of specific molecular weight, charge and/or biological activity.

Alternatively, following the selective precipitation, the LMWH fraction may be chemically degraded to yield the concentrated sulfated polysaccharide preparation. The fraction can be chemically degraded using a method selected from the group including but not limited to: oxidative depolymerization with $H_2O_2$ or $Cu^+$ and $H_2O_2$, deaminative cleavage with isoamyl nitrite, or nitrous acid, β-eliminative cleavage with benzyl ester of heparin by alkaline treatment or by heparinase.

Alternatively, the tetrasaccharide/peak 8 containing sequences may be produced synthetically. Examples of methods for synthesizing polysaccharides synthetically include U.S. Patent Application Ser. No. 60/263,621, filed Jan. 23, 2001, entitled: "Solid- and Solution-phase Synthesis of Heparin and Other Glycosaminoglycans" and U.S. patent application Ser. No. 09/413,381, filed on Oct. 6, 1999, entitled: "Synthesis Of Oligosaccharides In Solution And On The Solid Support" by Obadiah J. Plante and Peter H. Seeberger, the entire contents of which are incorporated by reference.

The sulfated polysaccharides may in some embodiments be substantially pure. As used herein, the term "substantially pure" means that the polysaccharides are essentially free of other substances to an extent practical and appropriate for their intended use. In particular, the polysaccharides are sufficiently pure and are sufficiently free from other biological constituents of their hosts environments, e.g., having less than 20%, 15%, 10%, 5%, 2%, or 1% of other biological constituents from the host environment, so as to be useful in, for example, producing pharmaceutical preparations.

In some cases the composition, whether substantially pure or not, may also include other compounds such as one or more heparin molecules. As used herein the term "heparin" refers to polysaccharides having heparin-like structural and functional properties. Heparin includes, but is not limited to, native heparin, low molecular weight heparin (LMWH), heparin, biotechnologically prepared heparin, chemically modified heparin, synthetic heparin, and heparan sulfate. The term "biotechnological heparin" or "biotechnologically prepared heparin" encompasses heparin that is prepared from natural sources of polysaccharides which have been chemically modified and is described in Razi et al., Bioche. J. 1995 Jul. 15; 309 (Pt 2): 465-72. Chemically modified heparin is described in Yates at al., Carbohydrate Res (1996) Nov. 20; 294:15-27, and is known to those of skill in the art. Synthetic heparin is well known to those of skill in the art and is described in Petitou, M. et al., Bioorg Med Chem Lett. (1999) Apr. 19; 9(8):1161-6. Native heparin is heparin derived from a natural source (such as porcine intestinal mucosa).

The compositions of this invention may also be formulated with additives. An "additive" as used herein may be a carrier molecule. These additives may or may not have biological activity. In the instance where the additives elicit biological activity, the activity may be complementary. That is, it may be useful for the same therapeutic purpose as the sulfated polysaccharide preparation. Additives may also have some specific function, such as tumor cell growth inhibition, but in general it is preferable that the additive not have a conflicting effect on the coagulation cascade. These additives may be polysaccharides such as dermatan sulfate, heparan sulfate and chondroitin sulfate and/or proteins, such as albumin. Other additives are known to those of skill in the art.

As shown below, the sulfated polysaccharides produced according to the invention have improved functional properties over prior art heparin and LMWH preparations. The ability to prepare a composition having a specific minimum amount of a structural signature output, e.g., the tetrasaccharides $I/GH_{NAC,6S}GH_{NS,3S,6S}$, (represented by $\Delta UH_{NAC,6S}GH_{NS,3S,6S}$) $I/GH_{NS,6S}GH_{NS,3S,6S}$ (represented by $\Delta UH_{NS,6S}GH_{NS,3S,6S}$); $I/GH_{NAC,6S}GH_{NS,3S}$ (represented by $\Delta UH_{NAC,6S}GH_{NS,3S}$); or $I/GH_{NS,6S}GH_{NS,3S}$ (represented by $\Delta UH_{NS,6S}GH_{NS,3S}$)(or related compounds), is advantageous because these compositions have dramatically improved therapeutic properties. The ability to prepare a composition having a specific maximum amount of a structural signature output, e.g., $\Delta U_{2S}H_{NS,6S}$ (peak 1), $\Delta U_{2S}H_{NS}$ (peak 2), $\Delta U_{2S}H_{NAC,6S}$ (peak 4), and/or $\Delta U_{2S}H_{NAC}$ (peak 6), is advantageous because these compositions have reduced PF4 binding and this reduced likelihood of causing HIT. Thus, the compositions of the invention may include a preparation that has a structural signature very similar to that of a commercially available LMWH preparation such as enoxaparin, with an improvement, e.g., the addition of a desirable element, an increase in a desirable element, a decrease in an undesirable element, the elimination of an undesirable element and/or a reduction in batch to batch variability.

The structure of polysaccharides which are useful in the methods of the invention can be identified using techniques known in the art. The sequence of several polysaccharides has been identified using a property-encoded nomenclature/mass spectrometry scheme (PEN-MALDI), a sequencing methodology described in U.S. patent application Ser. Nos. 09/557, 997 and 09/558,137 filed on Apr. 24, 2000, which are incorporated herein by reference in their entirety, and Venkataraman, G., Shriver, Z., Raman, R. & Sasisekharan, R. (1999) *Science* 286, 537-42. Using these techniques, the characteristics of a polysaccharide can be identified by any means which is consistent with the experimental constraint used. Molecular weight may be determined by several methods including mass spectrometry. The use of mass spectrometry for determining the molecular weight of polysaccharides is well known in the art. Mass spectrometry has been used as a powerful tool to characterize polysaccharides because of its accuracy (±1 Dalton) in reporting the masses of fragments generated (e.g., by enzymatic cleavage), and also because only pM sample concentrations are required. For example, matrix-assisted laser desorption ionization mass spectrometry (MALDI-MS) has been described for identifying the molecular weight of polysaccharide fragments in publications such as Rhomberg, A. J. et al, *PNAS, USA, v.* 95, p. 4176-4181 (1998); Rhomberg, A. J. et al, *PNAS*, USA, v. 95, p. 12232-12237 (1998); and Ernst, S. et. al., *PNAS*, USA, v. 95, p. 4182-4187 (1998), each of which is hereby incorporated by reference. Other types of mass spectrometry known in the art, such as, electron spray-MS, fast atom bombardment mass spectrometry (FAB-MS) and collision-activated dissociation mass spectrometry (CAD) can also be used to identify the molecular weight of the polysaccharide fragments.

The mass spectrometry data may be a valuable tool to ascertain information about the polysaccharide component isolated from natural sources or synthesized without further treatment or after the polysaccharide has undergone degradation with enzymes or chemicals. After a molecular weight of a polysaccharide is identified, it may be compared to molecular weights of other known polysaccharides (e.g., using the methods of U.S. patent application Ser. Nos. 09/557,997 and 09/558,137, which are incorporated herein by reference in their entirety). As shown in these patent applications, one technique for comparing molecular weights is to generate a mass line and compare the molecular weight of the unknown polysaccharide to the mass line to determine a subpopulation of polysaccharides which have the same molecular weight. A "mass line" is an information database, preferably in the form of a graph or chart which stores information for each possible type of polysaccharide having a unique sequence based on the molecular weight of the polysaccharide. Because mass spectrometry data indicates the mass of a fragment to 1 Da accuracy, a length may be assigned uniquely to a fragment by looking up a mass on the mass line. Further, it may be determined from the mass line that, within a fragment of a particular length higher than a disaccharide, there is a minimum of 4.02 Da different in masses indicating that two acetate groups (84.08 Da) replaced a sulfate group (80.06 Da). Therefore, a number of sulfates and acetates of a polysaccharide fragment may be determined from the mass from the mass spectrometry data and, such number may be assigned to the polysaccharide fragment. In addition to molecular weight, other properties of a polysaccharide may be determined to fully characterize the polymer.

In a preferred embodiment, capillary electrophoresis (CE) is used to identify the disaccharide/tetrasaccharides building blocks. CE is superior to SAX HPLC in oligosaccharide analysis for several reasons. CE is significantly more accurate and precise than traditional LC due to the fact that there is no peak broadening resulting from laminar flow (as is the case with LC). The use of CE allows for 100% mass balance of di- and oligosaccharides after heparinase digestion. As a result, it is possible to resolve all of the lower prevalence oligosaccharides that are responsible for many of the clinical characteristics of heparins. In addition, CE requires the injection of 20 to 100 fold smaller amounts of saccharides compared to LC (500 fmols or less vs. at least 10 pmoles for capillary LC). Also, due to a larger number of theoretical plates, the resolving power of CE is higher than LC enabling separation of unique products (isomers) that contain an identical number of sulfates over a short run time. Thus the use of CE makes it possible to resolve all 32 building blocks that make up heparins.

CE also affords an added degree of flexibility in terms of complementarity to other analytical methodologies, including MALDI MS. In a further embodiment, the method of the invention relates to the use of CE separation and analysis followed by off-line MALDI MS analysis to derive structural information in an iterative way using bioinformatics.

Finally, the methods of the invention include the use of several techniques, including MALDI-MS, ESI-MS, CE and NMR, in combination to corroborate findings with respect to the structural signature of oligosaccharides. The methods of the invention make it possible to isolate, identify, and assign all the saccharide products that arise in a CE electrophoretogram of both heparin and various low LMWHs, including various 3-O-sulfated saccharides which are crucial for certain therapeutic utilities.

A further advantage of the methods of the invention is sensitivity; the methods make it possible to detect and characterize heparin samples down to a concentration range of 0.2-1 mg/mL.

Once a polysaccharide sample is characterized, the activity may be assessed in vitro or in vivo. Methods of determining the activity of sulfated polysaccharide preparations was assessed and shown in the Examples below. It was found that these preparations possessed a higher mole % of peak 8. The mole % of peak 8 was shown to be a good predictor of anticoagulation activity as the mole % of the tetrasaccharides were linearly correlated to both anti-IIa and anti-Xa activity. Additionally in vivo experiments further described in the Examples demonstrated anti-Xa and anti-IIa activity as well as increased TFPI release. Therefore, the compositions of the invention may be constructed and assessed according to the content of peak 8 as well as other fragments which may prove to be biologically important, e.g., $\Delta U_{2S}H_{NS,6S}$ (peak 1); $\Delta U_{2S}H_{NS}$ (peak 2); $\Delta U_{2S}H_{NAC,6S}$ (peak 4); and/or $\Delta U_{2S}H_{NAC}$ (peak 6) which are associated with PF4 binding. The molar amount of these fragments in a sample are indicative of desirable activity and can be used in compositions and methods of treatment for diseases as will be described below. Furthermore, the molar amounts of these fragments may be used to predict what biological activity and levels of activity a given heparin compound will have, without the need for performing direct biological assays; thus, the method provides a way to both streamline manufacturing and reduce costs while ensuring a more consistent, higher quality product.

This information may be used to determine bioequivalence as well; by the following method, which is intended solely as an example and is not meant to be limiting. First, a reference standard is selected, and information about the composition and biological activity of a drug, e.g., how it is used and cleared by the body, is either provided or determined. They can be determined by any method, including the methods of the invention. The reference standard may be a previously characterized composition, or a new reference standard may be determined. Taking a LMWH preparation as an example, the reference standard would include information regarding the absorption of the preparation into the body; the clearance rates of the preparation out of the body; and the structural signature of the preparation. The same information is either provided or determined for one or more target compositions, and the two (or more) are compared; bioequivalence is determined by the variance between the two. Thus, the invention also relates to a method for determining bioequivalence.

The compositions may be administered therapeutically to a subject. As used herein, a "subject" is a human or non-human vertebrate such as a non-human primate, cow, horse, pig, sheep, goat, dog, cat, or rodent.

The compositions of the invention have many therapeutic utilities, and generally may be used for the treatment of any type of condition in which heparin, LMWH, or synthetic heparin therapy has been identified as a useful therapy. For instance, the invention includes methods for treating or preventing wherein the subject has or is at risk of a disorder selected from the group consisting of disease associated with coagulation, such as thrombosis, cardiovascular disease, vascular conditions or atrial fibrillation; migraine, atherosclerosis; an inflammatory disorder, such as autoimmune disease or atopic disorders; an allergy; a respiratory disorder, such as asthma, emphysema, adult respiratory distress syndrome (ARDS), cystic fibrosis, or lung reperfusion injury; a cancer or metastatic disorder; an angiogenic disorder, such as neovascular disorders of the eye, osteoporosis, psoriasis, and arthritis, Alzheimer's; bone fractures such as hip fractures; or is undergoing or having undergone surgical procedure, organ transplant, orthopedic surgery, hip replacement, knee replacement, percutaneous coronary intervention (PCI), stent placement, angioplasty, coronary artery bypass graft surgery (CABG).

Thus, the invention is useful in a variety of in vitro, in vive and ex vivo methods in which LMWH therapies are useful. For instance, it is known that LMWH compositions are useful for preventing coagulation, inhibiting cancer cell growth and metastasis, preventing angiogenesis, preventing neovascularization, and preventing psoriasis. Each of these disorders is well-known in the art and is described, for instance, in *Harrison's Principles of Internal Medicine* (McGraw Hill, Inc., New York), which is incorporated herein by reference.

When an imbalance in the coagulation pathway shifts towards excessive coagulation, the result is the development of thrombotic tendencies, which are often manifested as heart attacks, strokes, deep venous thrombosis, acute coronary syndrome, unstable angina and myocardial infarcts. A "disease associated with coagulation" as used herein refers to a condition characterized by local inflammation which may result in an interruption or reduction in the blood supply to a tissue which may occur, for instance, as a result of blockage of a blood vessel responsible for supplying blood to the tissue such as is seen for myocardial or cerebral infarction or peripheral vascular disease, or as a result of emboli formation associated with conditions such as atrial fibrillation or deep venous thrombosis. Coagulation disorders include, but are not limited to, cardiovascular disease and vascular conditions such as cerebral ischemia.

The methods are useful for treating cardiovascular disease. Cardiovascular diseases include, but are not limited to, acute myocardial infarction, unstable angina, acute coronary syndrome and atrial fibrillation. Myocardial infarction is a disease state which sometimes occurs with an abrupt decrease in coronary blood flow that follows a thrombotic occlusion of a coronary artery previously narrowed by atherosclerosis. Such injury may be produced or facilitated by factors such as cigarette smoking, hypertension, and lipid accumulation. Acute angina is due to transient myocardial ischemia. This disorder is usually associated with a heaviness, pressure, squeezing, smothering, or choking feeling below the sternum. Episodes are usually caused by exertion or emotion, but can occur at rest.

Atrial fibrillation is a common form of arrhythmia generally arising as a result of emotional stress or following surgery, exercise, or acute alcoholic intoxication. Persistent forms of atrial fibrillation generally occur in patients with cardiovascular disease. Atrial fibrillation is characterized by disorganized atrial activity without discrete P waves on the surface ECG.

Persons undergoing surgery, anesthesia and extended periods of bed rest or other inactivity are often susceptible to a condition known as deep venous thrombosis, or DVT, which is a clotting of venous blood in the lower extremities and/or pelvis. This clotting occurs due to the absence of muscular activity in the lower extremities required to pump the venous blood (stasis), local vascular injury or a hypercoagulable state. The condition can be life-threatening if a blood clot migrates to the lung, resulting in a "pulmonary embolus" or otherwise interferes with cardiovascular circulation. One method of treatment involves administration of an anti-coagulant.

The rapid absorption of biological agents, such as UFH or LMWH, after inhalation as dry particles can be very valuable in the treatment of myocardial infarction, acute coronary syndrome, and/or venous thromboembolism. Intravenous administration of UFH has been used widely for treatment of venous thromboembolism in combination with oral warfarin. Due to the improved efficacy and reduced risks, however, LMWHs have been increasingly used as an alternative to intravenous UFH in treatment of venous thromboembolism. The efficacy of heparin therapy may depend on achieving critical therapeutic levels (e.g., such as those that may be measured by anti-Xa activity and/or anti-IIa activity) within the first 24 hours of treatment. Intrapulmonary delivery of heparin particles to achieve rapid therapeutic levels of heparin in the early stage of thromboembolism, could also be combined with either s.c. administration of LMWHs or formulated heparin particles for prolonged antithrombotic/anticoagulant effect.

The methods of the invention are useful also for treating cerebral ischemia. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue. Cerebral ischemia may result in either transient or permanent deficits and the seriousness of the neurological damage in a patient who has experienced cerebral ischemia depends on the intensity and duration of the ischemic event. A transient ischemic attack (TIA) is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thrombus or thromboembolism. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms. The methods of this invention also encompass treatment and prevention of thromboembolic complications that may develop post prosthesis surgery.

The compositions of the invention are also useful for treating or preventing wherein the subject has or is at risk of a disorder selected from the group consisting of disease associated with coagulation, such as thrombosis, cardiovascular disease, vascular conditions or atrial fibrillation; migraine, atherosclerosis; an inflammatory disorder, such as autoimmune disease or atopic disorders; an allergy; a respiratory disorder, such as asthma, emphysema, adult respiratory distress syndrome (ARDS), cystic fibrosis, or lung reperfusion injury; a cancer or metastatic disorder, an angiogenic disorder, such as neovascular disorders of the eye, osteoporosis, psoriasis, and arthritis, Alzheimers'; bone fractures such as hip fractures; or is undergoing or having undergone surgical procedure, organ transplant, orthopedic surgery, hip replacement, knee replacement, percutaneous coronary intervention (PCI), stent placement, angioplasty, coronary artery bypass graft surgery (CABG).

The compositions of the invention are also useful in the treatment of inflammatory or allergic disorders, including respiratory diseases such as cystic fibrosis, asthma, allergy, emphysema, and adult respiratory distress syndrome (ARDS); lung reperfusion injury; ischemia-reperfusion injury of the lung, kidney, heart, and gut; and lung tumor growth and metastasis.

Cystic fibrosis is a chronic progressive disease affecting the respiratory system. One serious consequence of cystic fibrosis is *Pseudomonas aeruginosa* lung infection, which by itself accounts for almost 90% of the morbidity and mortality in cystic fibrosis. Therapeutics for treating cystic fibrosis include antimicrobials for treating the pathogenic infection.

Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Bioactive agents such as heparin are capable of inhibiting this elastase induced injury. Adult respiratory distress syndrome is a term which encompasses many acute defuse infiltrative lung lesions of diverse ideologies which are accompanied by severe atrial hypoxemia. One of the most frequent causes of ARDS is sepsis. Other types of inflammatory diseases which are treatable are refractory ulcerative colitis, Crohn's disease, non-specific ulcerative colitis, multiple sclerosis, and interstitial cystitis.

The methods of the invention in some embodiments are directed to the treatment of acute thromboembolic stroke using sulfated polysaccharides. An acute stroke is a medical syndrome involving neurological injury resulting from an ischemic event, which is an interruption in the blood supply to the brain.

An effective amount of a sulfated polysaccharide preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The pharmaceutical sulfated polysaccharide preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, hirudin, bivalarutin, and other direct thrombin inhibitors, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, at al, *J Am Coll Cardiol*; v. 25 (7 suppl), p. 10S-17S(1995)). Thrombolytic agents include, but are not limited to, plasminogen, $a_2$-antiplasmin, streptokinase, antistreplase, TNK, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et al., *Anal. Biochem.* 168, 428-435 (1988) and its modified form described by Bennett, W. F. et al., 1991, supra, the entire contents of which are hereby incorporated by reference.

In one embodiment, the sulfated polysaccharide preparations are used for inhibiting angiogenesis. An effective amount for inhibiting angiogenesis of the sulfated polysaccharide preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to elongation cell growth factors. The inhibition of angiogenesis can cause tumor regression in animal models, suggesting a use as a therapeutic anticancer agent. An effective amount for inhibiting angiogenesis is an amount of sulfated polysaccharide preparation which is sufficient to diminish the number of blood vessels growing into a tumor. This amount can be assessed in an animal model of tumors and angiogenesis, many of which are known in the art.

The sulfated polysaccharide preparations are also useful for inhibiting neovascularization associated with eye disease. In another embodiment, the sulfated polysaccharide preparation is administered to treat psoriasis. Psoriasis is a common dermatologic disease causes by chronic inflammation.

Sulfated polysaccharide containing compositions, may also inhibit cancer cell growth and metastasis. Thus the methods of the invention are useful for treating and/or preventing tumor cell proliferation, angiogenesis or metastasis in a subject. The terms "prevent" and "preventing" as used herein refer to inhibiting completely or partially the biological effect, e.g., angiogenesis or proliferation or metastasis of a cancer or tumor cell, as well as inhibiting any increase in the biological effect, e.g., angiogenesis or proliferation or metastasis of a cancer or tumor cell.

Cancers or tumors include but are not limited to biliary tract cancer, brain cancer, breast cancer, cervical cancer; choriocarcinoma; colon cancer, endometrial cancer; esophageal cancer; gastric cancer; intraepithelial neoplasms; leukemias, lymphomas; liver cancer; lung cancer (e.g. small cell and non-small cell); melanoma; neuroblastomas; oral cancer; ovarian cancer; pancreatic cancer, prostate cancer; rectal cancer; sarcomas; skin cancer, testicular cancer; thyroid cancer, and renal cancer, as well as other carcinomas and sarcomas.

A subject in need of cancer treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

When administered to a patient undergoing cancer treatment, the polysaccharide particles may be administered in cocktails containing other anti-cancer agents. The polysaccharide compositions may also be administered in cocktails containing agents that treat the side-effects of radiation therapy, such as anti-emetics, radiation protectants, etc.

Subjects in need of treatment may also be subjects with abnormal renal function, including renal failure, as measured by RFI, urea, creatinine, phosphorus, glomerular filtration rate (GFR), or blood urea nitrogen (BUN) levels in blood and/or urine. The specific measures are as follows:

Renal Failure Index (RFI)—in mEq/L is calculated as follows:

(urine sodium in mEq/L)/((urine creatinine in mg/dL)/ (plasma creatinine in mg/dL)).

An RFI of ≤1 indicates prerenal azotemia; an RFI=1-3 is less definitive but usually indicates tubular necrosis; and an RFI≥3 indicates acute tubular necrosis Urine Specific Gravity—This is a measure of how concentrated a urine sample is. Water has a specific gravity of 1.000. A dilute urine sample has a specific gravity less that 1.020 (often less than 1.010). A concentrated urine sample would have a specific gravity over 1.030 or 1.040.

Blood Urea Nitrogen (BUN)—This is a protein metabolite excreted by the kidney (it is one of the toxins we are concerned about). In a normal patient the BUN is 25 or so. A good goal for BUN in kidney failure is 60-80. Often at the time of diagnosis, BUN is well over 150, 200, or even 300.

Creatinine—This is another protein metabolite (though this one is less dependent on dietary protein intake than is BUN). A normal creatinine is less than 2.0. A good goal in kidney failure is a creatinine of 4.5 or less. BUN and creatinine may be tracked (together with several other parameters) over time and in response to different treatments.

Phosphorus—The calcium/phosphorus balance becomes deranged in kidney failure due to hormone changes that ensue as well as the inability of the failing kidney to excrete phosphorus. If calcium and phosphorus levels become too high, the soft tissues of the body will develop mineralized deposits which are inflammatory and uncomfortable. The bones will weaken as well.

Potassium—The failing kidney is unable to conserve potassium efficiently and supplementation may be needed.

Packed Cell Volume/Hematocrit—This is a measure of red blood cell amount. More literally it represents the percentage of the blood made up by red blood cells. The hormone that stimulates the production of red blood cells is made by the kidney. The failing kidney does not make this hormone in normal amounts and anemia can result. Anemia is often worsened by the extra fluid administrations needed to manage the kidney toxins.

Glomerular Filtration Rate (GFR)—This test is a measure of how well the kidneys are removing wastes and excess fluid from the blood. It may be calculated from the serum creatinine level using age, weight, gender and body size. Normal GFR can vary according to age, decreasing in aging subjects. The normal value for GFR is 90 or above. A GFR below 60 is a sign that the kidneys are not working properly. A GFR below 15 indicates probable kidney failure.

Disorders associated with abnormal renal function/failure include, but are not limited to, end stage nephritises, renal calculus, ischemia renal disease, hypertension nephropathy, diabetes nephropathy, glomerulonephritises, tubulointerstial nephritises, and renal hypertension.

Effective amounts of the composition containing sulfated polysaccharides of the invention are administered to subjects in need of such treatment. Effective amounts are those amounts which will result in a desired reduction in cellular proliferation or metastasis or prevent coagulation or other therapeutic benefit without causing other medically unacceptable side effects. Such amounts can be determined with no more than routine experimentation. It is believed that doses ranging from 1 nanogram/kilogram to 100 milligrams/kilogram, depending upon the mode of administration, will be effective. The effective percentage of intact sulfated polysaccharide may be determined with no more than routine experimentation. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including inhalation, oral, subcutaneous, intravenous, intraperitoneal, transdermal, buccal, sublingual, parenteral, intramuscular, intranasal, intratracheal, ocular, vaginal, rectal, transdermal, and/or sublingual.

In some aspects of the invention, the effective amount of a composition containing sulfated polysaccharide is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus, the LMWH compositions can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparan sulfate proteoglycans such as perlecan, which bind to and localize bFGF, vitronectin as well as transforming growth factor (TGF), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated herein by reference. An in vivo barrier refers to a cellular barrier present in the body of a subject.

The sulfated polysaccharides of the invention may optionally be formulated in a pharmaceutically acceptable carrier. The compositions may further be formulated into specific delivery devices. Thus, in some embodiments of the invention the compositions are specifically formulated for intravenous, subcutaneous, oral, aerosol, or other mucosal form of delivery. In some embodiments the compositions are formulated in sustained release devices as described below.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2 mole % W/V); citric acid and a salt (1-3 mole % W/V); boric acid and a salt (0.5-2.5 mole % W/V); and phosphoric acid and a salt (0.8-2 mole % W/V). Suitable preservatives include benzalkonium chloride (0.003-0.03 mole % W/V); chlorobutanol (0.3-0.9 mole % W/V); parabens (0.01-0.25 mole % W/V) and thimerosal (0.004-0.02 mole % W/V).

The invention provides pharmaceutical compositions, for medical use, which comprise sulfated polysaccharide preparations together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the invention, the term "carrier" denotes an organic or inorganic ingredient, natural or synthetic, with which the active ingredient is combined to facilitate the application. The components of the pharmaceutical compositions also are capable of being commingled with the sulfated polysaccharide of the invention, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

A variety of administration routes are available. The particular mode selected will depend, of course, upon the particular percentage of sulfated polysaccharide selected, the particular condition being treated, and the dosage required for therapeutic efficacy. The methods of this invention, generally speaking, may be practiced using any mode of administration that is medically acceptable, meaning any mode that produces effective levels of a biological effect without causing clinically unacceptable adverse effects.

For use in therapy, an effective amount of the sulfated polysaccharide preparation can be administered to a subject by any mode that delivers the sulfated polysaccharide to the desired surface, e.g., mucosal, systemic. "Administering" the pharmaceutical composition of the invention may be accomplished by any means known to the skilled artisan. Preferred routes of administration include, but are not limited to, inhalation, oral, subcutaneous, intravenous, intraperitoneal, transdermal, buccal, buccal, sublingual, parenteral, intramuscular, intranasal, intratracheal, ocular, vaginal, rectal, transdermal, and/or sublingual.

For oral administration, the compounds (i.e., sulfated polysaccharide preparations) can be formulated readily by combining the active compound(s) with pharmaceutically acceptable carriers well-known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. In addition, dry powder formations for inhalation therapy are within the scope of the invention. Such dry powder formulations may be prepared as disclosed in WO 02/32406, the entire teachings of which are incorporated herein by reference.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro) capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, (1990), which is incorporated herein by reference.

The compositions may conveniently be presented in unit dosage form and may be prepared by any of the methods well known in the art of pharmacy. All methods include the step of bringing the active sulfated polysaccharide into association with a carrier which constitutes one or more accessory ingredients. In general, the compositions are prepared by uniformly and intimately bringing the polysaccharide into association with a liquid carrier, a finely divided solid carrier, or both, and then, if necessary, shaping the product. The polysaccharide may be stored lyophilized.

Other delivery systems can include time-release, delayed release or sustained release delivery systems. Such systems can avoid repeated administrations of the sulfated polysaccharide of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. No. 4,748,034 and U.S. Pat. No. 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

When administered to a patient undergoing cancer treatment, the sulfated polysaccharide compositions may be administered in cocktails containing other anti-cancer agents. The compositions may also be administered in cocktails containing agents that treat the side-effects of therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Glevec; Herceptin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituxin; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur, Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The sulfated polysaccharide compositions may also be linked to a targeting molecule. A targeting molecule is any molecule or compound which is specific for a particular cell or tissue and which can be used to direct the sulfated polysaccharide to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor antigens include but are not limited to Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HBR2/neu, p21ras, RCAS1, fetoprotein, E-cadherin, catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Examples of tumor antigens which bind to either or both MHC class I and MHC class II molecules, see the following references-Coulie, *Stem Cells* 13:393-403, 1995; Traversari et al., J. Exp. Med. 176:1453-1457, 1992; Chaux et al., J. Immunol. 163:2928-2936, 1999; Fujie et al., Int. J. Cancer 80.169-172, 1999; Tanzarella at al., Cancer Res. 59:2668-2674, 1999; van der Bruggen et al., Eur. J. Immunol. 24:2134-2140, 1994; Chaux et al., J. Exp. Med. 189:767-778, 1999; Kawashima at al, Hum. Immunol. 59:1-14, 1998; Tahara et al., Clin. Cancer Res. 5:2236-2241, 1999; Gaugler at al., J. Exp. Med. 179:921-930, 1994; van der Bruggen at al., Eur. J. Immunol. 24:3038-3043, 1994; Tanaka at al., Cancer Res. 57:4465-4468, 1997; Oiso at al., Int. J. Cancer 81:387-394, 1999; Herman at al., Immunogenetics 43:377-383, 1996; Manici at al., J. Exp. Med. 189:871-876, 1999; Duffour at al., Eur. J. Immunol. 29:3329-3337, 1999; Zorn at al., Eur. J. Immunol. 29:602-607, 1999; Huang at al., J. Immunol. 162: 6849-6854, 1999; Boël at al., Immunity 2:167-175, 1995; Van den Eynde at al., J. Exp. Med. 182:689-698, 1995; De Backer at al., Cancer Res. 59:3157-3165, 1999; Jäger at al., J. Exp. Med. 187:265-270, 1998; Wang at al., J. Immunol. 161:3596-3606, 1998; Aarnoudse at al., Int. J. Cancer 82:442-448, 1999; Guilloux et al., J. Exp. Med. 183:1173-1183, 1996; Lupetti et al., J. Exp. Med. 188:1005-1016, 1998; Wölfel et al., Eur. J. Immunol. 24:759-764, 1994; Skipper et al., J. Exp. Med. 183:527-534, 1996; Kang et al., J. Immunol. 155:1343-1348, 1995; Morel at al., Int. J. Cancer 83:755-759, 1999; Brichard et al., Eur. J. Immunol. 26:224-230, 1996; Kittlesen at al., J. Immunol. 160:2099-2106, 1998; Kawakami at al., J. Immunol. 161:6985-6992, 1998; Topalian et al., J. Exp. Med. 183:1965-1971, 1996; Kobayashi at al., Cancer Research 58:296-301, 1998; Kawakami et al., J. Immunol. 154:3961-3968, 1995; Tsai et al., J. Immunol. 158:1796-1802, 1997; Cox et al., Science 264:716-719, 1994; Kawakami et al., Proc. Natl. Acad. Sci. USA 91:6458-6462, 1994; Skipper at al., J. Immunol. 157:5027-5033, 1996; Robbins et al., J. Immunol. 159:303-308, 1997; Castelli et al, J. Immunol. 162:1739-1748, 1999; Kawakami et al., J. Exp. Med. 180: 347-352, 1994; Castelli et al., J. Exp. Med. 181:363-368, 1995; Schneider et al., Int. J. Cancer 75:451-458, 1998; Wang et al., J. Exp. Med. 183:1131-1140, 1996; Wang et al., J. Exp. Med. 184:2207-2216, 1996; Parkhurst to al., Cancer Research 58:4895-4901, 1998; Tsang et al., J. Natl Cancer Inst 87:982-990, 1995; Correale et al., J Natl Cancer Inst 89:293-300,1997; Coulie et al., Proc. Natl. Acad. Sci. USA 92:7976-7980, 1995; Wölfel et al., Science 269:1281-1284, 1995; Robbins et al., J. Exp. Med. 183:1185-1192, 1996; Brändle et al. J. Exp. Med. 183:2501-2508, 1996; ten Bosch et al., Blood 88:3522-3527, 1996; Mandruzzato et al., J. Exp. Med. 186:785-793, 1997; Guéguen et al., J. Immunol. 160: 6188-6194, 1998; Gjertsen et al., Int. J. Cancer 72:784-790, 1997; Gaudin at al., J. Immunol. 162:1730-1738, 1999; Chiari et al., Cancer Res. 59:5785-5792, 1999; Hogan at al., Cancer Res. 58:5144-5150, 1998; Pieper et al., J. Exp. Med. 189:757-765, 1999; Wang et al., Science 284:1351-1354, 1999; Fisk at al., J. Exp. Med. 181:2109-2117, 1995; Brossart et al., Cancer Res. 58:732-736, 1998; Röpke et al., Proc. Natl. Acad. Sci. USA 93:14704-14707, 1996; Ikeda et al., Immunity 6:199-208, 1997; Ronsin at al., J. Immunol. 163:483-490, 1999; Vonderheide et al., Immunity 10:673-679, 1999. These antigens as well as others are disclosed in PCT Application PCT/US98/18601.

The following description of experiments performed is exemplary and non-limiting to the scope of the claimed invention.

EXAMPLES

Example 1

Development of a Compositional Analysis Method for the Structural Characterization of Heparins Several techniques have been utilized for the structural analysis of heparin preparations. Gradient polyacrylamide gel electrophoresis (PAGE) and strong ion exchange HPLC (SAX) have previously been used for the qualitative and quantitative analysis of heparin preparations (Liu et al., *Glycobiology* 5:765-774, 1995; Turnbull et al., *Proc. Natl. Acad. Sci. USA* 96: 2698-2703, 1999; Merry et al., *J. Biol. Chem.* 274: 18455-18462, 1999). The gradient PAGE method, while useful in determining molecular weight, cannot offer information about the fine structure of heparin preparations. SAX-HPLC, relying on detection by ultraviolet absorbance or radioactivity, is often insufficiently sensitive for the detection of small amounts of structurally important heparin-derived oligosaccharides.

Capillary electrophoresis (CE) is a very sensitive methodology with high resolving power that has been used to characterize heparin sulfate-like glycosaminoglycan (HLGAG) oligosaccharides. In addition, CE has been used in conjunction with enzymatic digestion, to characterize the disaccharide composition of HLGAG complex oligosaccharides. See, e.g., U.S. patent application Ser. Nos. 09/557,997 and 09/558,137 filed on Apr. 24, 2000, which are incorporated herein by reference in their entirety. In combination with either off-line or on-line mass spectral analysis, CE is a powerful tool for the structural characterization and quantification of HLGAG di- and oligosaccharides.

The methods of the invention make it possible to complete the structural characterization of UFH and LMWHs using a similar approach. Determining the exact composition of UFHs from different sources as well as LMWHs is the first important step in correlating function with a structure. This is of special importance since current manufacturing practices for UFH and LMWHs use functional assays (e.g., anti-Xa assay) and gross physical characterization to provide quality control. Development of appropriate tools for the structural characterization of heparins would provide a more rigorous tool for the analysis of heparin.

This technique, viz., a Compositional Analysis Method (CAM), can be used to quantify the di- and tetrasaccharide and higher building blocks of heparins. Furthermore, this technique can be used to provide a key correlate between the structure and the function of various heparin and LMWH preparations, thus providing the guidance necessary to create compositions with a desired activity profile.

Materials and Methods

UFH was purchased from Celsus Laboratories (Cincinnati, Ohio) and molar concentrations of stocks were calculated based on an average molecular weight of 12,000 Da. Disaccharide standards were purchased from Sigma chemicals (St. Louis, Mo.). Heparinase I, II, and III were produced as described previously (Ernst, et al. *Biochem. J.* 315:589-597 (1996); Pojasek, et al. *Biochemistry* 39: 4012-4019 (2000)).

UFH was subjected to exhaustive depolymerization with an enzyme cocktail made up of heparinase I, II, and heparinase III. 9 μl of 10 μg/μl concentration of UFH in $H_2O$ was digested with 1 μl of an enzyme cocktail consisting of 100 nM each of heparinase I, II, and III in 25 mM sodium acetate, 100 mM sodium chloride, 5 mM calcium acetate buffer, pH 7.0 for 12 hours at 37° C. The CE sample was prepared by diluting 1 μl of the digest with 9 μl of $H_2O$. Mass spectra were collected using parameters as outlined previously and calibrated externally by using signals for protonated $(RG)_{19}R$ and its complex with a nitrous acid-derived hexasaccharide of the sequence $I_{2S}H_{NS,6S} I_{2S}H_{NS,6S} I_{2S}Man_{6S}$.

Results

Development of CAM Using UFH.

As a first step towards the development of CAM, we analyzed UFH from a commercial source. UFH was subjected to exhaustive depolymerization with an enzyme cocktail made up of heparinases I, II, and III from *Flavobacterium heparinum*. Digestion of UFH with a heparinase cocktail results in cleavage of glycosidic linkages via the elimination of water resulting in the degradation of the polymer chain. The resulting products, with a $\Delta^{4,5}$ unsaturated uronic acid at the non-reducing end, readily absorb UV light and can be facially monitored at their $\lambda_{max}$ of 232 nm.

Figure 1B:
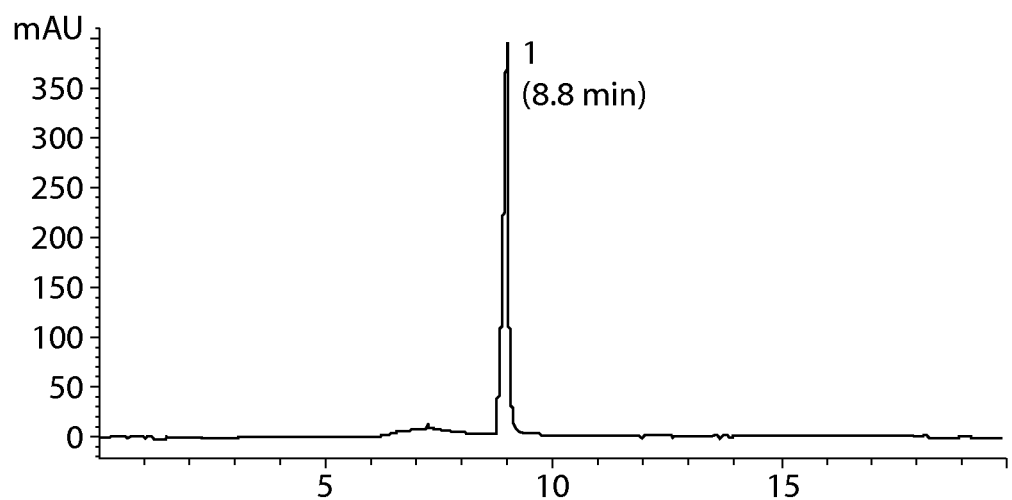
FIG. 1B. CE spectrum of peak 1 which has been isolated from enoxaparin and re-injected into the CE to ascertain its purity.

To measure the accuracy and precision of the CAM technique, UFH was digested in duplicate and each sample was analyzed independently by CE. In addition, the experiment was repeated twice for each sample, resulting in four readings for UFH. Importantly, this entire analysis used only nanograms of starting material, ensuring the consumption of a minimum of material. Separation of the species resulting from enzymatic digestion of UFH by CE resulted in the appearance of eight distinct species that could be readily quantified (FIG. 1). Capillary electrophoresis trace of UFH derived from porcine intestinal mucosa. 9 µl of 10 ng/nL concentration of UFH was digested with 1 µL of enzyme cocktail consisting of 100 nM each of Heparinase I, II, and III for 12 hours at 37° C. The CE sample was prepared by diluting the digest with H$_2$O to give a final heparin concentration of 1.0 ng/nL. 57 nL of this CE sample was injected into the CE. Each of the eight peaks p1-p8 was collected, the purity of the collected peaks was checked by re-injecting into CE, and their mass was measured by offline MALDI Mass Spectrometry. The identity of p1-p7 was further confirmed by matching their migration time with that of standard, commercially available disaccharides. p1 was thus confirmed as the trisulfated disaccharide $\Delta U_{2S}H_{NS,6S}$. p2, p3, and p4 are disulfated disaccharides, and p5, p6, and p7 are monosulfated disaccharides. p8 was determined as a tetra or penta sulfated, non/mono acetylated tetrasaccharide comprising of one or more of the following: $\Delta UH_{NAc,6S}GH_{NS,3S,6S}$; $\Delta UH_{NS,6S}GH_{NS,3S,6S}$; $\Delta UH_{NAc,6S}GH_{NS,3S}$; or $\Delta UH_{NS,6S}GH_{NS,3S}$, referred to herein as "p8" or "peak 8." In a similar manner, peaks (in addition to the 8 peaks described here) present in other LMWH samples such as enoxaparin, and dalteparin have also been characterized. The species, labeled 1 through 8, were collected and characterized. First, the mass of each unknown was assessed by offline MALDI MS as described previously U.S. Pat. No. 5,607,859. Further, to confirm the identity of the unknown, the collected peak was desalted, rerun on CE and identified by comigration with known standards.

Consistent with previous structural studies on UFH and what is known of the substrate specificities of the heparinases, seven of the eight unknowns (p1-p7 of 8) were identified as disaccharides. Species p1 was identified as $\Delta U_{2S}H_{NS,6S}$, the primary disaccharide building block of heparin. Unknowns p2-p4 were identified as disulfated disaccharide isomers: $\Delta U_{2S}H_{NS}$, $\Delta UH_{NS,6S}$, $\Delta U_{2S}H_{NAc,6S}$, accordingly. Finally, p5-p7 were identified as the monosulfated disaccharides $\Delta UH_{NS}$, $\Delta U_{2S}H_{NAc}$, $\Delta UH_{NAc,6S}$. Importantly, very little, if any, unsulfated disaccharide ($\Delta UH_{NAc}$) could be detected in UFH.

In addition to the characterization of the seven disaccharides, we also completed structural characterization of unknown p8. Isolation and sequencing of this oligosaccharide using the PEN-MALDI sequencing approach (Venkataraman, et al., Science 286:537-42 (1999)) indicated that p8 is a tetra or penta sulfated, non/mono acetylated tetrasaccharide comprising of one or more of the following: $\Delta U H_{NAc,6S}GH_{NS,3S,6S}$; $\Delta U H_{NS,6S}GH_{NS,3S,6S}$; $\Delta U H_{NAc,6S}GH_{NS,3S}$; or $\Delta U H_{NS,6S}GH_{NS,3S}$. To quantify the mole % in heparin of p1-p8 requires the determination of the response factor (RF) for each species. To obtain the RF for each species, known concentrations of standards for p1-p8 were injected on the CE and used to determine a RF for each (Table 1). We then used these RFs to determine the mole % of each saccharide unit in heparin (Table 1). Analysis of the mole % composition of heparin indicates that most of the polymer chain (>50 mole %) consists of the trisulfated disaccharide: $\Delta U_{2S}H_{NS,6S}$. Another ≥20 mole % of the UFH chain consists of the different isomers of the disulfated disaccharides, with minor contributions from the monosulfated disaccharides and the tetrasaccharide of peak 8.

TABLE 1

Compositional Analysis Table for UFH

| Compound | AUC | % Relative AUC | Response Factor (RF) | Corrected concentration | Mole % |
|---|---|---|---|---|---|
| p1 | 14639 | 62.1 | 1 | 62.1 | 66.1 |
| p2 | 2050.9 | 8.7 | 0.893 | 7.8 | 8.3 |
| p3 | 3088.1 | 13.1 | 0.829 | 10.9 | 11.6 |
| p4 | 707.2 | 3 | 0.823 | 2.5 | 2.6 |
| p5 | 1249.4 | 5.3 | 0.601 | 3.2 | 3.4 |
| p6 | 895.8 | 3.8 | 0.405 | 1.5 | 1.6 |
| p7 | 235.7 | 1.0 | 0.572 | 0.6 | 0.6 |
| p8 | 707.2 | 3 | 1.768 | 5.3 | 5.6 |

The area under the curve (AUC) was measured for each peak from the CE spectrum of UFH digested with the enzyme cocktail as shown in FIG. 1. The response factor calculated for each saccharide was used to calculate their corrected relative concentration in the enzyme digest. The last column gives the mole percentage of each of the building block of UFH. The unsulfated saccharides, which constitute <1 mole % of UFH, is not taken into consideration in constructing this compositional analysis table. As demonstrated here, construction of this compositional analysis table as shown by this method is independent of the concentration or the weight of the heparin digest analyzed by the CE.

Column 1 gives the AUC measured for p1-p8. Column 2 gives the % relative AUC. Multiplying the % relative AUC with the RF gives the corrected relative concentration or the % relative AUC of p1-p8 in terms of peak 1. These are then normalized to get the molar % of disaccharides p1-p7 and tetrasaccharide p8.

Experiments were completed to verify the instrumental reproducibility and to ascertain if the compositional analysis digest is indeed complete. There was little variability (less than 4%) in migration times and mole % determinations among samples, regardless of the sample amount injected into the capillary (varying over three orders of magnitude) or the amount of enzyme cocktail that was added to the sample (from 100 nM enzyme to 1 µM) (Table 2). Taken together, these results indicate that CAM is a rigorous, sensitive, and accurate methodology to determine the composition of UFH.

TABLE 2

Compositional analysis of UFH performed by CE can be used to rigorously compare different batches of LMWH. UFH was digested with either 1 µl or 5 µl of enzyme cocktail (EC). Each sample was digested in duplicate and each digest was analyzed in duplicate by CE. In all the samples, disaccharides p1-p7 had the same migration time. Comparison of duplicate analysis of the same sample (UFH 1/1 with UFH 1/2, UFH 2/1 with UFH 2/2, and UFH 3/1 with UFH 3/2) shows that there is good instrumental reproducibility. Comparison of either UFH 1/1 or UFH 1/2 with UFH 2/1 or UFH 2/2 shows that there is minimal run-to-run variation. Comparison of UFH digested with 1 µl of EC with UFH digested with 5 µl of EC illustrates that increasing the enzyme quantity does not change the disaccharide profile appreciably showing that exhaustive digestion is reached by using 1 µl of EC as shown in FIG. 1.

| Sample | p1 | p2 | p3 | p4 | p5 | p6 | p7 | p8 |
|---|---|---|---|---|---|---|---|---|
| UFH 1/1 1 µl EC | 66.1 | 8.3 | 11.7 | 2.6 | 3.4 | 1.6 | 0.6 | 5.6 |

TABLE 2-continued

Compositional analysis of UFH performed by CE can be used to rigorously compare different batches of LMWH. UFH was digested with either 1 μl or 5 μl of enzyme cocktail (EC). Each sample was digested in duplicate and each digest was analyzed in duplicate by CE. In all the samples, disaccharides p1-p7 had the same migration time. Comparison of duplicate analysis of the same sample (UFH 1/1 with UFH 1/2, UFH 2/1 with UFH 2/2, and UFH 3/1 with UFH 3/2) shows that there is good instrumental reproducibility. Comparison of either UFH 1/1 or UFH 1/2 with UFH 2/1 or UFH 2/2 shows that there is minimal run-to-run variation. Comparison of UFH digested with 1 μl of EC with UFH digested with 5 μl of EC illustrates that increasing the enzyme quantity does not change the disaccharide profile appreciably showing that exhaustive digestion is reached by using 1 μl of EC as shown in FIG. 1.

| Sample | p1 | p2 | p3 | p4 | p5 | p6 | p7 | p8 |
|---|---|---|---|---|---|---|---|---|
| UFH 1/2 1 μl EC | 66.1 | 8.4 | 11.5 | 2.7 | 3.3 | 1.5 | 0.5 | 5.8 |
| UFH 2/1 1 μl EC | 66.0 | 8.5 | 11.8 | 2.8 | 3.4 | 1.8 | 0.4 | 5.5 |
| UFH 2/2 1 μl EC | 66.4 | 8.3 | 11.5 | 2.6 | 3.5 | 1.9 | 0.3 | 5.4 |
| UFH 3/1 5 μl EC | 65.7 | 8.3 | 11.4 | 2.7 | 3.6 | 2.0 | 0.4 | 5.9 |
| UFH 3/2 5 μl EC | 65.9 | 8.6 | 11.5 | 2.5 | 3.5 | 2.0 | 0.4 | 5.6 |

Extension of CAM to LMWH Preparations.

Given the ability of CAM to separate the enzymatically-derived components of UFH and to provide an accurate assessment of the overall composition of UFH, we sought to apply it to the structural analysis of LMWHs. Three different LMWHs were used, viz., tinzaparin, ardeparin, and enoxaparin, all of which are currently in clinical use (Table 3). Compositional comparison of the three LMWHs and UFH indicates that there are distinct differences in their structures, most notably in the mole % of the trisulfated disaccharide, p1, and the disulfated disaccharides p2 and p3, and the tetrasaccharide p8.

TABLE 3

Comparison of the disaccharide composition and anti-Xa activity of UFH and commercial LMWHs.

| Saccharide | enoxaparin % of total | dalteparin % of total | UFH % of total |
|---|---|---|---|
| p1 | 63.6 | 62.1 | 66.1 |
| p2 | 8.3 | 4.3 | 8.3 |
| p3 | 11.3 | 9.8 | 11.6 |
| p4 | 2.0 | 2.6 | 2.6 |
| p5 | 3.5 | 1.4 | 3.4 |
| p6 | 1.8 | 1.2 | 1.6 |
| p7 | 1.9 | 5.4 | 0.6 |
| p8 | 6.4 | 9.5 | 5.6 |
| p9 | 0.5 | 0 | 0 |
| p10 | 0.7 | 0 | 0 |
| p11 | 0 | 3.7 | 0 |
| Anti-Xa (IU/mg) | 100 | 150 | 130 |
| Anti-IIa (IU/mg) | 25 | 60 | 130 |
| MW (Da) | 4,200 | 6,000 | 12,000 |

Peak 8 as an Indicator of Anticoagulant Function.

Figure 2A:
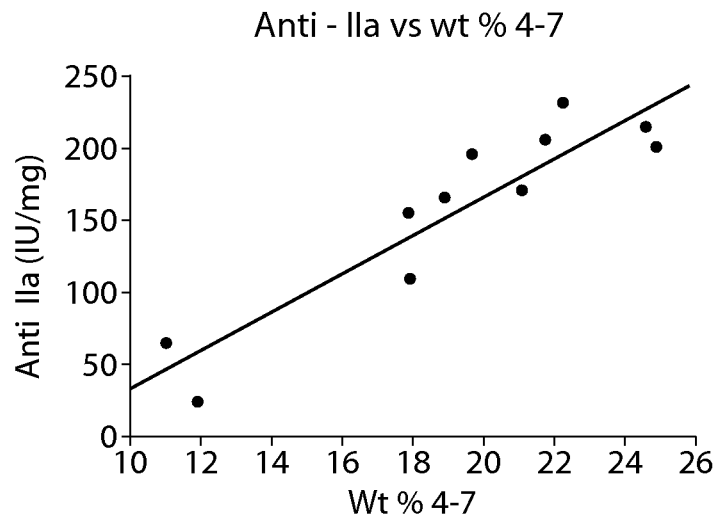
FIGS. 2A and 2B: Line plots of anti-IIa (2A) and anti-Xa (2B) values of UFH, UFH size fractionated through Bio-gel P10 column, a LMWH generated as described herein, and commercial LMWHs. There is a linear correlation between the anti-Xa/IIa values, and the mole % peak 8 content of the molecules.
Figure 2B:
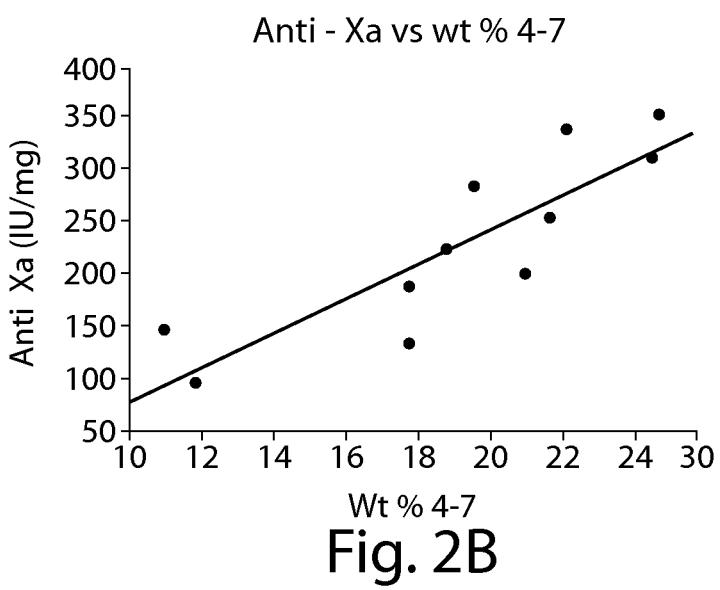

To test whether quantification of 8 could be used to predict anti-coagulant function, we plotted the anti-Xa or anti-IIa activity of UFH and LMWH's versus p8 content. Plot of Anti-IIa and Anti-Xa values of UFH, UFH size fractionated through Bio-gel P10 column, a LMWH generated in our laboratory, and commercial LMWHs demonstrates there is a linear correlation between the anti-Xa/IIa values, and the mole % of p8 of the preparation. Thus the anticoagulant and antithrombotic efficiency of heparin and LMWH can be estimated from their chemical composition. In the case of the anti-Xa activity, p8 content showed a very good correlation with activity ($r^2=0.8$) (FIG. 2). An even better correlation ($r^2=0.9$) was observed when anti-IIa activity was plotted versus p8 content. Importantly, this correlation holds regardless of the source of the UFH or LMWH and the means by which the LMWH is generated. Thus, these results demonstrate that a particular structural motif, identified by CAM, e.g., peak 8, can be used to predict both anti-Xa and anti-IIa activity.

Creation of a Second Generation LMWH:

Based on the above findings, we examined whether it would be possible to create a LMWH with increased anti-Xa and anti-IIa activities in vitro. We reasoned that these activities could be increased by optimizing the p8 content of a LMWH preparation. To test this possibility, we digested UFH with heparinase under controlled conditions and monitored the p8 content as a result of enzymatic digestion. When the digestion was judged complete, the LMWH was purified by size fractionation, its MW assessed, and the anti-Xa and anti-IIa activities were determined. The in vitro profile of these new LMWHs were compared to that of enoxaparin, tinzaparin, and ardeparin (Table 3).

Notably, under two separate digestion and separation conditions, slightly different LMWHs were created. The first is hereafter referred to as second generation M118 and the latter as second generation M215. Molecular weight measurement of the two indicated that M118 possessed a molecular weight of 5,000 Da, while that of M215 was 4,500 Da (Table 4). Importantly, both were found to have a polydispersity of 1.0, that is, both of these LMWHs were less heterogenous than other LMWHs as well as UFH. In addition, as shown in Table 5, CAM analysis of the two indicated that they possess a higher weight percent of peak 8 than other LMWHs, thus we would predict that both of these compounds should have higher anti-Xa and anti-IIa activity than other LMWHs.

TABLE 4

Comparison of the biological activities of Mimeon's LMWH with other LMWH.

| | Xa, IU/mg | IIa, IU/mg | Xa/IIa | $IC_{50}$, IIa | MW Da |
|---|---|---|---|---|---|
| M115 | 250 | 200 | 1.25 | 25.6 | 5000 |
| M411 | 200 | 130 | 1.5 | 38.0 | 4500 |
| enoxaparin | 100 | 25 | 4.0 | 236 | 4200 |
| ardeparin | 93 | 60 | 1.5 | 98.3 | 5000 |

MLMWHs have very high (>100 IU/mg) anti-IIa, and anti-Xa activities.

TABLE 5

Comparison of the molecular profile of Existing LMWH, and Heparin.

In vitro assessment of the activities of M115 and M411 indicated that, as predicted, M115 and M411 had higher anti-Xa activity. M115 had a measured anti-Xa activity of 330 IU/mg, over twice as high as UFH, and at least three times more than existing LMWHs. M411 was also a potent inhibitor of Xa, with an activity almost 1.5 times as high as UFH and approximately twice as great as existing LMWHs. Importantly, both M115 and M411 possessed significant anti-IIa activity of 200 IU/mg and 130 IU/mg, respectively. This is in contrast to existing LMWHs that exhibit 4-10 times less anti-IIa activity. These results are confirmed and extended by measuring the $IC_{50}$ of these compounds for thrombin activation. Taken together, these results indicate that by designing a LMWH with higher p8 content, it is possible to create a LMWH with increased activity.

Example 2

M115 and M411 are Superior to Other Heparins in Both IIa and Xa Pharmacokinetics After s.c. Administration M115 and M411 have markedly increased in vitro anti-Xa and IIa activity, expressed as IU per mg, compared to UFH or other LMWHs. A series of pharmacokinetic experiments using male New Zealand rabbits confirmed this in vivo. In these experiments, either UFH or LMWHs (M115 and M411) were administered to rabbits by subcutaneous injection. Then pharmacokinetic parameters were determined by following either the anti-Xa or IIa activities.

Methods

Male Previously Presented Zealand rabbits weighing 2.5 to 3.0 kg were used for pharmacokinetics studies. After anesthesia with Ketamine (40 mg/kg) and Xyalazine (5 mg/kg), a 24-gauze TEFLON™ (polytetrafluoroethylene) catheter was inserted into to the center auricular artery. The catheter was connected to a heparin cap filled with isotonic saline. Heparin solutions were injected subcutaneously to the rabbits at 1 and 3 and 6 mg/kg. Four different heparins (UFH, Ardeparin, Enoxaparin, and F1) were included in this study. 0.2 ml of blood was withdrawn 0, 5, 10, 30 min, 1, 2, 3, 4, 6, 8, 10, 12, 14, 18, 24 hours after the injection. The first 0.2 ml blood withdrawn was discarded with each withdraw. Blood samples were collected in an aqueous solution of sodium citrate (3.8 mole %; 1/9, v/v), centrifuged at 2000×g for 20 min and the resulting plasma was shock frozen and stored in −80° C. freezer until assay.

All reagents (Coatest heparin kit, S2238 substrate, Thrombin) were purchased from Chromogenix (Diapharma Group, Inc., OH). Anti-Xa assay was used to monitor plasma LMWH level. Anti-Xa assay was performed by modification of the amidolytic method of Teien and Lie (Thrombosis res. 10: 399-410, 1977) with Coatest heparin test kit by using S-2222 as the chromogenic substrate (Diapharma Group, Inc. OH). The detailed procedure was described elsewhere (Liu, etc., PNAS, 94: 1739-1744, 1997). The concentration of LMWH in unknown samples was calculated by comparing to the calibration curve derived from $1^{st}$ international standard for LMWH which was linear in the range of 0-0.7 IU/ml ($r^2 > 0.99$). The results were expressed in anti-Xa IU/mg and then in μg/ml. Anti-IIa assay was done similarly by using S2238 as substrate. Both Xa and IIa assays were performed by an automated coagulation machine (COAG-A-MATE MTX II™, Organon Teknika Durham, N.C. 27712).

Results

Figure 3:
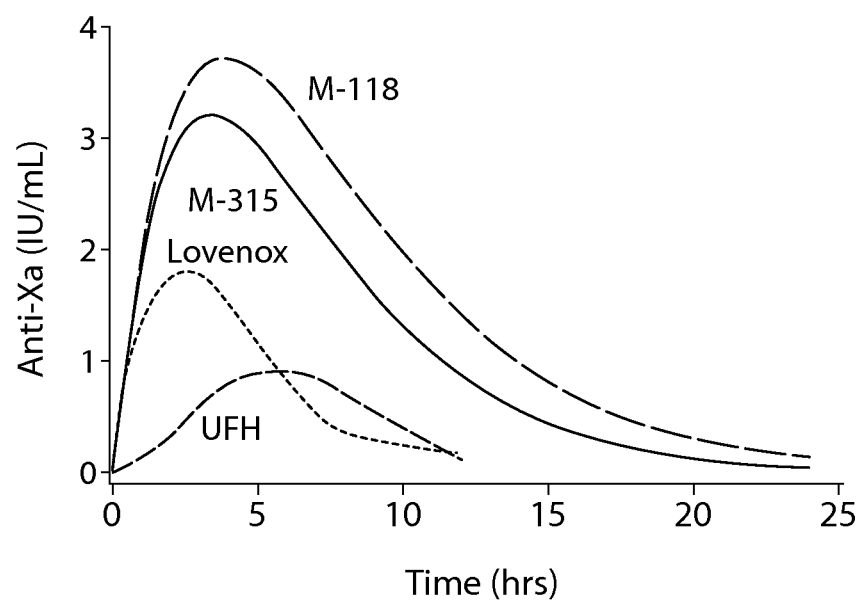
FIG. 3. Graph of plasma anti-Xa pharmacokinetics of M118, UFH, Enoxaparin and M312 given by s.c. administration in rabbits at 3 mg/kg.

At an equivalent dose of 3 mg/kg, the pharmacokinetic parameters derived from following the anti-Xa activity present in the plasma demonstrated that the bioavailability of M118 is about 3-4 fold higher than either UFH or other LMWHs (FIG. 3). M115 exhibits comparable absorption ($k_a$) and elimination ($k_e$) rate constants (Table 6) compared to UFH, demonstrating that the increased bioavailability is due to the higher inherent anti-Xa activity (IU/mg) of M115 as compared to other heparins (data not shown). This observation is consistent with the in vitro activities of M115. Thus, the absorption and elimination of M115 is as efficient as other heparins. As a result, a much higher plasma anti-Xa activity is achieved when the same dose is administered to the animals.

TABLE 6

The plasma anti-Xa pharmacokinetics parameters after s.c. administration.

|  | UFH | M115 | ENOXAPARIN | DALTEPARIN |
|---|---|---|---|---|
| Ka | 0.25 | 0.16 | 0.43 | 0.45 |
| Ke | 0.16 | 0.12 | 0.31 | 0.23 |
| $t_{1/2a}$(hr) | 2.85 | 5.27 | 1.67 | 1.73 |
| $t_{1/2e}$(hr) | 4.65 | 8.20 | 2.25 | 3.41 |
| AUC(IU*hr/ml) | 7.97 | 34.24 | 7.26 | 9.97 |
| $C_{max}$(IU/ml) | 0.51 | 3.53 | 1.20 | 2.00 |
| $t_{max}$(hr) | 5.16 | 11.87 | 2.76 | 3.20 |
| MRT(AUMC/AUC) | 6.22 | 9.96 | 5.01 | 5.73 |

To test whether the plasma anti-IIa activity can be correlated to the anti-Xa pharmacokinetics, plasma anti-IIa pharmacokinetics for UFH and the LMWHs was also established. Consistent with the observed difference in in vitro anti-IIa activity, the plasma anti-IIa pharmacokinetics result showed much higher bioavailability for M115 and M411 as compared to other heparins. This is especially true when one compares either enoxaparin or UFH with either M115 and M411. For enoxaparin, the significant observed difference can be attributed to the fact that enoxaparin possesses inherently low anti-IIa activity (~25 IU/mg compared to ~250 IU/mg for M115). In the case of UFH, its increased polydispersity results in the administration of some larger polysaccharide fragments that are eliminated faster, reducing bioavailability.

Example 3

M115 and M411 are a More Potent Inhibitor of Arterial Thrombosis

The formation of arterial thromboses is largely due to the activation and aggregation of platelets. Activated thrombin (IIa) is known to be a potent activator of platelet aggregation, hence, molecules containing high anti-IIa activity should be more potent inhibitors of arterial thrombosis formation. We investigated whether or not M115 and M411 produced a more pronounced antithrombotic effect using a rat arterial thrombosis model.

Methods

The arterial thrombosis model was performed essentially as described with minor modification. Male Sprague-Dawley rats weighing 350-400 g were anesthetized with Ketamine (80 mg/kg) and Xylazine (10 mg/kg). The right side carotid artery was carefully isolated free of surrounding tissues (about 2 cm). A perivascular probe connected to an ultrasonic flow meter (Transonic Flow Meter, N.Y.) was placed under and surrounding the carotid artery to monitor the blood flow rate. The experiments began with the injection of 0.2 ml of either saline or heparin solution via the penile vein. Exactly 1 min after injection, a piece of filter paper (6 mm in diameter, Whatman #5) soaked with 50 mole % $FeCl_3$ was placed on top of freed carotid artery. The filter paper was removed 15 minutes later. The experiment was terminated 1 h after $FeCl_3$ treatment and the carotid artery (2 cm) was removed. The thrombus (if formed) was removed and weighed wet. The total occlusion time (TOT), the time it takes for the blood flow to completely stop, as well as the thrombus weight were recorded.

Results

Figure 4A:
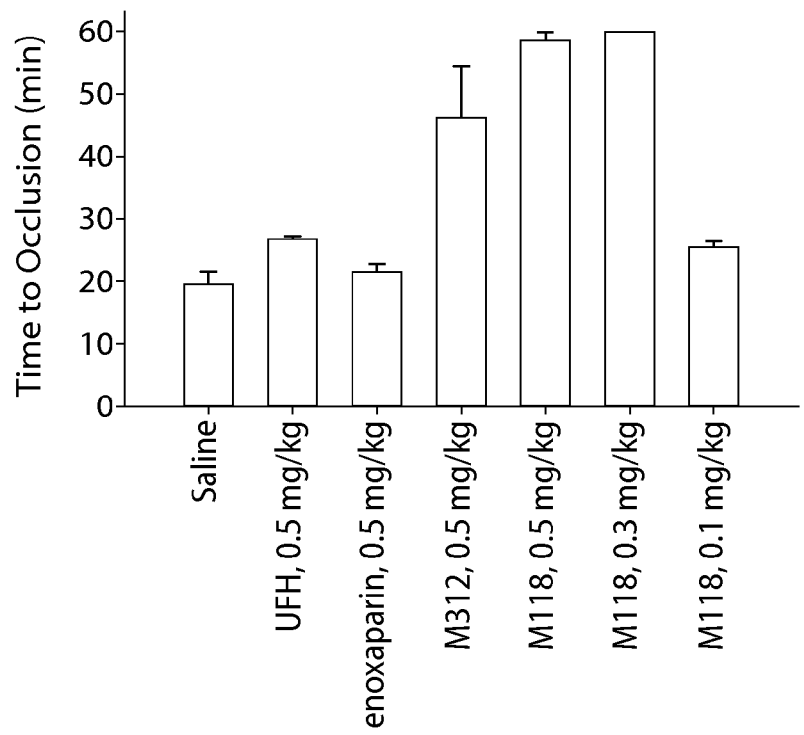
FIG. 4A Bar graph representing total occlusion time as a function of different heparins (UFH, enoxaparin, M118, and M312) as well as at different doses.
Figure 4B:
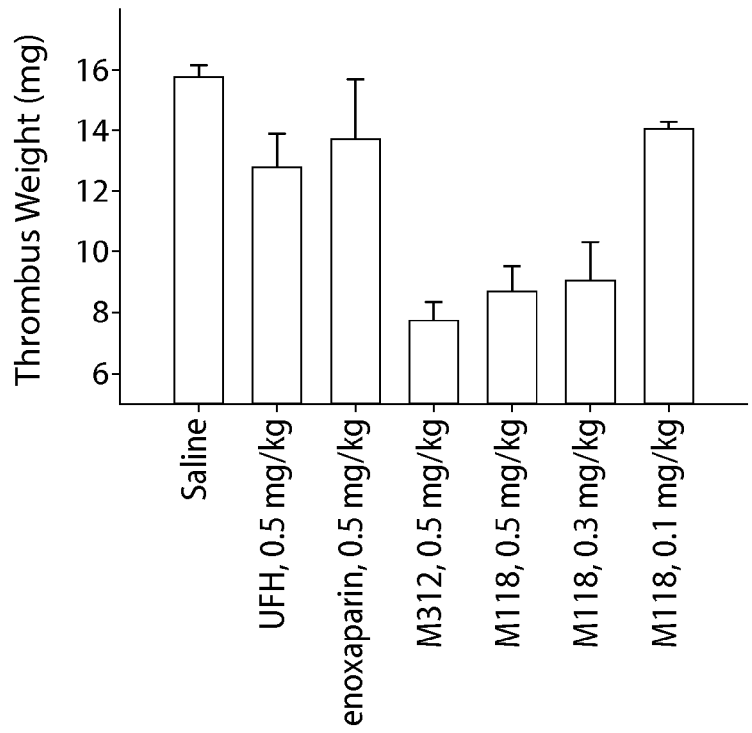
FIG. 4B. Bar graph representing thrombus weight as a function of heparin treatment at different doses for UFH, enoxaparin, M118, and M312. Thrombus was weighed at the end of the 1 hour thrombus induction period.

FIG. 4 shows the anti thrombotic activity of heparin in the rat arterial thrombosis model as well as the thrombus weight. Thrombus was weighed at the end of the 1 hour thrombus induction period. The total occlusion time and thrombus weight as a function of different heparins at different doses is given in FIG. 4. At 0.5 mg/kg, UFH prolonged the total occlusion time (TOT) to about 27 minutes compared to that of 17 minutes for the control group. It is noticed that a much lower dose is required for F1 to achieve a similar antithrombotic effect as that of UFH and Enoxaparin. A slightly weaker inhibition was observed for enoxaparin (TOT=23 min). This inhibition of thrombus formation was also observed in the final thrombus weight.

In contrast, at the same dose of 0.5 mg/kg, M115 completely prevented the occlusion of the artery. In this case, the blood flow rate never reached 0 within the 60 minutes observation window. This is also reflected by the significantly reduced thrombus weight at the end of 60 minutes. At 0.3 mg/kg, essentially the same responses were observed, namely no complete occlusion occurred and a significantly reduced thrombus weight was observed within the 60 minute period. At 0.1 mg/kg, the TOT and thrombus weight of M115 treated group became comparable to that observed for UFH and enoxaparin at 0.5 mg/kg. M411 was also an extremely potent inhibitor of arterial thrombosis formation, though less so than M115, as expected from its slightly decreased anti-IIa activity in vitro. Thus, a higher anti-IIa activity is associated with more potent inhibition of arterial thrombosis formation. In addition, the increased potency of M115 and M411 is consistent with their in vitro activity as well their favorable pharmacokinetics, especially bioavailability.

Example 4 s.c. Administered M115 and M411 is Associated with Increased Plasma TFPI Activity Accumulating evidence indicates that the complex tissue factor (TF)-activated factor VIIa (FVIIa) is a key initiator of arterial thrombosis in vivo. TFPI is a potent inhibitor of the tissue factor coagulation pathway, which exerts its function by neutralizing the catalytic activity of factor Xa and by feedback inhibition of the factor VIIa-TF complex in the presence of factor Xa. UFH and LMWH, in addition to their well-studied ability to promote the inhibitory activity of ATIII, also release TFPI from endothelial cells. This function further contributes, in a dramatic fashion, to the overall anti-coagulant and antithrombotic activity of heparin and LMWHs. In fact, studies have found that LMWHs are known to more efficiently release TFPI into the blood and thereby promote a favorable anticoagulant function as compared to UFH. Given the importance of TFPI release in the overall function of pharmacologic UFH and LMWHs, we sought to measure the effect of M115 and M411 on TFPI release in vivo. We measured the activity of TFPI in the plasma after s.c. administration of M115 and M411, UFH, or dalteparin as a model LMWH. To establish a release profile, plasma samples collected at different time points were tested.

Methods

TFPI activity in rabbit plasma after single s.c. administration of heparin was determined by a 2-step colorimetric assay. Briefly, in the first step, a dilution of the test sample was incubated with a saturating concentration of FVII/IIa a complex. In the second step, a high concentration of FX was added to the reaction mixture as a substrate for the residual FVIIa-TF catalytic activity; the FXa generated is measured with a specific chromogenic substrate (American Diagnostica Inc, Connecticut). The absorbance was read at 405 nm. Linear calibration curves were obtained with standard plasmas provided by the manufacture (American Diagnostics Inc). All test samples were assayed at a 5 mole % dilution. Results am expressed as percent of TFPI activity in pooled rabbit plasma.

Results

Figure 5:
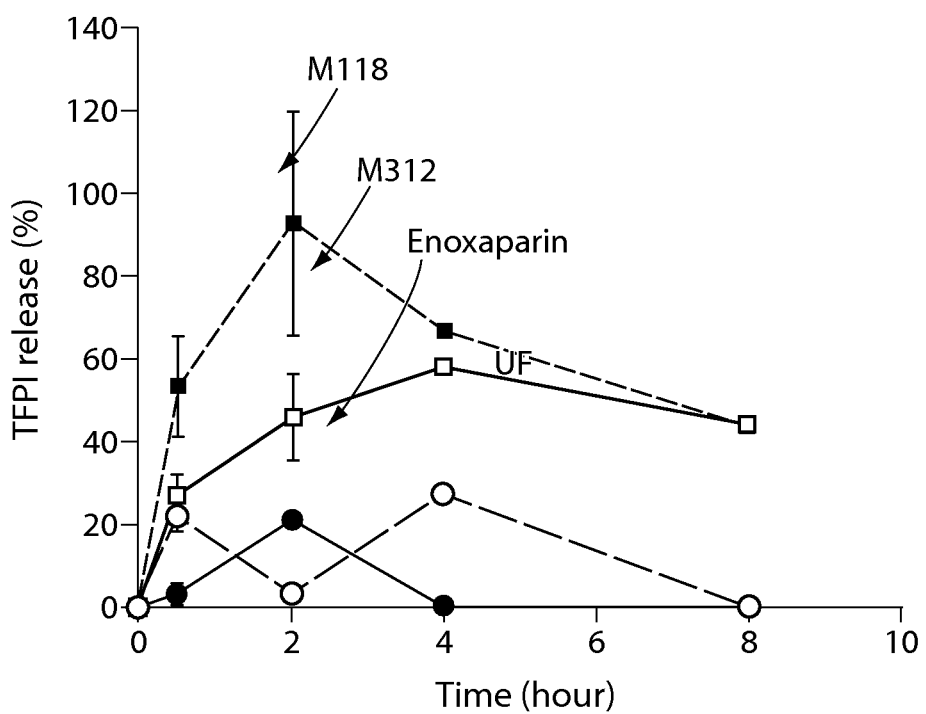
FIG. 5. Line graph of TFPI release profiles after s.c. administration of different heparins at 3 mg/kg. The release of TFPI is reflected by percentage increase in the plasma TFPI activity as determined by a chromogenic assay.

TFPI release profiles after s.c. administration of different heparins at 3 mg/kg are shown in FIG. 5. The release of TFPI is reflected by percentage increase in the plasma TFPI activity as determined by a chromogenic assay. It is noticed that F1 treatment led to a significant higher level of TFPI activity, which also persisted longer than other heparin treatments.

Compared to UFH and dalteparin, s.c. administration of either M115 or M411 is associated with a more pronounced release of TFPI into the circulation. The peak TFPI activity is reached about 4 hours after s.c. administration. TFPI activity is also elevated in the plasma from UFH treated animals, albeit, to a lesser extent. Surprisingly, dalteparin, a LMWH, only resulted in minimal increase of plasma TFPI activity. The results from this experiment strongly suggest that the administration of M1115 or M411 is associated with superior mobilization of TFPI from the endothelium, more so than either UFH or dalteparin.

Example 5

M115 or M411 are More Potent Anticoagulants than UFH

Anti-coagulation has been the primary clinical application for UFH for over 65 years. Due to its erratic pharmacokinetics following s.c. administration, UFH has been administered by intravenous injection instead. Additionally, the application of UFH as an anticoagulant has been hampered by the many side effects associated with non-specific plasma protein binding with UFH. Therefore, it is important to develop a novel LMWH that retains the anticoagulant activity of UFH but has reduced side effects. LMWHs, essentially due to their reduced chains sizes and dispersity, display markedly less non-specific plasma protein binding. However, all LMWHs that are currently clinically available also possess reduced anti-IIa activity compared to UFH. Because of this decreased activity, a larger dose of LMWH is required (compared to UFH) in order to achieve a similar anti-coagulant activity. Consequently, the use of LMWHs so far has been largely limited to the prevention of thrombosis and not to their treatment.

Methods

The second generation LMWHs reported here are unique for a number of reasons. First, while M115 and M411 have lower molecular weight than UFH and are in the accepted molecular weight range for LMWHs, these molecules possess high anti-Xa and IIa activities, 2-4 times higher than that of UFH or other LMWH on a mass basis. In addition, when compared to a typical LMWH, both M115 and M411 have 5-10 times higher anti-IIa activity as well as enriched anti-Xa activity. The efficiency of M115 and M411 as anticoagulants was compared to that of conventional UFH. To test this, a rat tail bleeding time assay was completed. The bleeding time was determined with a rat model as described with minor modifications. Specifically, male Sprague-Dawley rats weighing 350-400 g were used. Intraperitoneal injection of Pentobarbital at 55 mg/kg was used for anesthesia. Saline or heparin solution were injected via the penile vein of the rats. 1 min after injection, rat tail was cut 2 mm from the tip with a razor blade. The bleeding tail was blotted with a Whatman #3 filter paper every 30 seconds until the blot is free of blood, and the time was recorded.

Results

Both M115 or M411 showed a much more potent anticoagulant effect in this model, consistent with their increased anti-Xa and IIa activity. At 0.5 mg/kg, the bleeding time of sgL-1 treated rats exceeded 60 min compared to that of 20 minutes for UFH. At 0.3 mg/kg, the bleeding time became comparable to that of UFH and at 0.1 mg/kg the bleeding time returned to baseline level. Similarly, rats treated with M411 demonstrated markedly longer bleeding times than those treated with UFH.

Example 6

Creation of a Panel of LMWH with Different Ratios of Anti-Xa and Anti-IIa Activity One of the drawbacks associated with the LMWH therapies currently known in the art is an inability to individually tailor LMWH treatment to a subject. Until now, there has not been a preparation that is both sufficiently well characterized and consistent from batch to batch, as the methods for preparing LMWHs known in the art were inadequate to produce such preparations. The methods of the invention allow the preparation of consistent and predictable compositions of LMWH with desired properties, for instance, a LMWH preparation with a given ratio of anti-Xa:anti-IIa activity. This method can be used to produce a panel of LMWH preparations with varying degrees of anti-IIa and anti-Xa activity, among other characteristics. This method is not limited to manipulating anti-IIa or anti-Xa activity, but can be extended by using the methods disclosed and claimed herein to produce LMWH preparations with other desired characteristics, such as ultra-low molecular weight. PF4 binding, protamine neutralization, FGF binding, etc. The compositions made by this method can then be used to tailor treatment if a subject to their status; for instance, in the treatment of a clot, it might be advantageous to administer a LMWH preparation having high anti-Xa/anti-IIa activity early in the treatment cycle, and later switch to a LMWH preparation having only anti-Xa activity.

Methods.

A "grid" procedure was used to make a number of LMWH preparations with variable structural signatures. One example, not meant to be limiting, of a grid is illustrated below; it is used by moving down the grid from top to bottom, choosing any one of the options available in each row. Each option is intended as a guide and one of ordinary skill in the art will understand that options between and beyond those illustrated below are within the scope of the invention. Specific examples using the grid are described below. As one example, one may start with UFH, at a concentration of 10 mg/ml, precipitate with $MgCl_2$, choose methanol for use as the polar solvent for steps 1 and 2, and so on and so forth. It is not necessary to stay in a single column; the choice of an option may affect the structural signature of the resulting composition.

|  | Starting material | | | |
| --- | --- | --- | --- | --- |
|  | Unfractionated Heparin | enoxaparin | dalteparin | Other LMWH |
| Concentration of Starting material | 1 mg/ml | 10 mg/ml | 100 mg/ml | 1 g/ml |
| Salt Type | NaCl | Na-acetate | $MgCl_2$ | Other salt |
| Polar solvent used in step 1, and 2 | Acetone | Ethanol | Methanol | Other solvent |
| Quantity of Polar solvent used | 0.1 V (where 1 V = volume of heparin solution in water) | 1 V | 2 V | 10 V |
| Reaction Time for step 1 | 1 h | 6 h | 12 h | 24 h |
| ReactionTime for step 2 | 1 h | 6 h | 12 h | 24 h |
| ReactionTime for step 3 | 1 h | 6 h | 12 h | 24 h |
| Reaction Temperature for step 1 | 0 C. | 4 C. | 10 C. | RT |
| Reaction Temperature for step 2 | 0 C. | 4 C. | 10 C. | RT |
| Reaction Temperature for step 3 | 10 C. | RT | 37 C. | 45 C. |
| Depolymerizing agent (Enzyme/Chemical/Energy source like γ-radiation) | Heparinase 1 | Heparinase II | Heparinase III | Heparinase IV or mammalian Heparanase |

Synthesis of Enoxaparin-Derived LMWH Compounds

Step 1: 100 mg of enoxaparin was dissolved in 10 ml of water to get 10 mg/ml concentration. 100 mg NaCl was added to this solution. The pH of the solution was adjusted to 6.7. 5 ml 200 Proof ethanol was added to this mixture. The solution was maintained at 4 C for 24 h. The residue (MLP) that is precipitated is removed by centrifugation at 4000 RPM for 15 min. 20 ml ethanol was added to the supernatant, and the mixture maintained at 4° C. for 24 h. The precipitate formed at the end of 24 hours (MLS) is separated by centrifugation at 4000 RPM for 15 min. It is lyophilized overnight to give 60 mg dry powder of MLS.

Step 2: 100 mg MLS was dissolved in 10 ml of 50 mM Calcium Acetate buffer, pH 6.7. An enzyme cocktail consisting of 10 mg Heparinase II and 1 mg of Heparinase III was added to this mixture, and the solution was maintained at 37° C. for 4 h. The precipitate formed at the end of 2 hours was removed by centrifugation at 4000 RPM for 15 min. The supernatant of digested MLS was desalted in a size exclusion chromatography column.

Step 3: 100 mg MLS digested by the method explained above was loaded on a 1 m long, 10 cm diameter P10 size exclusion column. 500 mM Ammonium Acetate buffer was used as the running buffer. The eluent was tracked by absorption at UV 232 nM. 3 ml peaks were collected after the initial void volume. The peaks that gave absorption of more than 0.1 unit were collected. They were divided into 10 equal fractions. The different fractions were then lyophilized from water to get rid of ammonium bicarbonate salt. They were then assayed for the building blocks and functional characteristics (anti-Xa, and anti-IIa activity) by the assays described. Characteristics of Fraction 3 and Fraction 7 (named as M108, and M405) are listed in the table below.

Synthesis of UFH-Derived LMWH Compounds

Step 1: 100 mg of UFH was dissolved in 10 ml of water to get 10 mg/ml concentration. 100 mg NaCl was added to this solution. The pH of the solution was adjusted to 6.7. 3 ml 200 Proof ethanol was added to this mixture. The solution was maintained at 4 C for 12 h. The residue (MUP) that is precipitated is removed by centrifugation at 4000 RPM for 15 min. 10 ml ethanol was added to the supernatant, and the mixture maintained at 4° C. for 24 h. The precipitate formed at the end of 24 hours (MUS) is separated by centrifugation at 4000 RPM for 15 min. It is lyophilized overnight to give 60 mg dry powder of MUS.

Step 2: 100 mg MUS was dissolved in 10 ml of 50 mM Calcium Acetate buffer, pH 6.7. An enzyme cocktail consisting of 5 mg Heparinase II and 5 mg of Heparinase III was added to this mixture, and the solution was maintained at 37° C. for 4 h. The precipitate formed at the end of 2 hours was removed by centrifugation at 4000 RPM for 15 min. The supernatant of digested MUS was desalted in a size exclusion chromatography column.

Step 3: 100 mg MUS digested by the method explained above was loaded on a 1 m long, 10 cm diameter P10 size exclusion column. 500 mM Ammonium Acetate buffer was used as the running buffer. The eluent was tracked by absorption at UV 232 nM. 3 ml peaks were collected after the initial void volume. The peaks that gave absorption of more than 0.1 unit were collected. They were divided into 10 equal fractions. The different fractions were then lyophilized from water to get rid of ammonium bicarbonate salt. They were then assayed for the building blocks and functional characteristics (anti-Xa, and anti-IIa activity) by the assays described. Characteristics of Fraction 2 and Fraction 4 (designated M115, and M411) are listed below.

Results.

The methods described above were used to prepare and characterize the following LMWH compositions:

TABLE 7

Novel LMWH compositions, AUC as determined by CE analysis.

| AUC % | M108 | M405 | M115 | M411 |
|---|---|---|---|---|
| p1 | 60.9 | 61.9 | 53.8 | 54.0 |
| p2 | 6.8 | 8 | 5.7 | 6.6 |
| p3 | 14.7 | 10.4 | 18.5 | 18.7 |
| p4 | 2.7 | 1.6 | 3.4 | 3.5 |
| p5 | 1.6 | 4.3 | 0.4 | 0.5 |
| p6 | 2.3 | 3.9 | 1.4 | 1.6 |
| p7 | 4.4 | 5.8 | 9 | 8.9 |
| p8 | 6.1 | 2.6 | 8.1 | 6.2 |
| p9 | 0.3 | 0.7 | | |
| p10 | 0.2 | 0.6 | | |
| Anti-Xa, IU/mg | 150 | 80 | 250 | 200 |
| Anti-IIa IU/mg | 130 | 0 | 200 | 130 |
| MW, Da | 5000 | 2200 | 5000 | 4500 |

TABLE 8

Novel LMWH compositions, mole % of given components.

| Mole % | M108 | M405 | M115 | M411 |
|---|---|---|---|---|
| p1 | 62.7 | 67.0 | 55.3 | 56.7 |
| p2 | 6.3 | 7.7 | 5.2 | 6.2 |
| p3 | 12.6 | 9.3 | 15.8 | 16.3 |
| p4 | 2.3 | 1.4 | 2.9 | 3.0 |
| p5 | 1.0 | 2.8 | 0.2 | 0.3 |
| p6 | 1.0 | 1.7 | 0.6 | 0.7 |
| p7 | 2.6 | 3.6 | 5.3 | 5.3 |
| p8 | 11.1 | 5.0 | 14.7 | 11.5 |
| p9 | 0.3 | 0.8 | 250 | 200 |
| p10 | 0.2 | 0.6 | | |
| Anti-Xa, IU/mg | 150 | 80 | 250 | 200 |
| Anti-IIa IU/mg | 130 | 0 | 200 | 130 |
| MW. Da | 5,000 | 2200 | 5000 | 4500 |

We used the "grid" procedure described above for making M108, M405, M115, and M411, the specific examples mentioned above. It is to be understood that these are complex molecules obtained from a complex starting material by varying multiple parameters. Since the composition of the product is affected by multiple parameters, adjusting different parameters in different ways, and monitoring the profile of the product, would allow one of ordinary skill in the art to prepare products similar to M108, M405, M115, and M411.

Figure 6:
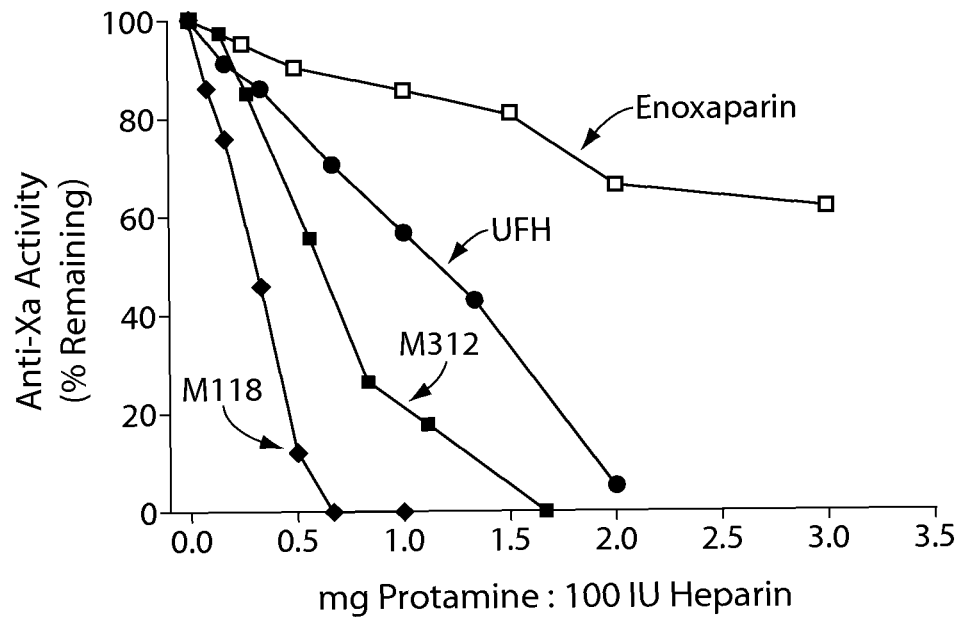
FIG. 6. Line graph of In vitro protamine neutralization of various LMWH (enoxaparin, M118, and M312) and UFH as a function of their anti-Xa activity is depicted here. M118, M312, and UFH are neutralized by using ≤2 mg/100 IU of heparin/LMWH while enoxaparin has about 60% of its anti-Xa activity still remaining even after using ≥3 mg/100 IU enoxaparin.
Figure 7:
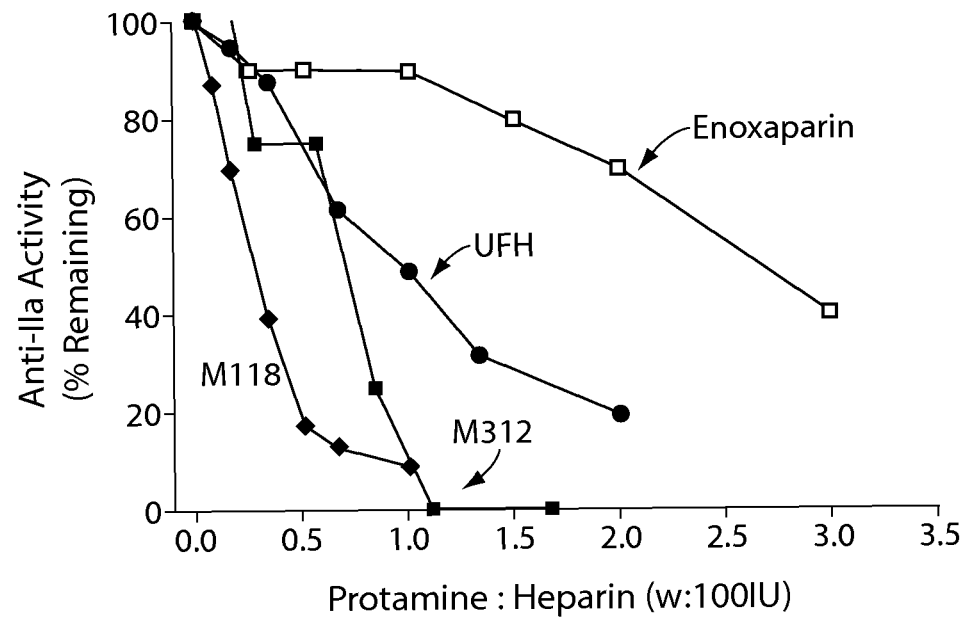
FIG. 7. Line graph of In vitro protamine neutralization of various LMWH (enoxaparin, M118, and M312) and UFH as a function of their anti-IIa activity is depicted here. M118, M312, and UFH are neutralized by using ≤2 mg/100 IU of heparin/LMWH while enoxaparin has about 40% of its anti-IIa activity still remaining even after using ≥3 mg/100 IU enoxaparin.
Figure 8:
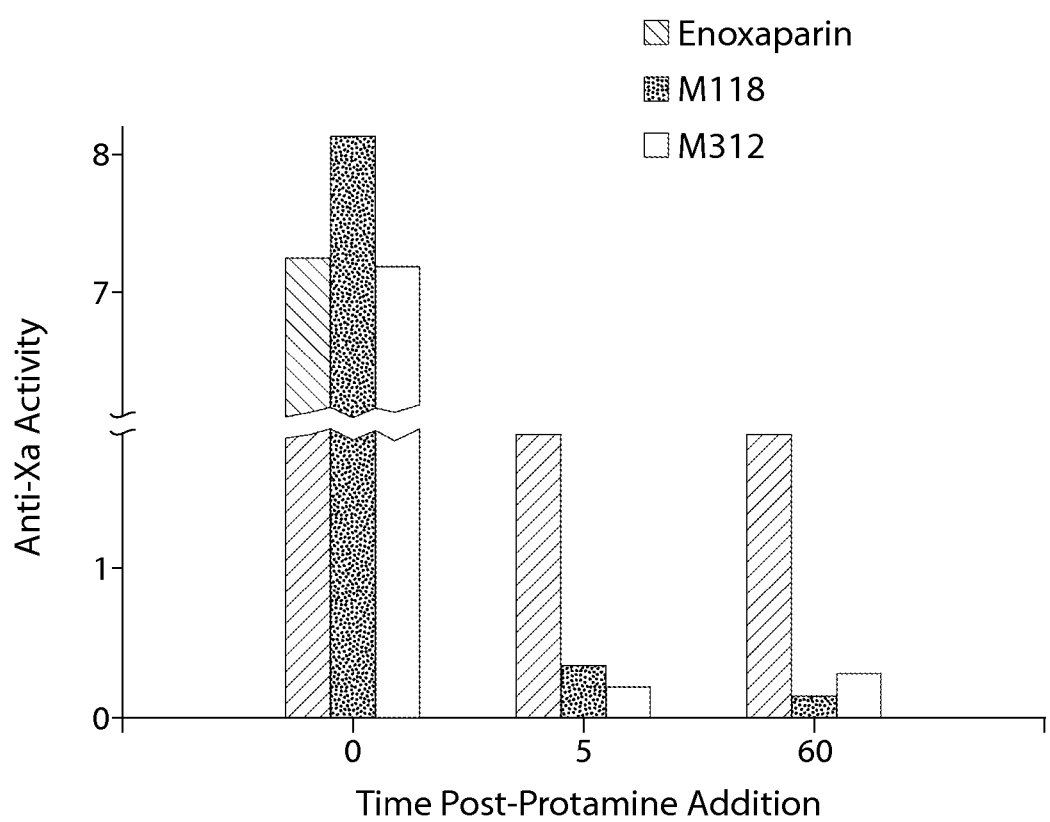
FIG. 8. Bar graph of In vivo protamine neutralization of enoxaparin, M118 and M312.
Figure 9:
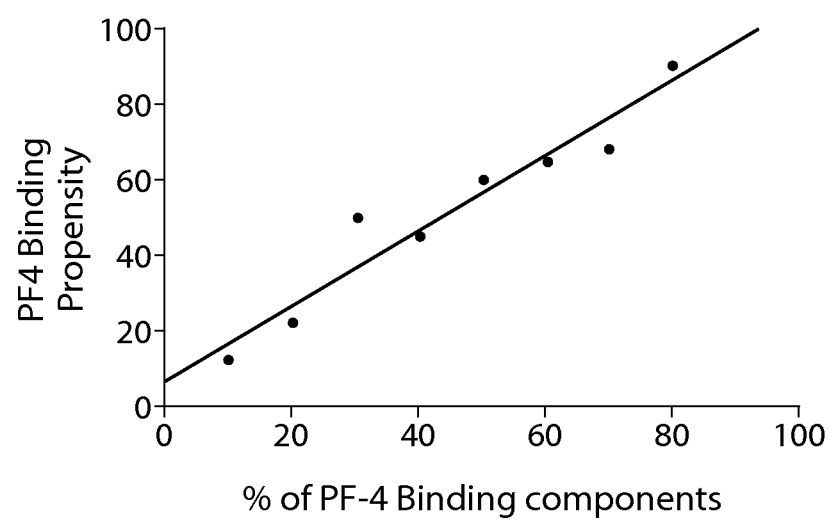
FIG. 9. Line graph depicting the linear relationship between the amount of PF4 binding components (peaks 1, 2, 4 and 6) in a LMWH preparation and PF4 binding propensity.

The parameters that can be varied include, but are not limited to:

1) Starting material: UFH, FH, other LMWH preparations such as enoxaparin (Lovenox™); dalteparin (Fragmin™); certoparin (Sandobarin™); ardeparin (Normiflo™); nadroparin (Fraxiparin™); parnaparin (Fluxum™); reviparin (Clivarin™); tinzaparin (Innohep™ or Logiparin™), among others.
2) Salt (type, concentration): such as divalent metals such as Mg, and Ca (e.g., $MgCl_2$, Calcium acetate, etc.).
2) Enzyme (Heparinase I, II, III, IV, heparanases, mutant heparinases, and different combinations of these enzymes).
3) Temperature
4) Incubation time This method has been used to create LMWH preparations with different characteristics. For instance, LMWH preparations which are fully neutralized by protamine can be created, such that the addition of protamine neutralizes anti-Xa activity by ≥50% and anti-IIa activity by ≥70%. As can be seen in FIGS. 6, 7 and 8, novel LMWH preparations M118 and M312 (which are prepared in a manner similar to M115, and M411) are both more sensitive to protamine neutralization of anti-Xa and anti-IIa activity than either UFH or enoxaparin. In addition, LMWH preparations with lower PF4 binding activity have been created, as can be seen in table 9, these preparations have lower amounts of components 1, 2, 4, and 6, which are associated with PF4 binding; see also FIG. 9. Since PF4 binding has been linked to heparin induced thrombocytopenia (HIT), a composition of LMWH with decreased PF4 binding would be very desirable.

PF4 binding was assayed using the filter binding assay of Maccarana et al. Briefly, 1 μg of 3H-radiolabeled heparin is incubated with 1 μg of PF4 in the presence of various amounts of nonradioactive LMWHs for 10 min at 37° C. in 10 μl of Tris buffer (130 mM NaCl, 50 mM Tris-HCl, pH 7.3). The volume is then made up to 300 μl by the addition of Tris buffer, and the samples are drawn through buffer-equilibrated cellulose nitrate filters on a vacuum manifold. The filters are washed with 2×5 ml of 130 mM NaCl, 50 mM Tris-HCl, and bound material eluted with 2×5 ml of 2 M NaCl, 50 mM Tris-HCl. On average greater than 99% of the radiolabeled material was removed from the filters with 2 M NaCl, 50 mM Tris-HCl.

To assess PF4 binding affinity for the various LMWHs, Scatchard analysis of the data collected by the filter binding assay was used. The lines of best fit and graphical equations for the data were determined. The gradients of these lines are equivalent to $1/Kd(1)$ and $1/Kd(2)$, the x intercept for the first line represents the number of binding sites on the protein (n1), and the x intercept for the second represents n1+n2, where n2 is the number of binding sites with $Kd(2)$.

TABLE 9

Comparison of equivalent Anti-Xa activity for side effects

| | Saccharide components | | |
|---|---|---|---|
| | Enoxaparin | M118 | M312 |
| Total (mg) | 100 | 32.0 | 48.4 |
| p1 (mg) | 63.5 | 18.9 | 29.7 |
| p2 (mg) | 7.2 | 1.8 | 3.3 |
| p4 (mg) | 2.1 | 0.4 | 0.9 |
| p6 (mg) | 2.0 | 0.1 | 0.3 |
| Anti-Xa (IU) | 100 | 100 | 100 |
| MW (Da) | 4,200 | 5,000 | 4,500 |

As is apparent from these results, the methods can be used to create a LMWH preparation with almost any characteristic desired, including varying ratios and levels of anti-Xa and anti-IIa activity; protamine neutralization; FGF binding; and PF4 binding.

Example 7

LMWH Preparations with Low Batch-Batch Variability

One of the great drawbacks of the UFH and LMWH preparations currently known in the art is their great variability in both composition and in activity. This has limited the population of patients for whom LMWH or UFH therapy was indicated, for instance excluding patients with abnormal renal function, among others. Abnormal renal function is measured by urea, creatinine, phosphorus, GFR or BUN in blood and urine. Administration of the known LMWH preparations is often a trial and error approach of titrating the appropriate dosage based on inaccurate tests, which can lead to unwanted and severe side effects such as post-operative bleeding. It would be greatly desirable to have a method for making LMWH preparations with low batch-batch variability and a desired structural signature. The methods of this invention allow for the creation of such preparations.

Methods.

Several enoxaparin preparations were depolymerized by a cocktail of enzymes, including heparinases. Next, a capillary electrophoresis (CE) profile of the resulting digest was run in an Agilent CE instrument in the negative mode. Shown in the table below are the disaccharide building blocks seen in three batches of commercially available enoxaparin. The composition is expressed as mole % of the building blocks of enoxaparin. This table teaches the composition as a mole % of the constituent building blocks. In, other words, one mole of enoxaparin is composed of X1 mole % of disaccharide building block 1, X2 mole % of disaccharide building block 2, . . . , XN mole % of building block "N". X1+X2+ . . . +Xn=100. The variation was calculated by taking the average of the three values, and dividing the largest deviation by the average.

TABLE 10

Enoxaparin Batch-to-batch Variation, mole %.

| Saccharide | Enox. Batch 1 | Enox. Batch 2 | Enox. Batch 3 | Variation (%) |
|---|---|---|---|---|
| p1 | 60.8 | 63.5 | 63.6 | 4 |
| p2 | 7.0 | 7.2 | 8.3 | 17 |
| p3 | 11.8 | 10.8 | 11.3 | 9 |
| p4 | 2.5 | 2.1 | 2.0 | 23 |
| p5 | 3.6 | 3.5 | 3.5 | 3 |
| p6 | 1.8 | 2.0 | 1.8 | 11 |
| p7 | 5.4 | 4.3 | 1.9 | 91 |
| p8 | 6.6 | 5.8 | 6.4 | 13 |
| p9 | 0.2 | 0.4 | 0.5 | 82 |
| p10 | 0.3 | 0.4 | 0.7 | 86 |

The table above demonstrates that the variation between batches of commercially available enoxaparin (Lovenox™) is substantial. To alleviate this problem, the methods of the current invention alleviate this problem by providing a method for quality control.

Results.

One example, not meant to be limiting, of the application of this method is as follows. First, a desired reference structural signature, mole %, or activity is selected, based upon a standard preparation that has, for instance, the desired activity at desired levels. Using the data in table 10, and maximizing for anti-Xa activity, a range of acceptable values would be chosen for mole % of peak 8, for example, 6.5 mole %. Within the scope of the invention, each batch of enoxaparin that is manufactured would then be subjected to the analysis methods of the invention, to determine the mole % of 8. Batches of enoxaparin that fell within a given variation of the desired range would be accepted; those that did not would be rejected. Again taking the data from table 10 for an example, if the desired mole % is 6.5, and the acceptable variation is 5%, then only those batches with a mole % of the peak 8 tetrasaccharide of 6.5±0.3 would be accepted. Thus, Batches 1 and 3 would be acceptable, but Batch 2 would be rejected as having insufficient levels of p8 (and thus insufficient levels of anti-Xa activity).

Further applications of this method include determining the structural signature of the starting material, e.g. porcine intestinal mucosa heparin. This starting material is isolated in slaughter houses and is often unmonitored by standard quality control techniques. Using the methods described above to ensure that the quality of the starting material, e.g., the structural signature and activity, is sufficient to produce acceptable LMWH preparations. Adding this quality control to the beginning of the procedure so that the starting material is consistent helps to decrease batch-batch variability, and thus decrease the number of rejected batches, saving time and money, and resulting in an improved product.

Example 8

Monitoring a Subject

The ability to track and monitor LMWH preparations in a subject, such as a human or veterinary subject, or an experimental animal, would greatly enhance both research and therapeutic applications of these preparations. To date, monitoring methods have relied on activity assays that suffered from numerous drawbacks, as described above.

Methods

Following administration of a LMWH preparation to a subject, e.g., a human or veterinary subject, or an experimental animal, a sample or samples are taken from that subject at various periods of time. The sample can be any bodily fluid, including but not limited to blood or urine. The sample is then purified by appropriate methods known in the art, such as those disclosed in U.S. Pat. No. 5,843,786; the method of purification will depend on the sample type. As one example, not meant to be limiting, the sample is blood. After removal of the whole cells by filtration or centrifugation, further filtration may be utilized to rid the sample of high molecular weight contaminants. The sample may be further purified to remove neutral contaminants by ion exchange methods conventionally known in the art. The sample may then be derivatized using methods known in the art. Finally, the sample is treated using the methods described above to depolymerized the polysaccharides prior to analysis, e.g., by CE, MALDI-MS, and/or PEN-MALDI. The sample may also be compared to a reference to quantify the levels of LMWH in the sample.

As one example, not meant to be limiting, the method is as follows. After s.c. or i.v. injection of heparin or LMWH, blood or urine samples were collected at selected timepoints. Samples were purified bound to a micro-DEAE column (Pharmacia-Biotech), washed with a buffer of 10 mM phosphate, 0.1M NaCl pH 6.0 and eluted with 10 mM phosphate 1M NaCl pH 6.0. The sample was then further purified and concentrated on a Microcon-3 spin column prior to enzymatic digestion and compositional analysis.

Figure 10A:
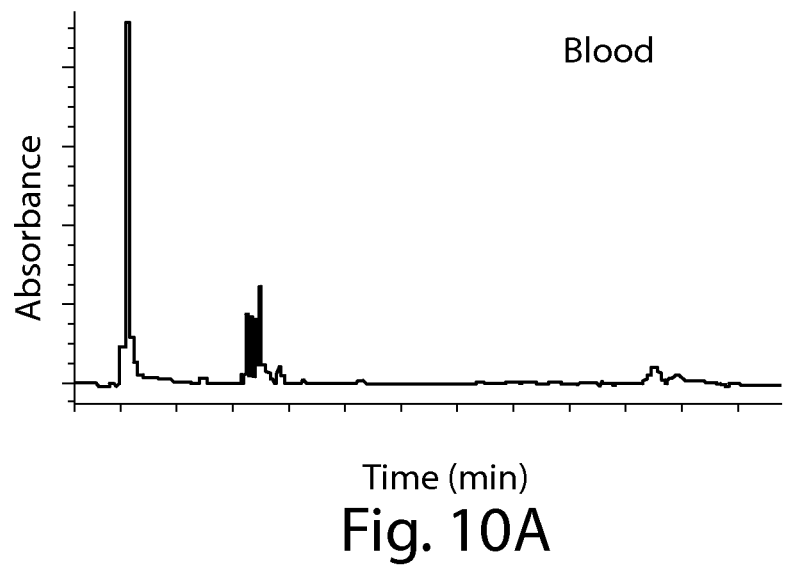
FIG. 10A. CE profile of a LMWH in Blood.
Figure 10B:
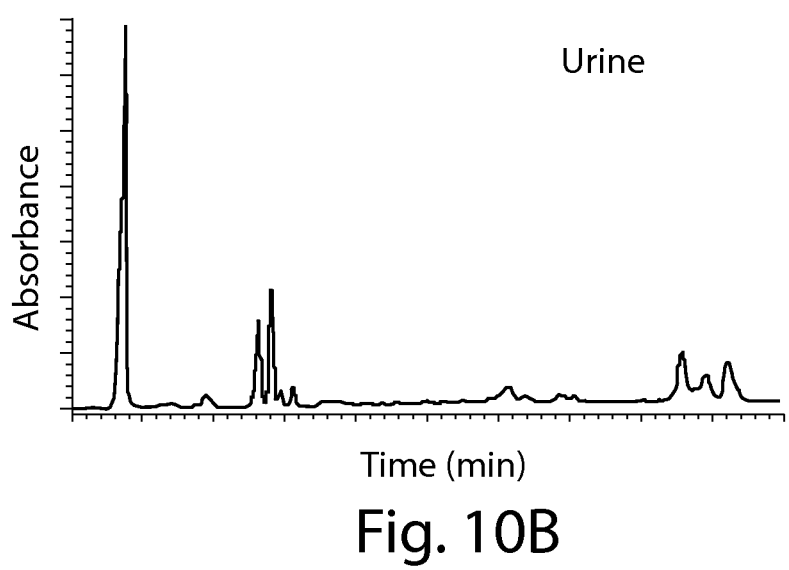
FIG. 10B. CE profile of the same LMWH in Urine.
Figure 11A:
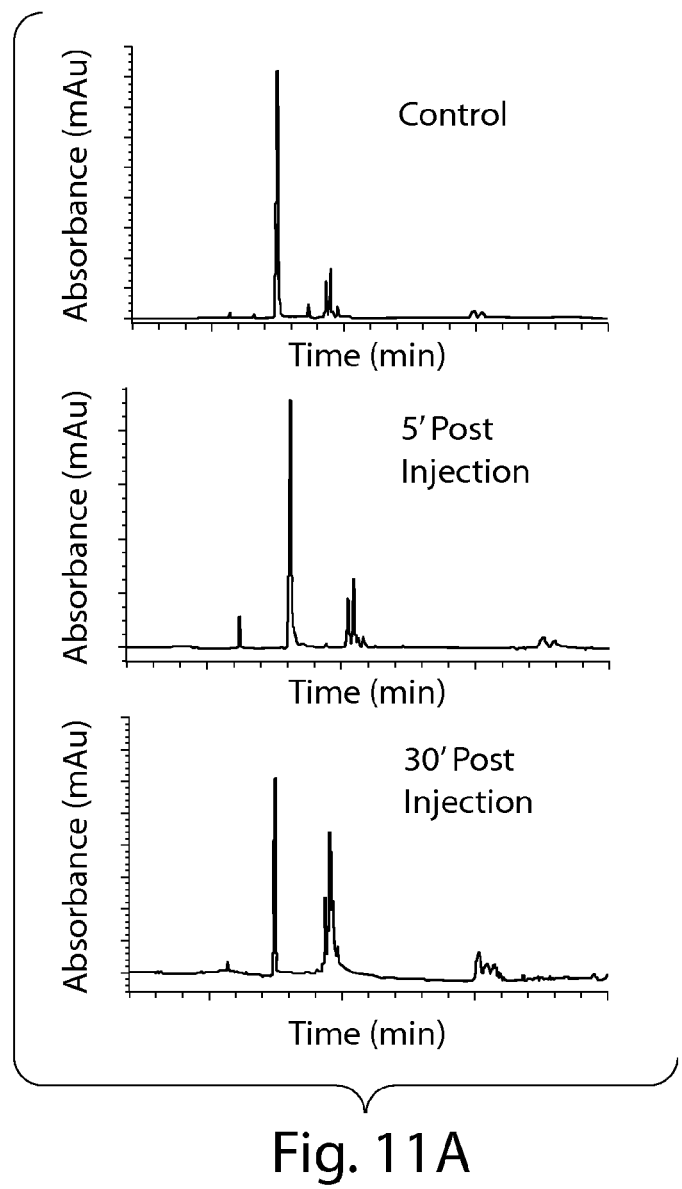
FIG. 11A. CE profile of enoxaparin in plasma before (top panel), at five minutes after administration (middle panel) and at thirty minutes after administration (bottom panel).
Figure 11B:
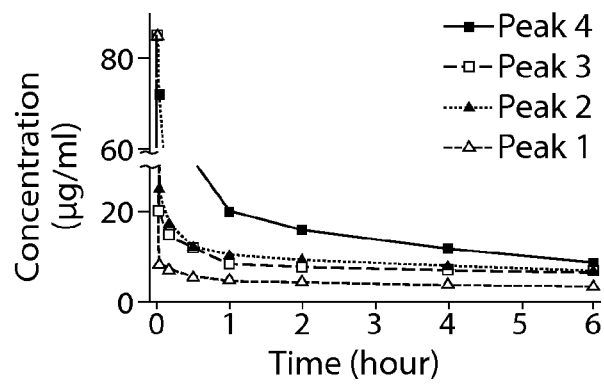
FIG. 11B. CE profile of enoxaparin in urine at different time points upon the administration of enoxaparin, showing the presence of peaks 1, 2, 3, and 4.
Figure 12:
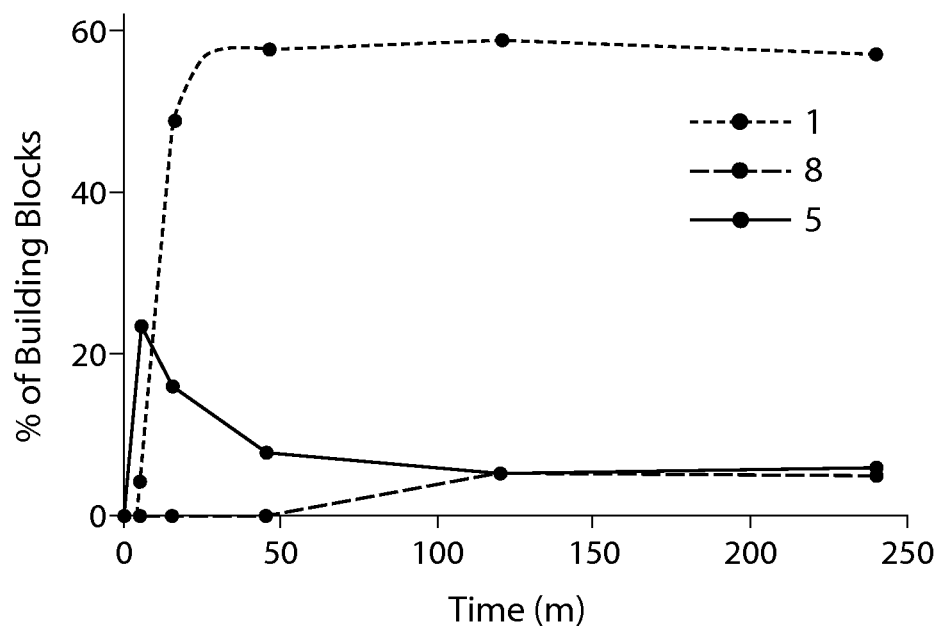
FIG. 12. Line graph showing the clearance of different building blocks of heparin and LMWH (enoxaparin, and other LMWH) in urine was tracked as a function of time. % of building blocks refers to the % of building blocks p1 (peak 1), p8 (peak 8) or p5 (peak 5), as a fraction of the total building blocks seen at that particular time point.

The sample was then subjected to exhaustive depolymerization with an enzyme cocktail made up of heparinase I, II, and heparinase III. 9 µl of 10 µg/µl concentration of UFH in $H_2O$ was digested with 1 µl of an enzyme cocktail consisting of 100 nM each of heparinase I, II, and III in 25 mM sodium acetate, 100 mM sodium chloride, 5 mM calcium acetate buffer, pH 7.0 for 12 hours at 37° C. The CE sample was prepared by diluting 1 µl of the digest with 9 µl of $H_2O$. The samples were analyzed by CE in reverse polarity with a running buffer of 50 mM tris/phosphate, 10 µM dextran sulfate, pH 2.5. The results are shown in FIG. 10. Using this method, the LMWH preparations can be monitored over time in a subject; the results are plotted against time, as is shown in FIGS. 11 and 12.

Example 9

Tagged LMWH Preparations

The ability to track and monitor LMWH preparations in a subject, such as a human or veterinary subject, or an experimental animal, would greatly enhance both research and therapeutic applications of these preparations. The use of a marker or tag built into the LMWH preparation significantly eases monitoring, quantitation and detection.

Methods.

Following the preparation of a LMWH, either by the methods disclosed herein or other methods known in the art, a label is attached to one or more of the constituent of the LMWH. Such a label can be a fluorophore (Morell at al., *Electrophoresis* (1998) 19(15):2603-11; Anumula at al., *Glycobiology* (1998) 8(7):685-94; Sudor at al., *Anal Chem* (1997) 69(16): 3199-204; Bigge et al., *Anal Biochem* (1995) 230(2):229-38; Franz et al., *J Am Soc Mass Spectrom* (2001) 12(12):1254-61; Drummond et al., *Proteomics* (2001) 1(2):304-10; Araki et al. *J Chromatogr B Biomed Sci* (2001) 753(2):209-15; Li et al., *Anal Biochem* (1993) 211(2):250-7); biotin (Imai et al., *FEBS Lett* (2002) 510(3):201-5; radioactive isotopes (Collard et al., *Anal Biochem* (1997) 247(2):448-50); mass-label; antigenic moieties, or other suitable labels known in the art. Preferably, the label is attached to an active constituent of the LMWH.

Thus labeled, the LMWH can be detected and quantified by methods known in the art. As one example, not meant to be limiting, a human or veterinary subject, or an experimental animal, is treated with a LMWH preparation including a tag. Then, a sample is taken from that subject. The sample may be subjected to purification under appropriate conditions known in the art, such as those disclosed in U.S. Pat. No. 5,843,786. The tag is then detected using appropriate methodology known in the art; for instance, if a fluorescent tag is incorporated into the LMWH preparation, fluorescence detection procedures may be utilized, such as is described in Araki et al., *J Chromatogr B Biomed Sci* (2001) 753(2):209-15.

The foregoing written specification is considered to be sufficient to enable one skilled in the art to practice the invention. The invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method of producing an enoxaparin pharmaceutical composition, the method comprising:
producing a batch of low molecular weight heparin (LMWH) by β-eliminative cleavage of a heparin preparation;
exhaustively digesting a sample of the batch of LMWH with two or more heparin degrading enzymes;
using a separation method to determine, in the sample that has been digested with two or more heparin degrading enzymes, the presence of a structural signature associated with the non naturally occurring sugar associated with peak 9 of FIG. 1 that results from β-eliminative cleavage;

selecting the batch of LMWH as a batch of enoxaparin if the non naturally occurring sugar associated with peak 9 is present in the sample compared to a pre-selected value for enoxaparin; and formulating the selected batch of enoxaparin for medical use, thereby producing an enoxaparin pharmaceutical composition.

2. The method of claim 1, wherein formulating comprises combining the batch of enoxaparin with a pharmaceutically acceptable carrier.

3. The method of claim 1, wherein the preselected value is an enoxaparin reference standard.

4. The method of claim 1, wherein the structural signature is determined using High Performance Liquid Chromatography (HPLC).

5. The method of claim 1, wherein the structural signature is determined using Capillary Electrophoresis (CE).

* * * * *